United States Patent
Zablocki et al.

(10) Patent No.: US 6,440,973 B1
(45) Date of Patent: Aug. 27, 2002

(54) ARYL AND HETEROARYL SUBSTITUTED FUSED PYRROLE ANTIINFLAMMATORY AGENTS

(75) Inventors: Jeffery A. Zablocki, Mountain View, CA (US); Eugene Tarlton, Jr., Superior, CO (US); James P. Rizzi, Niwot, CO (US); Nathan B. Mantlo, Lafayette, CO (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 09/644,102

(22) Filed: Aug. 23, 2000

Related U.S. Application Data

(62) Division of application No. 09/269,600, filed as application No. PCT/US97/21344 on Nov. 18, 1997.
(60) Provisional application No. 60/031,207, filed on Nov. 19, 1996.

(51) Int. Cl.[7] .................. A61K 31/495; A61K 31/50; C07D 403/00; C07D 241/50
(52) U.S. Cl. .................. 514/252.13; 514/253.01; 514/254.01; 514/255.05; 544/373; 544/405
(58) Field of Search .................. 514/252.13, 253.01, 514/254.01, 255.05; 544/373, 407

(56) References Cited

U.S. PATENT DOCUMENTS

| | | | |
|---|---|---|---|
| 3,420,838 A | 1/1969 | Szmuszkovicz | 260/326.15 |
| 3,429,874 A | 2/1969 | Topliss et al. | 260/562 |
| 3,551,567 A | 12/1970 | Fanshawe et al. | 260/326.16 |
| 3,565,912 A | 2/1971 | Szmuszkovicz | 260/326.16 |
| 3,654,308 A | 4/1972 | Szmuszkovicz | 260/326.6 |
| 3,929,807 A | 12/1975 | Fitzi | 286/294.8 |
| 4,343,811 A | 8/1982 | Hurnaus et al. | 424/274 |
| 5,338,849 A | 8/1994 | Festal | 546/113 |
| 5,502,187 A | 3/1996 | Ayer et al. | 544/117 |

FOREIGN PATENT DOCUMENTS

| | | |
|---|---|---|
| DE | 1795061 | 2/1972 |
| EP | 0539066 A1 | 4/1993 |
| EP | 0574618 A1 | 12/1993 |
| EP | 0 682 027 | 4/1995 |
| EP | 682027 * | 11/1995 |
| FR | 1587692 | 2/1970 |
| JP | 6-247967 | 2/1993 |
| JP | 06247966 | 9/1994 |
| WO | WO 88/01169 | 2/1988 |
| WO | WO 90/15534 | 12/1990 |
| WO | WO 91/00092 | 1/1991 |
| WO | WO 92/10190 | 6/1992 |
| WO | WO 92/10498 | 6/1992 |
| WO | WO 92/12154 | 7/1992 |
| WO | WO 93/14081 | 7/1993 |
| WO | WO 93/20078 | 10/1993 |
| WO | WO 94/14434 | 7/1994 |
| WO | WO 95/06040 | 3/1995 |
| WO | WO 95/33748 | 12/1995 |
| WO | WO 95/35304 | 12/1995 |
| WO | WO 96/03387 | 3/1996 |
| WO | WO 96/21452 | 7/1996 |
| WO | WO 96/21654 | 7/1996 |
| WO | WO 97/02266 | 1/1997 |
| WO | WO 97/16442 | 5/1997 |
| WO | WO 98/47899 | 10/1998 |

OTHER PUBLICATIONS

Baracos et al, N. Eng. J. Med. 308:553–558 (1983).
Winter et al Proc. Soc. Exp. Biol. Med. (1962) vol. 111, p 544–547.
Beutler et al, J. Immunol. 135(6):3969–3971 (1985).
Borne, Handbook of Cardiovascular and Anti–Inflammatory Agents, p. 27–104 (1986).
Brahn et al, Lymphokine Cytokine Res. (11):253–256, (1992).
Evans et al., J. Biol. Chem. 270(19):11477–83, (1995).
Guram & Buchwald et al., Angew. Chem. Int. Ed. Engl. 1348–1350 (1995).
Stupnikova et al., Ukr. Kim. Zh., 48(1), 76–9(1982).
Trentham et al J. Exp. Med. (1977) vol. 146, p 857–868.
Arcadi et al., Tetrahedron, 46(20):7151–64 (1990).
Wensbo et al., Tetrahedron Letters, 34(17):2823–2826 (1993).
Chandrasekhar et al., Clinical Immunol. Immunopathol. 55:382–400 (1990).
Swingle, K. F., in R. A. Scherrer and M. W. Whitehouse, Eds., Antiinflammatory Agents, Chemistry and Pharmacology, vol. 13–II, Academic, New York, 1974, p. 33–122, Chapter 2.
Clouse et al, J. Immunol. 142(2):431–438 (1989).
Cooper et al., Clin. Exp. Immunol. 89:244–250 (1992).
Courtenay et al., Nature, vol. 283, p. 666–668 (1980).

(List continued on next page.)

*Primary Examiner*—Richard L. Raymond
*Assistant Examiner*—Sudhaker B. Patel
(74) *Attorney, Agent, or Firm*—Steven M. Odre; Ron K. Levy; Frank S. Ungemach

(57) ABSTRACT

The present invention comprises a new class of novel aryl and heteroaryl substituted fused pyrrole compounds useful for the prophylaxis and treatment of diseases or conditions, such as TNF-α, IL-1β, IL-6 and/or IL-8 mediated diseases, and other maladies, such as pain and diabetes. In particular, the compounds of the invention are useful for the prophylaxis and treatment of diseases or conditions involving inflammation. Accordingly, the invention also comprises pharmaceutical compositions comprising the compounds of the invention, methods for the prophylaxis and treatment of inflammation and other maladies, such as pain and diabetes, using the compounds and compositions of the invention, and intermediates and processes useful for the preparation of compounds of the invention. The subject invention also relates to processes for making such compounds as well as to intermediates useful in such processes.

30 Claims, No Drawings

OTHER PUBLICATIONS

Shohami et al, J. Cereb. Blood Flow Metab. 14:615–619 (1994).
Dinarello, Charles A., Eur. Cytokine Netw. 5:517–531 (1994).
Shapiro et al., Proc. Natl. Acad. Sci. (USA) vol. 92, 12230–4 (1995).
Maini et al., Immunological Reviews No. 144, p. 195–223 (1995).
Liu et al., Neurosci. Lett. 164:125–128 (1993).
Liu et al., Stroke 25(7):1481–1488 (1994).
Beyaert et al., EMBO Journal, vol. 15, No. 8, p 1914–23 (1996).
Firestein et al., Am. J. Pathol. 140(6):1309–1314, (1992).
Folks et al, J. Immunol. 136(11):4049–4053, (1986).
Fürstner et al, Tet. Lett., 32(46):6695–6696 (1991).
Gallagher et al, Biorg. Med. Chem. Lett., 5(11):1171–1176 (1995).
Gribble, G., Recent Developments in Indole Ring Synthesis–Methodology and Applications in Contemporary Organic Synthesis p. 145–172.
Han et al., Biochimica Biophysica Acta 1265:224–227 (1995).
Lee et al., Nature 372:739–746 (1994).
Herbert et al., J. Chem. Soc. (C), p. 1505–1514(1969).
Lee et al, Circulatory Shock 44:97–103 (1995).
Lähdevirta et al, The American J. Med. 85:289–291 (1988).
Stupnikova et al., Khim. Geterotsikl. Soedin., (7), 959–64 (1980).
Joosten et al, Arthritis & Rheumatism 39(5):797–809 (1996).
Bundgaard et al., J. Med. Chem., 32(12):2503–2507 (1989).
Svensson et al., Drug Metabolism Reviews, 19(2):165–194 (1988).
Bumagin et al., Synthesis, 728–729 (1984).
Julia et al., J. Chem. Soc. Perkin Trans I, 1101–1105 (1991).
Wrobel et al., Tet. Lett., 34(22):3543–3546 (1993).
Jacini et al., Gazz. Chim. Ital, vol. 77:308–311 (1947).
Park et al., Bull. Korean Chem. Soc., 13(4):357–359 (1992).
Howbert et al., J. Med. Chem., 33:2393–2407 (1990).
Curran et al., J. Org. Chem., 55:4585–4595 (1990).
Trost et al., Tet. Lett., 22(14):1287–1290 (1981).
Baldenius et al., Tet. Asymmetry, 1(9):597–610 (1990).
Pascual, Bull. Soc. Chim. Belg., 101:297–302 (1992).
Rumler et al., Pharmazie, 45(9):657–659 (1990).
Farina et al., Tet. Lett., 32(34):4243–4246 (1991).
Takeuchi et al., Synthesis, 923–924 (1990).
Carlstrom et al., J. Org. Chem., 56:1289–1293 (1991).
Carlstrom et al., Synthesis, 414–418 (1989).
Bozell et al., J. Org. Chem., 56: 2584–2587 (1991).
Yamanaka et al., Chem. Pharm. Bull., 33(10):4309–4313 (1985).
Girshovich et al., Zh. Org. Khim., 27(10):2235–2236 (1991).
Bell et al., Synthesis, 843–844 (1987).
Bell et al., Tet. Lett., 29(39):5013–5016 (1988).
Siddiqui et al., Tet. Lett., 31(11):1523–1526 (1990).
Iihama et al., Synthesis, 184–188 (1989).
Hoshino et al., Bull. Chem. Soc. Jpn., 61:3008–3010 (1988).
Sato et al., Chem. Lett., 1405–1408 (1989).
Paul et al., J. Am. Chem. Soc., 5969–70 (1994).
Guram et al., J. Am. Chem. Soc., 116:7901–7902 (1994).
Davis et al., Tet. Lett., 32(13):1631–1634 (1991).
Differding et al., Synlett., 187–189 (1991).
Miyashita et al., Heterocycles, 42(2):691–699 (1996).
Fürstner et al., J. Org. Chem., 59:5215–5229 (1994).
Purohit et al., Indian Journal of Chemistry, vol. 32B, 257–261 (1993).
Mendel et al., Chemical Abstracts, 112:716 (1990).
Biere et al., Liebigs Ann. Chem., 491–494 (1987).
Black et al., Synthesis, 474–476 (1986).
Pichler et al., Liebigs Ann. Chem., 1485–1505 (1986).
Stupnikova et al., Chemical Abstracts, 96:17, 738 (1982).
Dave et al., J. Heterocyclic Chem., 17:1497–1500 (1980).
Hardy et al., J. Chem. Soc., Perkin Trans. I., 506–511 (1980).
Fenner et al., Arch. Pharm. (Weinheim) 311, 153–161 (1978)
Roth et al., Arch. Pharm. (Weinheim) 308, 252–258 (1975).
Clark et al., J. Chem. Soc., Perkin Trans I., 1361–1363 (1976).
Bancroft et al., J. Chem. Soc., Perkin Trans I., 1852–1858 (1974).
Deubel et al., Chem. Ber., 104, 705–716 (1971).
Kelly et al., J. Chem. Soc., 303–307 (1970).
Colonna et al., Gazz. Chim. Ital., vol. XCVI, 1410–1422 (1966).
Bancroft et al., J.C.S. Perkin I, pp. 465–467 (1977).
Saify et al., J. Pham. Univ Kar., 1(1), 83–88 (1982).
Monnet et al., J. Heterocyclic Chem. 26, pp. 1029–1037 (1988).
Brodrick et al., JCS Perkin I, pp. 1910–1913 (1975).
Kelley et al., Canadian J. of Chem. vol. 44, pp. 2455–2459 (1966).

* cited by examiner

ARYL AND HETEROARYL SUBSTITUTED FUSED PYRROLE ANTIINFLAMMATORY AGENTS

This application is a division of application Ser. No. 09/269,600, filed Jun. 8, 1999, which is a 35 USC 371 filing of Internatinal Application No. PCT/US97/21344, filed Nov. 18, 1997, which claims the benefit of U.S. Provisional Application Serial No. 60/031,207, filed Nov. 19, 1996, which are, in their entirety, hereby incorporated by reference herein.

BACKGROUND OF THE INVENTION

The present invention comprises a new class of compounds useful in treating diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. This invention, in particular, relates to novel aryl and heteroaryl substituted fused pyrrole compounds, compositions containing such compounds and methods of use of such compounds. The subject invention also relates to processes for making such compounds as well as to intermediates useful in such processes.

Interleukin-1 (IL-1) and Tumor Necrosis Factor alpha (TNF-a) are proinflammatory cytokines secreted by a variety of cells including monocytes and macrophages in response to many inflammatory stimuli (e.g. lipopolysaccharide—LPS) or external cellular stress (e.g. osmotic shock, peroxide). Elevated levels of TNF-α and/or IL-1 over basal levels have been implicated in mediating or exacerbating a number of disease states including rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur inpatients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

Several approaches have been taken to block the effects of TNF-a. One approach involves utilizing soluble receptors for TNF-a (e.g., TNFR-55 or TNFR-75) which have demonstrated efficacy in animal models of TNF-a mediated disease states (for a PEG dimer of TNFR-55 see Edwards CHI Meeting Nov. 13–15 (1995) and rhu sTNFR:Fc p-75 see Moreland). A second approach to neutralizing TNF-a utilizing a monoclonal antibody specific to TNF-a, cA2, has demonstrated improvement in swollen joint count in a Phase II human trial of rheumatoid arthritis (Feldmann et al Immunological Reviews p.195–223 (1995)).

The above approaches block the effects of TNF-a and IL-1 by either protein sequesterazation or receptor antagonism, but an additional approach to blockade is to intervene in the cellular production and secretion of IL-1 and/or TNF. There are numerous points for intervention between the extracellular stimulus and the secretion of IL-1 and TNF-a from the cell including interfering with transcriptional processes, interfering with translational processes, blocking signal transduction which may alter protein translation and/or transcription; and blocking release of the proteins from the cells. The most reliable effect to document is upon applying a given stimulus to a cell in vitro (eg. monocyte), a certain amount of TNF or IL-1 (note: quantitated by enzyme linked immunoabsorbent assay, ELISA) is secreted over basal levels in the culture medium. Evidence as to the nature of intervention between the extracellular stimulus and the secretion of IL-1 and TNF-a from the cell can be provided by in vitro biochemical experiments, but it does not preclude the fact that the compounds may be intervening at a yet undetermined point on the pathway between extracellular stimulus and secretion of protein. Pentoxifylline is an example of a compound that is believed to intervene at the transcriptional level of IL-1 protein synthesis. Evidence suggests that the antiinflammatory glucocorticoids block at both the transcriptional and translational levels (Lee et al Circulatory Shock 44:97–103 (1995)) of inflammatory mediators. Chloroquine (CQ) and hydroxychloroquine (HCQ) accumulate in lysosomes of monocytes (Borne Handbook of Cardiovascular and Anti-Inflammatory Agents p27–104 (1986)). CQ and HCQ inhibit cartilage cathepsin B and cartilage chondromucoprotease, and they may have membrane stabilizing effects on the lysozomes.

Since TNF-a is upstream in the cytokine cascade of inflammation wherein elevated levels of TNF-a lead to elevated levels. of other cytokines including IL-1, IL-6 and IL-8, inhibiting the production of TNF-a may also reduce levels of other cytokines including but not limited to IL-1, IL-6 or IL-8. IL-8 is implicated in exacerbating and/or causing many disease states in which massive neutrophil infiltration into sites of inflammation or injury (e.g., ischemia) is mediated by the chemotactic nature of IL-8 including but not limited to the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels would lead to diminished neutrophil infiltration. Evidence has been reported that suggests P-38 plays a role in TNF induced transcriptional activation of IL-6 production (see: Walter Fiers EMBO Journal 1996, vol. 15, p 1914–23) and of IL-8 production (Dinarello, Proc. Nat. Acad. Sci. 1995 Vol 92, 12230–4).

In rheumatoid arthritis, both IL-1 and TNF-a induce synoviocytes and chondrocytes to produce collagenase and neutral proteases which leads to tissue destruction within the arthritic joints. In a model of arthritis, collagen-induced arthritis (CIA) in rats and mice, intraarticular administration of TNF-a either prior to or after the induction of CIA led to an accelerated onset of arthritis and a more severe course of the disease (Brahn et al Lymphokine Cytokine Res. (11): 253–256, (1992); and Cooper Clin. Exp. Immunol. 898:244–250, (1992)).

It has been reported that TNF-a plays a role in head trauma, stroke, and ischemia. For instance, in animal models of head trauma (rat), TNF-a levels increased in the contused hemisphere (Shohami et al J. Cereb. Blood Flow Metab. 14:615–619 (1994)). In an model of ischemia wherein the middle cerebral artery was occluded in rats, the levels of mRNA of TNF-a increased (Feurstein et al Neurosci. Lett. 164: 125–128 (1993)). Administration of TNF-a into the rat cortex resulted in significant PMN accumulation in capillaries and adherance in small blood vessels. The TNF-a promotes the infiltration of other cytokines (IL-1b, IL-6), and also chemokines, which promote neutrophil infiltration into the infarct area (Feurstein Stroke 25:1481–1488 (1994)).

TNF-a may play a role in promoting certain viral life cycles and disease states associated with them. For instance, TNF-a secreted by monocytes induced elevated levels of HIV expression in a chronically infected T cell clone (Clouse et al, J. Immunol. 142: 431 (1989)). The role of TNF-a in the HIV associated states of cachexia and muscle degradation has been discussed (Lahdevirta et al The American J. Med. 85:289 (1988)).

Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; antiviral therapy including those viruses sensitive to TNF-a inhibition—HIV-1, HIV-2, HIV-3; cachexia; Reiter's syndrome; type II diabetes; bone resorption diseases; ischemia reperfusion injury; atherosclerosis; brain trauma; multiple sclerosis; sepsis; septic shock; and toxic shock syndrome.

In rheumatoid arthritis models in animals, multiple intraarticular injections of IL-1 have lead to an acute and destructive form of arthritis (Chandrasekhar et al Clinical Immunol Immunopathol. 55:382–400 (1990)). In studies using cultured rheumatoid synovial cells, IL-1 is a more potent inducer of stromelysin than is TNF-a (Firestein Am. J. Pathol. 140:1309–1314, (1992)). At sites of local injection, neutrophil, lymphocyte, and monocyte emigration occurs. The emigration is attributed to the induction of chemokines (i.e. IL-8), and the up regulation of adhesion molecules (Dinarello Eur. Cytokine Netw. 5:517–531 (1994)).

IL-1 does play a role in promoting certain viral life cycles. Cytokine-induced increase of HIV expression in a chronically infected macrophage line has been associated with the concomittant and selective increase of IL-1 production (Folks et al J. Immunol. 136:40–49, (1986)). The role of IL-1 in cachexia has been discussed (Beutler et al J. Immunol. 135:3969–3971 (1985)). The role of IL-1 in muscle degeneration has been discussed (Baracos et al N. Eng. J. Med. 308:553–558 (1983)).

IL-8 has been implicated in exacerbating and/or causing many disease states in which massive neutrophil infiltration into sites of inflammation or injury (eg ischemia) is mediated by the chemotactic nature of IL-8 including but not limited to the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 apparently also has the ability to activate neutrophils. Thus, reduction in IL-8 levels could lead to diminished neutrophil infiltration.

Substituted imidazole and fused imidazole compounds have been described for use in the treatment of cytokine mediated diseases by inhibition of proinflammatory cytokines, such as IL-1, IL-6, IL-8 and TNF. Substituted imidazoles for use in the treatment of cytokine mediated diseases have been described in WO 93/14081; WO 96/21452; and WO 96/21654 (each of which is incorporated herein by reference in its entirety). Substituted imidazoles for use in the treatment of inflammation has been described in U.S. Pat. No. 3,929,807 (which is incorporated herein by reference in its entirety). Substituted fused imidazole compounds for use in the treatment of cytokine mediated diseases have been described in WO 88/01169; WO 90/15534; WO 91/00092; WO 92/10190; WO 92/10498; WO 92/12154; and WO 95/35304 (each of which is incorporated herein by reference in its entirety).

Several classes of diamino substituted azaindole compounds have been reported to be useful in the treatment of a variety of diseases including inflammation (U.S. Pat. No. 5,502,187, which is incorporated herein by reference in its entirety). Several classes of substituted indole and azaindole compounds are known to be useful as endothelin receptor antagonists for treating hypertension, renal failure and cerebrovascular disease (WO 94/14434 and WO 95/33748, each of which is incorporated herein by reference in its entirety). A related class of substituted indoles has been reported as useful in the treatment of atherosclerosis (DE 2909779 A1, which is incorporated herein by reference in its entirety). Variously substituted 7-azaindoles have been prepared and reported for use as anti-ulcer drugs (JP 06247966, which is incorporated herein by reference in its entirety).

The preparation of 3-(4-pyridyl)indole compounds has been reported (U.S. Pat. No. 3,551,567; FR 1587692; DE 1795061; Ukr. Kim. Zh. (Russ. Ed.) (1982), 48(1), 76–9; Khim. Geterotsikl. Soedin. (1980), (7), 959–64; each of which is incorporated herein by reference in its entirety). The preparation of 2,3-diphenylindole derivatives has been reported (U.S. Pat. No. 3,654,308; U.S. Pat. No. 3,565,912; and FR 1505197; each of which is incorporated herein by reference in its entirety).

BRIEF DESCRIPTION OF THE INVENTION

The present invention relates to selected antiinflamatory compounds, analogs and pharmaceutically acceptable salts and prodrugs thereof. The subject compounds are characterized as aryl and heteroaryl substituted fused pyrrole compounds. The invention compounds advantageously treat inflammation related diseases. Therefore, this invention also encompasses pharmaceutical compositions and methods for prophylaxis and treatment of inflamation. The subject invention also relates to processes for making such compounds as well as to intermediates useful in such processes.

DETAILED DESCRIPTION OF THE INVENTION

In accordance with the present invention, there is provided an anti-inflammatory compound of the Formula:

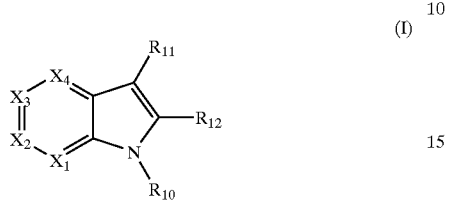

(I)

or a pharmacutically acceptable salt thereof, wherein $X_1$ is N, CH or $CR_1$; $X_2$ is N, CH or $CR_2$; $X_3$ is N, CH or $CR_3$; and $X_4$ is N, CH or $CR_4$; provided that at least one of $X_1$, $X_2$, $X_3$ and $X_4$ is N or CH, and that not more than two of $X_1$, $X_2$, $X_3$ and $X_4$ are N; wherein $R_1$, $R_2$, $R_3$ and $R_4$ are each independently —Z—Y;

preferably, $X_1$ is N; $X_2$ is CH or $CR_2$; $X_3$ is CH or $CR_3$; and $X_4$ is CH or $CR_4$; and more preferably, $X_1$ is N; $X_2$ is $CR_2$; $X_3$ is CH or $CR_3$; and $X_4$ is CH;

wherein $R_2$ is independently —Z—Y; and preferably, $R_2$ is independently Y; and $R_3$ is independently —Z—Y; preferably, $R_3$ is halo, trifluoromethyl, phenyl, methyl, hydroxymethyl, hydroxyethyl, dimethylamino, methoxy, trifluoromethoxy, —C(O)—$R_{20}$, —C(O)—$OR_{21}$, —C(O)—$NR_5R_{21}$, —S(O)$_2$—$R_{20}$ or —S(O)$_2$—$NR_5R_{21}$ radicals; more preferably, $R_3$ is halo, trifluoromethyl, phenyl, methyl, hydroxymethyl, hydroxyethyl, dimethylamino, methoxy, trifluoromethoxy, acetyl, methoxycarbonyl, ethoxycarbonyl, amido, N,N-dimethylamido, methylsulfonyl or aminosulfonyl radicals; even more preferably, $R_3$ is halo, trifluoromethyl, phenyl, methyl, hydroxymethyl, hydroxyethyl, methoxy, trifluoromethoxy, acetyl, methoxycarbonyl, ethoxycarbonyl, amido or N,N-dimethylamido radicals; and most preferably, $R_3$ is halo or trifluoromethyl radicals; and $R_4$ is independently —Z—Y; and preferably, $R_4$ is independently Y; or alternatively, preferably, $X_1$ is N; $X_2$ is CH or $CR_2$; $X_3$ is CH or $CR_3$; and $X_4$ is N; and more preferably, $X_1$ is N; $X_2$ is $CR_2$; $X_3$ is CH or $CR_3$; and $X_4$ is N;

wherein $R_2$ is independently —Z—Y; and preferably, $R_2$ is independently —Z—Y; and $R_3$ is independently —Z—Y; preferably, $R_3$ is halo, trifluoromethyl, phenyl, methyl, hydroxymethyl, hydroxyethyl, dimethylamino, methoxy, trifluoromethoxy, —C(O)—$R_{20}$, —C(O)—$OR_{21}$, —C(O)—$NR_5R_{21}$, —S(O)$_2$—$R_{20}$ or —S(O)$_2$—$NR_5R_{21}$ radicals; and most preferably, $R_3$ is halo, trifluoromethyl, phenyl, methyl, acetyl, hydroxymethyl, hydroxyethyl, dimethylamino, methoxy, trifluoromethoxy, methoxycarbonyl, ethoxycarbonyl, amido, N,N-dimethylamido, methylsulfonyl or aminosulfonyl radicals; or alternatively, preferably, $X_1$ is N; $X_2$ is CH or $CR_2$; $X_3$ is N; and $X_4$ is CH or $CR_4$; and more preferably, $X_1$ is N; $X_2$ is $CR_2$; $X_3$ is N; and $X_4$ is CH or $CR_4$;

wherein $R_2$ is independently —Z—Y; and preferably, $R_2$ is independently Y; and $R_4$ is independently —Z—Y; preferably, $R_4$ is halo, trifluoromethyl, phenyl, methyl, hydroxyethyl, hydroxymethyl, dimethylamino, methoxy, trifluoromethoxy, —C(O)—$R_{20}$, —C(O)—$OR_{21}$, —C(O)—$NR_5R_{21}$, —S(O)$_2$—$R_{20}$ or —S(O)$_2$—$NR_5R_{21}$ radicals; more preferably, $R_4$ is halo, phenyl, trifluoromethyl, methyl, hydroxymethyl, hydroxyethyl, dimethylamino, methoxy, trifluoromethoxy, acetyl, methoxycarbonyl, ethoxycarbonyl, N,N-dimethylamido, amido, methylsulfonyl or aminosulfonyl radicals; or alternatively, preferably, $X_1$ is N; $X_2$ is N; $X_3$ is CH or $CR_3$; and $X_4$ is CH or $CR_4$; and more preferably, $X_1$ is N; $X_2$ is N; $X_3$ is $CR_3$; and $X_4$ is CH or $CR_4$;

wherein $R_3$ is independently —Z—Y; and preferably, $R_3$ is independently Y; and $R_4$ is independently —Z—Y; preferably, $R_4$ is halo, trifluoromethyl, phenyl, methyl, hydroxymethyl, hydroxyethyl, dimethylamino, methoxy, trifluoromethoxy, —C(O)—$R_{20}$, —C(O)—$OR_{21}$, —C(O)—$NR_5R_{21}$, —S(O)$_2$—$R_{20}$ or —S(O)$_2$—$NR_5R_{21}$ radicals; and more preferably, $R_4$ is halo, trifluoromethyl, phenyl, methyl, hydroxymethyl, hydroxyethyl, dimethylamino, methoxy, trifluoromethoxy, acetyl, methoxycarbonyl, ethoxycarbonyl, amido, N,N-dimethylamido, methylsulfonyl or aminosulfonyl radicals; or alternatively, preferably, $X_1$ is CH or $CR_1$; $X_2$ is CH or $CR_2$; $X_3$ is N; and $X_4$ is N; and more preferably, $X_1$ is CH or $CR_1$; $X_2$ is $CR_2$; $X_3$ is N; and $X_4$ is N;

wherein $R_1$ is independently —Z—Y; preferably, $R_1$ is halo, trifluoromethyl, phenyl, methyl, hydroxymethyl, hydroxyethyl, dimethylamino, methoxy, trifluoromethoxy, —C(O)—$R_{20}$, —C(O)—$OR_{21}$, —C(O)—$NR_5R_{21}$, —S(O)$_2$—$R_{20}$ or —S(O)$_2$—$NR_5R_{21}$ radicals; and more preferably, $R_1$ is halo, trifluoromethyl, phenyl, methyl, hydroxymethyl, hydroxyethyl, dimethylamino, methoxy, trifluoromethoxy, acetyl, methoxycarbonyl, ethoxycarbonyl, amido, N,N-dimethylamido, methylsulfonyl or aminosulfonyl radicals; and $R_2$ is independently —Z—Y; and preferably, $R_2$ is independently Y; or alternatively, preferably, $X_1$ is CH or $CR_1$; $X_2$ is CH or $CR_2$; $X_3$ is CH or $CR_3$; and $X_4$ is CH or $CR_4$, provided that at least one of $X_1$, $X_2$, $X_3$ and $X_4$ is CH; more preferably, $X_1$ is CH; $X_2$ is CH; $X_3$ is CH or $CR_3$; and $X_4$ is CH or $CR_4$; and even more preferably, $X_1$ is CH; $X_2$ is CH; $X_3$ is $CR_3$; and $X_4$ is CH or $CR_4$;

wherein $R_1$ is independently —Z—Y; and preferably, $R_1$ is independently Y; and $R_2$ is independently —Z—Y; and preferably, $R_2$ is independently Y; and $R_3$ is independently —Z—Y; and preferably, $R_3$ is independently Y; and $R_4$ is independently —Z—Y; preferably, $R_4$ is halo, trifluoromethyl, phenyl, methyl, hydroxymethyl, hydroxyethyl, dimethylamino, methoxy, trifluoromethoxy, —C(O)—$R_{20}$, —C(O)—$OR_{21}$, —C(O)—$NR_5R_{21}$, —S(O)$_2$—$R_{20}$ or —S(O)$_2$—$NR_5R_{21}$ radicals; and more preferably, $R_4$ is halo, phenyl, trifluoromethyl, methyl, hydroxymethyl, hydroxyethyl, dimethylamino, methoxy, trifluoromethoxy, acetyl, methoxycarbonyl, ethoxycarbonyl, N,N-dimethylamido, amido, methylsulfonyl or aminosulfonyl radicals; or alternatively, more preferably, $X_1$ is CH; $X_2$ is CH or $CR_2$; $X_3$ is CH or $CR_3$; and $X_4$ is CH; and even more preferably, $X_1$ is CH; $X_2$ is $CR_2$; $X_3$ is CH or $CR_3$; and $X_4$ is CH;

wherein $R_2$ is independently —Z—Y; and preferably, $R_2$ is independently Y; and $R_3$ is independently —Z—Y; preferably, $R_3$ is halo, trifluoromethyl, phenyl, methyl, hydroxymethyl, hydroxyethyl, dimethylamino, methoxy, trifluoromethoxy, —C(O)—$R_{20}$, —C(O)—$OR_{21}$, —C(O)—$NR_5R_{21}$, —S(O)$_2$—$R_{20}$ or —S(O)$_2$—$NR_5R_{21}$ radicals; and more preferably, $R_3$ is halo, trifluoromethyl, phenyl, methyl, hydroxymethyl, hydroxyethyl, dimethylamino, methoxy, trifluoromethoxy, acetyl, methoxycarbonyl, ethoxycarbonyl, amido, N,N-dimethylamido, methylsulfonyl or aminosulfonyl radicals; and provided that (1) $R_2$ and $R_4$ are not both substituted or unsubstituted amino radicals; (2) the total number of aryl, heteroaryl, cycloalkyl and heterocyclyl radicals in each —Z—Y is 0–3; and (3) the combined total number of aryl, heteroaryl, cycloalkyl and heterocyclyl radicals in $R_1$, $R_2$, $R_3$ and $R_4$ is 0–4, preferably 0–3;

each Z is independently a (1) bond; (2) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio, cyano or halo, and (b) 1–2 radicals of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl; (3) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (4) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

preferably, each Z is independently a (1) bond; (2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, or heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals; (3) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoyl amino, ($C_1$–$C_4$ alkoxy)carbonylamino, $C_1$–$C_4$ alkylsulfonyl amino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each Z is independently a (1) bond; (2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, or heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonyl amino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals; (3) heterocyclyl radical optionally substituted by 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals; even more preferably, each Z is independently a (1) bond; (2) $C_1$–$C_8$ alkyl or $C_2$–$C_8$ alkenyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, halo, or heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals; (3) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl radicals; or (4) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

yet more preferably, each Z is independently a (1) bond; (2) $C_1$–$C_4$ alkyl or $C_2$–$C_5$ alkenyl radical optionally substituted by 1–3 radicals of amino, di-($C_1$–$C_2$ alkyl) amino, $C_1$–$C_5$ alkanoylamino, ($C_1$–$C_4$ alkoxy)carbonyl amino, hydroxy, $C_1$–$C_2$ alkoxy, $C_1$–$C_2$ alkylthio, halo, or heterocyclyl, aryl or heteroaryl optionally substituted by 1–3 radicals of amino, $C_1$–$C_4$ alkylamino, di-($C_1$–$C_2$ alkyl)amino, $C_1$–$C_5$ alkanoylamino, ($C_1$–$C_4$ alkoxy)carbonyl amino, hydroxy, $C_1$–$C_4$ alkoxy, $C_1$–$C_4$ alkylthio, cyano, halo, $C_1$–$C_4$ alkyl or trifluoromethyl radicals; (3) heterocyclyl radical optionally substituted by 1–2 radicals of amino, di-($C_1$–$C_2$ alkyl)amino, ($C_1$–$C_4$ alkoxy) carbonylamino, hydroxy, $C_1$–$C_2$ alkoxy, $C_1$–$C_2$ alkylthio or $C_1$–$C_4$ alkyl radicals; or (4) aryl or heteroaryl radical optionally substituted by 1–3 radicals of amino, di-($C_1$–$C_2$ alkyl)amino, $C_1$–$C_5$ alkanoylamino, ($C_1$–$C_4$ alkoxy)carbonyl amino, hydroxy, $C_1$–$C_2$ alkoxy, $C_1$–$C_2$ alkylthio, cyano, halo, $C_1$–$C_4$ alkyl or trifluoromethyl radicals;

yet even more preferably, each Z is independently a (1) bond; (2) $C_1$–$C_4$ alkyl or $C_2$–$C_5$ alkenyl radical optionally substituted by 1–3 radicals of amino, di-($C_1$–$C_2$ alkyl) amino, ($C_1$–$C_4$ alkoxy)carbonylamino, hydroxy, $C_1$–$C_2$ alkoxy, $C_1$–$C_2$ alkylthio, halo, or aryl or heteroaryl optionally substituted by 1–2 radicals of amino, di-($C_1$–$C_2$ alkyl) amino, acetamido, ($C_1$–$C_4$ alkoxy) carbonylamino, hydroxy, $C_1$–$C_2$ alkoxy, $C_1$–$C_2$ alkylthio, cyano, halo, $C_1$–$C_4$ alkyl or trifluoromethyl radicals; or (3) aryl or heteroaryl radical optionally substituted by 1–3 radicals of amino, di-($C_1$–$C_2$ alkyl) amino, acetamido, ($C_1$–$C_4$ alkoxy)carbonyl amino, hydroxy, $C_1$–$C_2$ alkoxy, $C_1$–$C_2$ alkylthio, cyano, halo, $C_1$–$C_4$ alkyl or trifluoromethyl radicals;

still more preferably, each Z is independently a (1) bond; or (2) $C_1$–$C_4$ alkyl radical optionally substituted by 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkyl thio, halo, or aryl or heteroaryl optionally substituted by 1–2 radicals of hydroxy, $C_1$–$C_2$ alkoxy, $C_1$–$C_2$ alkylthio, cyano, halo, $C_1$–$C_4$ alkyl or trifluoromethyl radicals; still even more preferably, each Z is independently a (1) bond; or (2) $C_1$–$C_4$ alkyl radical optionally substituted by 1–2 radicals of amino, t-butoxy carbonylamino, dimethylamino, hydroxy, methoxy, methylthio or halo radicals; and most preferably, each Z is a bond;

each Y is independently a hydrogen radical, provided Z is other than a bond; or halo, cyano, nitro, —C(O)—$R_{20}$, —C(O)—$OR_{21}$, —C(O)—$NR_5R_{21}$, —C($NR_5$)— $NR_5R_{21}$, —$OR_{21}$, —O—C(O)—$R_{21}$, —O—C(O)— $NR_5R_{21}$, —O—C(O)—$NR_{22}$—S(O)$_2$—$R_{20}$, —$SR_{21}$, —S(O)—$R_{20}$, —S(O)$_2$—$R_{20}$, —S(O)$_2$—$NR_5R_{21}$, —S(O)$_2$—$NR_{22}$—C(O)—$R_{21}$, —S(O)$_2$—$NR_{22}$—C (O)—$OR_{20}$, —S(O)$_2$—$NR_{22}$—C(O)—$NR_5R_{21}$, —$NR_5R_{21}$, —$NR_{22}$—C(O)—$R_{21}$, —$NR_{22}$—C(O)— $OR_{20}$, —$NR_{22}$—C(O)—$NR_5R_{21}$, —$NR_{22}$—C($NR_5$)— $NR_5R_{21}$, —$NR_{22}$—S(O)$_2$—$R_{20}$ or —$NR_{22}$—S(O)$_2$— $NR_5R_{21}$ radical;

preferably, each Y is independently a hydrogen radical, provided Z is other than a bond; or halo, —C(O)—$R_{20}$, —C(O)—$OR_{21}$, —C(O)—$NR_5R_{21}$, —C($NR_5$)— $NR_5R_{21}$, —$OR_{21}$, —O—C(O)—$R_{21}$, —O—C(O)— $NR_5R_{21}$, —$SR_{21}$, —S(O)—$R_{20}$, —S(O)$_2$—$R_{20}$, —S(O)$_2$—$NR_5R_{21}$, —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

more preferably, each Y is independently a hydrogen radical, provided Z is other than a bond; or halo, —C(O)—$R_{20}$, —C(O)—$OR_{21}$, —C(O)—$NR_5R_{21}$, —$OR_{21}$, —$SR_{21}$, —S(O)—$R_{20}$, —S(O)$_2$—$R_{20}$, —S(O)$_2$—$NR_5R_{21}$, —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—S(O)$_2$—$R_{20}$ or —$NR_{22}$—S(O)$_2$—$NR_5R_{21}$ radical;

even more preferably, each Y is independently a hydrogen radical, provided Z is other than a bond; or halo, —C(O)—$R_{20}$, —C(O)—$OR_{21}$, —C(O)—$NR_5R_{21}$, —$OR_{21}$, —$SR_{21}$, —S(O)—$R_{20}$, —S(O)$_2$—$R_{20}$, —S(O)$_2$—$NR_5R_{21}$, —$NR_5R_{21}$, —$NR_{22}$—C(O)—$R_{21}$, —$NR_{22}$—S(O)$_2$—$R_{20}$ or —$NR_{22}$—S(O)$_2$—$NR_5R_{21}$ radical;

yet even more preferably, each Y is independently a hydrogen radical, provided Z is other than a bond; or halo, —C(O)—$R_{20}$, —C(O)—$NR_5R_{21}$, —$OR_{21}$, —$SR_{21}$, —S(O)—$R_{20}$, —$NR_5R_{21}$, —$NR_{22}$—C(O)— $R_{21}$, —$NR_{22}$—S(O)$_2$—$R_{20}$ or —$NR_{22}$—S(O)$_2$—$NR_5R_{21}$ radical; and most preferably, each Y is independently a hydrogen radical, provided Z is other than a bond; or halo, —$NR_5R_{21}$, —$NR_{22}$—C(O)—$R_{21}$ or —$NR_{22}$—S(O)$_2$—$R_{20}$ radical;

wherein each $R_5$ is independently (1) hydrogen radicals; (2) alkyl, alkenyl or alkynyl radicals optionally substituted by 1–3 radicals of amino, alkylamino, dialkylamino, hydroxy, alkoxy, alkylthio, cyano or halo; or (3) aryl, heteroaryl, aralkyl, heteroaralkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, cyano, alkyl or haloalkyl; and preferably, each $R_5$ is independently (1) hydrogen radicals; (2) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano or halo; or (3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl) amino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_5$ is independently (1) hydrogen radicals; (2) $C_1$–$C_4$ alkyl, $C_2$–$C_5$ alkenyl or $C_2$–$C_5$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio or halo; or (3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl) amino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

even more preferably, each $R_5$ is independently (1) hydrogen radicals; (2) $C_1$–$C_4$ alkyl or $C_2$–$C_5$ alkenyl radicals optionally substituted by 1–3 radicals of amino, di-($C_1$–$C_4$-alkyl)amino, hydroxy, $C_1$–$C_4$ alkoxy, $C_1$–$C_4$ alkylthio or halo; or (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_4$-alkyl) amino, hydroxy, $C_1$–$C_4$ alkoxy, $C_1$–$C_4$ alkylthio, cyano, $C_{1-C4}$ alkyl or $C_1$–$C_2$ haloalkyl of 1–3 halo radicals;

yet even more preferably, each $R_5$ is independently (1) hydrogen radical; (2) $C_1$–$C_4$ alkyl radical optionally substituted by 1–3 radicals of amino, di-($C_{1-C2}$-alkyl) amino, hydroxy, $C_1$–$C_2$ alkoxy, $C_1$–$C_2$ alkylthio or halo; or (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_2$-alkyl)amino, hydroxy, $C_1$–$C_2$ alkoxy, $C_1$–$C_2$ alkylthio, methoxy, methylthio, cyano, $C_1$–$C_4$ alkyl or trifluoromethyl radicals;

still more preferably, each $R_5$ is independently (1) hydroqen radical; (2) $C_1$–$C_4$ alkyl radical optionally substituted by 1–3 halo radicals; or (3) phenyl-$C_1$–$C_2$-alkyl or heteroaryl-$C_1$–$C_2$-alkyl, radicals optionally substituted by 1–3 radicals of amino, dimethylamino, hydroxy, methoxy, methylthio, methyl or trifluoromethyl radicals; still even more preferably, each $R_5$ is independently hydrogen or $C_1$–$C_4$ alkyl radical; and most preferably, each $R_5$ is a hydrogen radical;

wherein each $R_{20}$ is independently (1) alkyl, alkenyl or alkynyl radicals optionally substituted by 1–3 radicals of —$CO_2R_{23}$, amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfonyl, alkylsulfonyl, cyano, halo or aralkoxy, aralkylthio, aralkylsulfonyl, cycloalkyl, heterocyclyl, aryl or heteroaryl radicals optionally substituted by 1–3 radicals of amino, alkylamino, dialkylamino, alkanoylamino, alkoxycarbonyl amino, alkylsulfonylamino, alkanoyl, alkoxycarbonyl, hydroxy, alkoxy, alkylthio, alkylsulfinyl, alkylsulfonyl, cyano, halo, alkyl or haloalkyl; (2) heterocyclyl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, alkyl or haloalkyl; or (3) aryl or heteroaryl radicals optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;

preferably, each $R_{20}$ is independently (1) $C_1$–$C_8$ alkyl, $C_2$–$C_8$ alkenyl or $C_2$–$C_8$ alkynyl radicals optionally substituted by 1–3 radicals of —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkyl sulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonyl amino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

more preferably, each $R_{20}$ is independently (1) $C_1$–$C_8$ alkyl, $C_2$–$C_5$ alkenyl or $C_2$–$C_5$ alkynyl radicals optionally substituted by 1–3 radicals of —$CO_2R_{23}$, amino, $C_1$–$C_4$ alkyl amino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkyl sulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkyl sulfonyl, cyano, halo, $C_1$–$C_4$ alkyl or $C_1$–$C_4$ haloalkyl of 1–3 halo radicals; (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

even more preferably, each $R_{20}$ is independently (1) $C_1$–$C_8$ alkyl or $C_2$–$C_5$ alkenyl radicals optionally substituted by 1–3 radicals of —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy) carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals; (2) heterocyclyl radical optionally substituted by 1–2 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, ($C_1$–$C_4$ alkoxy)carbonyl, hydroxy, $C_1$–$C_4$ alkoxy, $C_1$–$C_4$ alkylthio or $C_1$–$C_4$ alkyl; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoyl amino, ($C_1$–$C_4$ alkoxy)carbonylamino, $C_1$–$C_4$ alkylsulfonyl amino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_2$ haloalkyl of 1–3 halo radicals;

yet more preferably, each $R_{20}$ is independently (1) $C_1$–$C_8$ alkyl or $C_2$–$C_5$ alkenyl radicals optionally substituted by 1–3 radicals of —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy) carbonylamino, N-(($C_1$–$C_4$ alkoxy)carbonyl)-N-($C_1$–$C_4$ alkyl) amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, ($C_1$–$C_4$ alkoxy) carbonyl, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals; (2) heterocyclyl radical optionally substituted by 1–2 radicals of amino, di-($C_1$–$C_4$ alkyl)amino, ($C_1$–$C_4$ alkoxy) carbonylamino, ($C_1$–$C_4$ alkoxy)carbonyl, hydroxy, $C_1$–$C_4$ alkoxy, $C_1$–$C_4$ alkylthio or $C_1$–$C_4$ alkyl; or (3) aryl or heteroaryl radicals optionally substituted by 1–2 radicals of amino, di-($C_1$–$C_4$ alkyl)amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl radicals;

still more preferably, each $R_{20}$ is independently (1) $C_1$–$C_8$ alkyl radicals optionally substituted by 1–3 radicals of —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonyl amino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or $C_3$–$C_6$ cycloalkyl, heterocyclyl, aryl or heteroaryl radicals optionally substituted by 1–2 radicals of amino, di-($C_1$–$C_4$ alkyl)amino, $C_1$–$C_5$ alkanoylamino, ($C_1$–$C_4$ alkoxy)carbonyl amino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl or trifluoromethyl radicals; (2) heterocyclyl radical optionally substituted by 1–2 radicals of ($C_1$–$C_4$ alkoxy)carbonyl, hydroxy, $C_1$–$C_4$ alkoxy, $C_1$–$C_4$ alkylthio or $C_1$–$C_4$ alkyl; or (3) aryl or heteroaryl radicals optionally substituted by 1–2 radicals of ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl radicals;

still even more preferably, each $R_{20}$ is independently (1) $C_1$–$C_6$ alkyl radicals optionally substituted by 1–3 radicals of —$CO_2R_{23}$, amino, methylamino, dimethylamino, t-butoxycarbonylamino, N-((t-butoxy)carbonyl)-N-(methyl) amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals; (2) heterocyclyl radical optionally substituted by 1–2 radicals of t-butoxycarbonyl, hydroxy, or $C_1$–$C_4$ alkyl; or (3) aryl or heteroaryl radicals optionally substituted by 1–2 radicals of t-butoxycarbonyl, hydroxy, methoxy, methylthio, cyano, halo, azido, methyl or trifluoromethyl radicals; and most preferably, each $R_{20}$ is-independently (1) $C_1$–$C_6$ alkyl radicals optionally substituted by 1–3 radicals of —$CO_2R_{23}$, amino, methylamino, dimethylamino, t-butoxy carbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals; (2) heterocyclyl radical optionally substituted by t-butoxycarbonyl; or (3) aryl or heteroaryl radicals optionally substituted by 1–2 radicals of t-butoxy carbonyl, hydroxy, methoxy, halo, azido, methyl or trifluoromethyl radicals;

each $R_{21}$ is independently hydrogen radical or $R_{20}$;

each $R_{22}$ is independently (1) hydrogen radical; (2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or (3) heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; and preferably, each $R_{22}$ is independently (1) hydrogen radical; (2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkyl sulfonyl, cyano, halo, $C_1$–$C_4$ alkyl or $C_1$–$C_4$ haloalkyl of 1–3 halo radicals; or (3) heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

more preferably, each $R_{22}$ is independently (1) hydrogen radical; or (2) $C_1$–$C_4$ alkyl radical optionally substituted by a radical of phenyl or heteroaryl optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals; even more preferably, each $R_{22}$ is independently hydrogen or $C_1$–$C_4$ alkyl radical; and most preferably, each $R_{22}$ is independently hydrogen or methyl radical;

each $R_{23}$ is independently hydrogen or alkyl, or aryl, heteroaryl, aralkyl or heteroaralkyl optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; and preferably, each $R_{23}$ is independently hydrogen or $C_1$–$C_4$ alkyl, or aryl, heteroaryl, aryl-$C_1$–$C_4$-alkyl or heteroaryl-$C_1$–$C_4$-alkyl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

more preferably, each $R_{23}$ is independently hydrogen or $C_1$–$C_4$ alkyl, or phenyl, heteroaryl, phenyl-$C_1$–$C_2$-alkyl or heteroaryl-$C_1$–$C_2$-alkyl optionally substituted by 1–3 radicals of amino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

even more preferably, each $R_{23}$ is independently hydrogen or $C_1$–$C_4$ alkyl, or phenyl, heteroaryl, phenyl-$C_1$–$C_2$-alkyl or heteroaryl-$C_1$–$C_2$-alkyl optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;

yet more preferably, each $R_{23}$ is independently hydrogen or $C_1$–$C_4$ alkyl, or phenyl-$C_1$–$C_2$-alkyl or heteroaryl- $C_1$–$C_2$-alkyl optionally substituted by 1–3 radicals of amino, di-($C_1$–$C_2$ alkyl)amino, acetamido, ($C_1$–$C_4$ alkoxy)carbonyl amino, hydroxy, $C_1$–$C_2$ alkoxy, $C_1$–$C_2$ alkylthio, cyano, halo, $C_1$–$C_4$ alkyl or trifluoromethyl radicals; still more preferably, each $R_{23}$ is independently hydrogen or $C_1$–$C_4$ alkyl, or phenyl-$C_1$–$C_2$-alkyl optionally substituted by 1–2 radicals of hydroxy, $C_1$–$C_2$ alkoxy, $C_1$–$C_2$ alkylthio, cyano, halo, $C_1$–$C_4$ alkyl or trifluoromethyl radicals; and most preferably, each $R_{23}$ is independently hydrogen or $C_1$–$C_4$ alkyl radicals;

$R_{10}$ is a hydrogen, $R_{30}$, —C(O)—$R_{29}$, —C(O)—$OR_{30}$, —C(O)—$NR_{31}R_{32}$, —S(O)$_2$—$R_{30}$ or —S(O)$_2$—$NR_{31}R_{32}$ radical; preferably, $R_{10}$ is a hydrogen, $R_{30}$, —C(O)—$R_{29}$, —C(O)—$NR_{31}R_{32}$, —S(O)$_2$—$R_{30}$ or —S(O)$_2$—$NR_{31}R_{32}$ radical; more preferably, $R_{10}$ is a hydrogen, $R_{30}$, —C(O)—$R_{29}$ or —C(O)—$NR_{31}R_{32}$ radical; and most preferably, $R_{10}$ is a hydrogen or methyl radical;

$R_{11}$ and $R_{12}$ are each independently an aryl or heteroaryl radical optionally substituted by 1–3 radicals of $R_{30}$, halo, cyano, —C(O)—$R_{30}$, —C(O)—$OR_{29}$, —C(O)—$NR_{31}R_{32}$, —C($NR_{31}$)—$NR_{31}R_{32}$, —$OR_{29}$, —O—C(O)—$R_{29}$, —O—C(O)—$NR_{31}R_{32}$, —O—C(O)—$NR_{33}$—S(O)$_2$—$R_{30}$, —$SR_{29}$, —S(O)—$R_{30}$, —S(O)$_2$—$R_{30}$, —S(O)$_2$—$NR_{31}R_{32}$, —S(O)$_2$—$NR_{33}$—C(O)—$R_{30}$, —S(O)$_2$—$NR_{33}$—C(O)—$OR_{30}$, —S(O)$_2$—$NR_{33}$—C(O)—$NR_{31}R_{32}$, —$NR_{31}R_{32}$, —$NR_{33}$—C(O)—$R_{29}$, —$NR_{33}$—C(O)—$OR_{30}$, —$NR_{33}$—C(O)—$NR_{31}R_{32}$, —$NR_{33}$—C($NR_{31}$)—$NR_{31}R_{32}$, —$NR_{33}$—S(O)$_2$—$R_{30}$ or —$NR_{33}$—S(O)$_2$—$NR_{31}R_{32}$ radicals;

preferably, $R_{11}$ and $R_{12}$ are each independently an aryl or heteroaryl radical optionally substituted by 1–2 radicals of $R_{30}$, halo, cyano radicals, —C(O)—$R_{30}$, —C(O)—$OR_{29}$, —C(O)—$NR_{31}R_{32}$, —C($NR_{31}$)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$, —NR33—C(O)—$R_{29}$ or —$NR_{33}$—C(O)—$OR_{30}$ radicals;

more preferably, $R_{11}$ and $R_{12}$ are each independently an aryl or heteroaryl radical optionally substituted by 1–2 radicals of $R_{30}$, halo, cyano, —C(O)—$R_{30}$, —C(O)—$OR_{29}$, —C(O)—$NR_{31}R_{32}$, —C($NR_{31}$)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;

even more preferably, $R_{11}$ and $R_{12}$ are each independently an aryl or heteroaryl radical optionally substituted by 1–2 radicals of $R_{30}$, halo, cyano, —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;

yet more preferably, $R_{11}$ is a heteroaryl radical optionally substituted by 1–2 radicals of $R_{30}$, halo, cyano, —C(O)—$NR_{31}R_{32}$, —$OR_{29}$, —$SR_{29}$, —$NR_{31}R_{32}$ or —$NR_{33}$—C(O)—$R_{29}$ radicals; and $R_{12}$ is an aryl radical optionally substituted by 1–2 radicals of $R_{30}$, halo, cyano, —C(O)—$NR_{31}R_{32}$, —$OR_{29}$, —$SR_{29}$, —S(O)—$R_{30}$, S(O)$_2$—$R_{30}$, —S(O)$_2$—$NR_{31}R_{32}$, —$NR_{31}R_{32}$ or —$NR_{33}$—C(O)—$R_{29}$ radicals;

still more preferably, $R_{11}$ is a heteroaryl radical optionally substituted by 1–2 radicals of amino, dimethylamino, acetamido, hydroxy, halo, cyano, methoxy, methyl or trifluoromethyl radicals; and $R_{12}$ is an aryl radical optionally substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals;

still even more preferably, $R_{11}$ is a 4-pyridyl, 4-quinolinyl, 4-imidazolyl or 4-pyrimidinyl radical optionally substituted by a radical of amino, dimethylamino, acetamido, hydroxy, halo, cyano, methoxy, methyl or trifluoromethyl radicals; and $R_{12}$ is an unsubstituted phenyl or naphthyl radical or a phenyl radical substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals; and most preferably, $R_{11}$ is a 4-pyridyl radical optionally substituted by a radical of amino, dimethylamino, acetamido, hydroxy, halo, cyano, methoxy, methyl or trifluoromethyl radicals; and $R_{12}$ is an unsubstituted phenyl radical or a phenyl radical substituted by 1–2 radicals of amino, dimethylamino, acetamido, hydroxy, halo, cyano, methoxy, methylthio, methylsulfonyl, methyl or trifluoromethyl radicals; and provided that the total number of aryl, heteroaryl, cycloalkyl and heterocyclyl radicals substituted on each of $R_{11}$ and $R_{12}$ is 0–1; and provided that when each of $X_1$, $X_2$, $X_3$ and $X_4$ represent carbon atoms, then $R_{11}$ is a substituted aryl radical and $R_{12}$ is heteroaryl radical, or $R_{11}$ is a heteroaryl radical and $R_{12}$ is a substituted aryl radical;

wherein each $R_{30}$ is independently (1) alkyl, alkenyl or alkynyl radicals optionally substituted by 1–3 radicals of —$NR_{31}R_{31}$, —$CO_2R_{23}$, hydroxy, alkoxy, alkylthio, alkylsulfinyl, alkylsulfonyl, cyano, halo or aralkoxy, aralkylthio, aralkylsulfonyl, heterocyclyl, aryl or heteroaryl radicals optionally substituted by 1–3 radicals of amino, alkylamino, dialkylamino, alkanoyl amino, alkoxycarbonylamino, alkylsulfonylamino, hydroxy, alkoxy, alkylthio, alkylsulfinyl, alkylsulfonyl, cyano, halo, alkyl or haloalkyl; (2) heterocyclyl radical optionally substituted by 1–3 radicals of amino, alkylamino, dialkylamino, alkanoylamino, alkoxycarbonyl amino, alkylsulfonylamino, hydroxy, alkoxy, alkylthio, cyano, alkyl or haloalkyl; or (3) aryl or heteroaryl radicals optionally substituted by 1–3 radicals of amino, alkylamino, dialkylamino, alkanoylamino, alkoxycarbonyl amino, alkylsulfonylamino, hydroxy, alkoxy, alkylthio, cyano, halo, alkyl or haloalkyl;

preferably, each $R_{30}$ is independently (1) $C_1$–$C_4$ alkyl, $C_2$–$C_4$ alkenyl or $C_2$–$C_4$ alkynyl radicals optionally substituted by 1–3 radicals of —$NR_{31}R_{31}$, —$CO_2R_{23}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo or aryl-$C_1$–$C_4$-alkoxy, aryl-$C_1$–$C_4$-alkylthio, aryl-$C_1$–$C_4$-alkylsulfonyl, heterocyclyl, aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonyl amino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each $R_{30}$ is independently (1) $C_1$–$C_4$ alkyl radical optionally substituted by 1–3 radicals of (a) —$NR_{31}R_{31}$; (b) $C_1$–$C_4$ alkoxy-carbonyl or phenoxycarbonyl or phenylmethoxycarbonyl optionally substituted by 1–3 radicals of amino, alkylamino, di-($C_1$–$C_4$-alkyl)amino, $C_1$–$C_5$ alkanoylamino, ($C_1$–$C_4$ alkoxy)carbonylamino, $C_1$–$C_4$ alkyl sulfonylamino, hydroxy, $C_1$–$C_4$ alkoxy, $C_1$–$C_4$ alkylthio, cyano, halo, $C_1$–$C_4$ alkyl or trifluoromethyl; or (c) hydroxy, $C_1$–$C_4$ alkoxy, $C_1$–$C_4$ alkylthio, or phenyl-$C_1$–$C_4$-alkoxy, phenyl-$C_1$–$C_4$-alkylthio, heterocyclyl, phenyl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals; (2) $C_1$–$C_4$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl radicals;

even more preferably, each $R_{30}$ is independently (1) $C_1$–$C_4$ alkyl radical optionally substituted by (a) amino, $C_1$–$C_4$ alkylamino or di-($C_1$–$C_4$-alkyl)amino radicals; or (b) hydroxy, $C_1$–$C_4$ alkoxy, heterocyclyl, phenyl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl radicals; (2) $C_1$–$C_2$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl radicals;

yet more preferably, each $R_{30}$ is independently (1) $C_1$–$C_4$ alkyl radical optionally substituted by a phenyl or heteroaryl radical optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals; (2) trifluoromethyl radical; or (3) aryl or heteroaryl radicals optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

still more preferably, each $R_{30}$ is independently (1) $C_1$–$C_4$ alkyl radical optionally substituted by a phenyl or heteroaryl radical optionally substituted by 1–3 radicals of amino, dimethylamino, acetamido, hydroxy, halo, methoxy, methyl or trifluoromethyl radicals; (2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals; and most preferably, $R_{30}$ is independently (1) $C_1$–$C_4$ alkyl radical optionally substituted by a phenyl or heteroaryl radical optionally substituted by 1–2 radicals of amino, dimethylamino, acetamido, hydroxy, halo, methoxy, methyl or trifluoromethyl radicals; (2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

each $R_{29}$ is independently hydrogen radical or $R_{30}$; and preferably, $R_{29}$ is an aryl or heteroaryl radicals optionally substituted by 1–2 radicals of amino, dimethylamino, acetamido, hydroxy, halo, methoxy, methyl or trifluoromethyl radicals;

each $R_{31}$ is independently (1) hydrogen radicals; (2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{31}$ is independently (1) hydrogen radicals; (2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoyl amino, ($C_1$–$C_4$ alkoxy)carbonylamino, $C_1$–$C_4$ alkylsulfonyl amino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{31}$ is independently (1) hydrogen radicals; or (2) $C_1$–$C_4$ alkyl radical optionally substituted by an phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, $C_1$–$C_4$ alkyl or trifluoromethyl radicals; even more preferably, each $R_{31}$ is independently hydrogen or $C_1$–$C_4$ alkyl radicals; and most preferably, $R_{31}$ is independently hydrogen, methyl or ethyl radicals;

each $R_{32}$ is independently (1) hydrogen radicals; (2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{32}$ is independently (1) hydrogen radicals; (2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoyl amino, ($C_1$–$C_4$ alkoxy)carbonylamino, $C_1$–$C_4$ alkylsulfonyl amino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{32}$ is independently (1) hydrogen radicals; (2) $C_1$–$C_4$ alkyl radical optionally substituted by an $C_3$–$C_6$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoyl amino, ($C_1$–$C_4$ alkoxy)carbonylamino, $C_1$–$C_4$ alkylsulfonyl amino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_6$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

even more preferably, each $R_{32}$ is independently (1) hydrogen radicals; (2) $C_1$–$C_4$ alkyl radical optionally substituted by phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl radicals; or (3) phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl radicals;

yet more preferably, each $R_{32}$ is independently (1) hydrogen radicals; (2) $C_1$–$C_4$ alkyl radical or $C_1$–$C_2$ alkyl radical substituted by phenyl or heteroaryl radical optionally substituted by 1–3 radicals of amino, di-($C_1$–$C_2$ alkyl)amino, acetamido, hydroxy, $C_1$–$C_2$ alkoxy, $C_1$–$C_4$ alkyl or trifluoromethyl radicals; or (3) phenyl or heteroaryl radical optionally substituted by 1–3 radicals of amino, di-($C_1$–$C_2$ alkyl)amino, acetamido, hydroxy, $C_1$–$C_2$ alkoxy, $C_1$–$C_4$ alkyl or trifluoromethyl radicals;

still more preferably, each $R_{32}$ is independently (1) hydrogen radicals; (2) $C_1$–$C_4$ alkyl radical or $C_1$–$C_2$ alkyl radical substituted by phenyl or heteroaryl radical optionally substituted by 1–3 radicals of amino, dimethylamino, acetamido, hydroxy, methoxy, methyl or trifluoromethyl radicals; or (3) phenyl or heteroaryl radical optionally substituted by 1–3 radicals of amino, dimethylamino, acetamido, hydroxy, methoxy, methyl or trifluoromethyl radicals; and most preferably, each $R_{32}$ is independently (1) hydrogen or $C_1$–$C_4$ alkyl radical; or (2) phenyl or heteroaryl radical optionally substituted by 1–2 radicals of amino, dimethylamino, acetamido, hydroxy, methoxy, methyl or trifluoromethyl radicals; and each $R_{33}$ is independently (1) hydrogen radical; or (2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; preferably, each $R_{33}$ is independently (1) hydrogen radical; or (2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; more preferably, each $R_{33}$ is independently hydrogen or $C_1$–$C_4$ alkyl radical; and most preferably, each $R_{33}$ is independently hydrogen or methyl radical.

Compounds of interest include the following:

3-(4-pyridyl)-2-(4-fluorophenyl)indole;

3-(4-fluorophenyl)-2-(4-pyridyl)indole;

6-amino-3-(4-pyridyl)-2-(4-fluorophenyl)-7-aza-indole;

6-amino-3-(4-fluorophenyl)-2-(4-pyridyl)-7-aza-indole;

6-(4'-t-butoxycarbonylamino-1'-oxo-butylamino)-3-(4-pyridyl)-2-(4-fluorophenyl)-7-aza-indole;

6-(4'-amino-1'-oxo-butylamino)-3-(4-pyridyl)-2-(4-fluorophenyl)-7-aza-indole;

6-(5'-ureido-1'-oxo-2'-t-butoxycarbonylaminopentyl amino)-3-(4-pyridyl)-2-(4-fluorophenyl)-7-aza-indole;

6-(5'-ureido-1'-oxo-2'-aminopentylamino)-3-(4-pyridyl)-2-(4-fluorophenyl)-7-aza-indole;

6-(6'-t-butoxycarbonylamino-1'-oxo-2'-t-butoxycarbonyl aminohexylamino)-3-(4-pyridyl)-2-(4-fluorophenyl)-7-aza-indole; 6-(6'-amino-1'-oxo-2'-aminohexylamino)-3-(4-pyridyl)-2-(4-fluorophenyl)-7-aza-indole;

6-(5'-t-butoxycarbonylamino-1'-oxo-2'-t-butoxycarbonyl aminopentylamino)-3-(4-pyridyl)-2-(4-fluorophenyl)-7-aza-indole;

6-(5'-amino-1'-oxo-2'-aminopentylamino)-3-(4-pyridyl)-2-(4-fluorophenyl)-7-aza-indole;

6-(3'-(4-iodophenyl)-1'-oxo-2'-t-butoxycarbonylamino propylamino)-3-(4-pyridyl)-2-(4-fluorophenyl)-7-aza-indole;

6-(3'-(4-iodophenyl)-1'-oxo-2'-aminopropylamino)-3-(4-pyridyl)-2-(4-fluorophenyl)-7-aza-indole;

6-(3'-methyl-1'-oxo-2'-t-butoxycarbonylaminobutylamino)-3-(4-pyridyl)-2-(4-fluorophenyl)-7-aza-indole;

6-(3'-methyl-1'-oxo-2'-aminobutylamino)-3-(4-pyridyl)-2-(4-fluorophenyl)-7-aza-indole;

6-(3'-dimethyl-1'-oxo-2'-t-butoxycarbonylamino pentylamino)-3-(4-pyridyl)-2-(4-fluorophenyl)-7-aza-indole;

6-(4',4'-dimethyl-1'-oxo-2'-aminopentylamino)-3-(4-pyridyl)-2-(4-fluorophenyl)-7-aza-indole;

6-(5'-t-butoxycarbonylamino-1'-oxo-pentylamino)-3-(4-pyridyl)-2-(4-fluorophenyl)-7-aza-indole;

6-(5'-amino-1'-oxo-pentylamino)-3-(4-pyridyl)-2-(4-fluorophenyl)-7-aza-indole;

6-(6'-t-butoxycarbonylamino-1'-oxo-hexylamino)-3-(4-pyridyl)-2-(4-fluorophenyl)-7-aza-indole;

6-(6'-amino-1'-oxo-hexylamino)-3-(4-pyridyl)-2-(4-fluorophenyl)-7-aza-indole;

6-(3'-cyclohexyl-1'-oxo-2'-t-butoxycarbonylaminopropyl amino)-3-(4-pyridyl)-2-(4-fluorophenyl)-7-aza-indole;

6-(3'-cyclohexyl-1'-oxo-2'-aminopropylamino)-3-(4-pyridyl)-2-(4-fluorophenyl)-7-aza-indole;

6-(4'-t-butoxycarbonyl-1'-oxo-2'-t-butoxycarbonylamino butylamino)-3-(4-pyridyl)-2-(4-fluorophenyl)-7-aza-indole;

6-(4'-carboxy-1'-oxo-2'-aminobutylamino)-3-(4-pyridyl)-2-(4-fluorophenyl)-7-aza-indole;

6-(3'-O-t-butoxy-1'-oxo-2'-t-butoxycarbonylaminobutyl amino)-3-(4-pyridyl)-2-(4-fluorophenyl)-7-aza-indole;

6-(3'-hydroxy-1'-oxo-2'-aminobutylamino)-3-(4-pyridyl)-2-(4-fluorophenyl)-7-aza-indole;
6-(3'-phenyl-1'-oxo-2'-t-butoxycarbonylaminopropyl amino)-3-(4-pyridyl)-2-(4-fluorophenyl)-7-aza-indole;
6-(3'-phenyl-1'-oxo-2'-D,L-aminopropylamino)-3-(4-pyridyl)-2-(4-fluorophenyl)-7-aza-indole;
6-(3'-(4-t-butoxyphenyl)-1'-oxo-2'-t-butoxycarbonylamino propylamino)-3-(4-pyridyl)-2-(4-fluorophenyl)-7-aza-indole;
6-(3'-(4-hydroxyphenyl)-1'-oxo-2'-aminopropylamino)-3-(4-pyridyl)-2-(4-fluorophenyl)-7-aza-indole;
6-(3'-t-butoxycarbonylamino-1'-oxo-propylamino)-3-(4-pyridyl)-2-(4-fluorophenyl)-7-aza-indole;
6-(3'-amino-1'-oxo-propylamino)-3-(4-pyridyl)-2-(4-fluorophenyl)-7-aza-indole;
6-(2'-t-butoxycarbonylamino-1'-oxo-ethylamino)-3-(4-pyridyl)-2-(4-fluorophenyl)-7-aza-indole;
6-(2'-amino-1'-oxo-ethylamino)-3-(4-pyridyl)-2-(4-fluorophenyl)-7-aza-indole;
6-(methylsulfonylamino)-3-(4-pyridyl)-2-(4-fluorophenyl)-7-aza-indole;
6-(1'-oxo-ethylamino)-3-(4-pyridyl)-2-(4-fluorophenyl)-7-aza-indole;
6-(2'-(5-chlorothienyl)sulfonylamino)-3-(4-pyridyl)-2-(4-fluorophenyl)-7-aza-indole;
6-(phenylsulfonylamino)-3-(4-pyridyl)-2-(4-fluorophenyl)-7-aza-indole;
6-(2'-N-phthaloyl-1'-oxo-ethylamino)-3-(4-pyridyl)-2-(4-fluorophenyl)-7-aza-indole;
6-(3'-N-phthaloyl-1'-oxo-propylamino)-3-(4-pyridyl)-2-(4-fluorophenyl)-7-aza-indole;
3-(4-pyridyl)-2-(4-fluorophenyl)-4,7-diaza-indole;
6-(2'-N-t-butoxycarbonyl-L-prolylamino)-3-(4-pyridyl)-2-(4-fluorophenyl)-7-aza-indole;
6-(2'-L-prolylamino)-3-(4-pyridyl)-2-(4-fluorophenyl)-7-aza-indole;
6-(2S'-dimethylamino-1'-oxo-propylamino)-3-(4-pyridyl)-2-(4-fluorophenyl)-7-aza-indole;
6-(2'-dimethylamino-1'-oxo-ethylamino)-3-(4-pyridyl)-2-(4-fluorophenyl)-7-aza-indole;
6-(2'-N-methyl-t-butoxycarbonylamino-1'-oxo-ethylamino)-3-(4-pyridyl)-2-(4-fluorophenyl)-7-aza-indole;
6-(2'-N-methyl-amino-1'-oxo-ethylamino)-3-(4-pyridyl)-2-(4-fluorophenyl)-7-aza-indole;
6-(4'-N-t-butoxycarbonylisonipecotylamino)-3-(4-pyridyl)-2-(4-fluorophenyl)-7-aza-indole;
6-(4'-isonipecotylamino)-3-(4-pyridyl)-2-(4-fluorophenyl)-7-aza-indole;
6-(4'-methylsulfoxo-1'-oxo-2'S-t-butoxycarbonylamino butylamino)-3-(4-pyridyl)-2-(4-fluorophenyl)-7-aza-indole;
6-(4'-methylsulfoxo-1'-oxo-2'S-aminobutylamino)-3-(4-pyridyl)-2-(4-fluorophenyl)-7-aza-indole;
6-(3'-(3-pyridyl)-1'-oxo-2'S-t-butoxycarbonylaminopropyl amino)-3-(4-pyridyl)-2-(4-fluorophenyl)-7-aza-indole;
6-(3'-(3-pyridyl)-1'-oxo-2'S-aminopropylamino)-3-(4-pyridyl)-2-(4-fluorophenyl)-7-aza-indole;
6-(N,N-Di-t-butoxycarbonyl-L-histidinylamino)-3-(4-pyridyl)-2-(4-fluorophenyl)-7-aza-indole;
6-(L-histidinylamino)-3-(4-pyridyl)-2-(4-fluorophenyl)-7-aza-indole;
6-(N-t-butoxycarbonyl-3(S) 1',2',3',4'-tetrahydro-3'-isoquinolinyloxo-amino)-3-(4-pyridyl)-2-(4-fluorophenyl)-7-aza-indole;
6-(3(S) 1',2',3',4'-tetrahydro-3'-isoquinolinyloxo amino)-3-(4-pyridyl)-2-(4-fluorophenyl)-7-aza-indole;
6-(2'-phenyl-1'-oxo-2'R-N-t-butoxycarbonylaminoethyl amino)-3-(4-pyridyl)-2-(4-fluorophenyl)-7-aza-indole;
6-(2'-phenyl-1'-oxo-2'R-aminoethylamino)-3-(4-pyridyl)-2-(4-fluorophenyl)-7-aza-indole;
6-(2'-phenyl-1'-oxo-2'S-N-t-butoxycarbonylaminoethyl amino)-3-(4-pyridyl)-2-(4-fluorophenyl)-7-aza-indole;
6-(2'-phenyl-1'-oxo-2'S-aminoethylamino)-3-(4-pyridyl)-2-(4-fluorophenyl)-7-aza-indole;
6-(2'-phenyl-1'-oxo-2'R-N-t-butoxycarbonyl-N-methylamino ethylamino)-3-(4-pyridyl)-2-(4-fluorophenyl)-7-aza-indole;
6-(2'-phenyl-1'-oxo-2'R-N-methylaminoethylamino)-3-(4-pyridyl)-2-(4-fluorophenyl)-7-aza-indole;
6-(1'-oxo-2'S-t-butoxycarbonylaminopropylamino)-3-(4-pyridyl)-2-(4-fluorophenyl)-7-aza-indole;
6-(1'-oxo-2'S-aminopropylamino)-3-(4-pyridyl)-2-(4-fluorophenyl)-7-aza-indole;
6-(3'-phenyl-1'-oxo-2'-(L)-t-butoxycarbonylaminopropyl amino)-3-(4-pyridyl)-2-(4-fluorophenyl)-7-aza-indole;
6-(3'-phenyl-1'-oxo-2'-(L)-aminopropylamino)-3-(4-pyridyl)-2-(4-fluorophenyl)-7-aza-indole;
6-(1'-oxo-2'S-t-butoxycarbonyl-N-methylaminopropyl amino)-3-(4-pyridyl)-2-(4-fluorophenyl)-7-aza-indole;
6-(1'-oxo-2'S-N-methylaminopropylamino)-3-(4-pyridyl)-2-(4-fluorophenyl)-7-aza-indole;
6-(1'-oxo-2'S-t-butoxycarbonyl-N-methyl-4-methyl-2-amino pentyl-amino)-3-(4-pyridyl)-2-(4-fluorophenyl)-7-aza-indole;
6-(1'-oxo-2'S-N-methyl-4-methyl-2-aminopentylamino)-3-(4-pyridyl)-2-(4-fluorophenyl)-7-aza-indole;
6-(1'-oxo-2'R-t-butoxycarbonylaminopropylamino)-3-(4-pyridyl)-2-(4-fluorophenyl)-7-aza-indole;
6-(1'-oxo-2'R-aminopropylamino)-3-(4-pyridyl)-2-(4-fluorophenyl)-7-aza-indole;
6-(3'-(2-thienyl)-1'-oxo-2'-(L)-t-butoxycarbonylamino propylamino)-3-(4-pyridyl)-2-(4-fluorophenyl)-7-aza-indole;
6-(3'-(2-thienyl)-1'-oxo-2'-(L)-aminopropylamino)-3-(4-pyridyl)-2-(4-fluorophenyl)-7-aza-indole;
6-(3'-(4-azidophenyl)-1'-oxo-2'S-t-butoxycarbonylamino propylamino)-3-(4-pyridyl)-2-(4-fluorophenyl)-7-aza-indole;
6-(3'-(4-azidophenyl)-1'-oxo-2'S-aminopropylamino)-3-(4-pyridyl)-2-(4-fluorophenyl)-7-aza-indole;
6-(3'-(3-benzothienyl)-1'-oxo-2'S-t-butoxycarbonylamino propylamino)-3-(4-pyridyl)-2-(4-fluorophenyl)-7-aza-indole;
6-(3'-(3-benzothienyl)-1'-oxo-2'S-aminopropylamino)-3-(4-pyridyl)-2-(4-fluorophenyl)-7-aza-indole;
6-(4'-phenyl-1'-oxo-2'-(L)-t-butoxycarbonylaminobutyl amino)-3-(4-pyridyl)-2-(4-fluorophenyl)-7-aza-indole;
6-(4'-phenyl-1'-oxo-2'-(L)-aminobutylamino)-3-(4-pyridyl)-2-(4-fluorophenyl)-7-aza-indole;
6-(4'-phenyl-1'-oxo-2'-(D)-t-butoxycarbonylaminobutyl amino)-3-(4-pyridyl)-2-(4-fluorophenyl)-7-aza-indole;
6-(4'-phenyl-1'-oxo-2'-(D)-aminobutylamino)-3-(4-pyridyl)-2-(4-fluorophenyl)-7-aza-indole;

6-(2'-amino-1'-oxo-ethylamino)-3-(4-pyridyl)-2-(4-fluorophenyl)-1-isobutoxycarbonyl-7-aza-indole;

6-(phenylmethylamino)-3-(4-pyridyl)-2-(4-fluorophenyl)-7-aza-indole;

6-(diethylamino)-3-(4-pyridyl)-2-(4-fluorophenyl)-7-aza-indole;

6-(3'-phenylpropylamino)-3-(4-pyridyl)-2-(4-fluorophenyl)-7-aza-indole;

6-(2'(R,S)-phenylpropylamino)-3-(4-pyridyl)-2-(4-fluorophenyl)-7-aza-indole;

6-(2'(R,S)-ethylhexylamino)-3-(4-pyridyl)-2-(4-fluorophenyl)-7-aza-indole;

6-Amino-5-chloro-3-(4-pyridyl)-2-(4-fluorophenyl)-7-aza-indole;

6-Amino-5-fluoro-3-(4-pyridyl)-2-(4-fluorophenyl)-7-aza-indole;

6-Amino-5-bromo-3-(4-pyridyl)-2-(4-fluorophenyl)-7-aza-indole;

6-(di-isoamylamino)-3-(4-pyridyl)-2-(4-fluorophenyl)-7-aza-indole;

6-(2',2'-dimethylpropylamino)-3-(4-pyridyl)-2-(4-fluorophenyl)-7-aza-indole;

6-(isoamylamino)-3-(4-pyridyl)-2-(4-fluorophenyl)-7-aza-indole;

6-(2'-ethylbutylamino)-3-(4-pyridyl)-2-(4-fluorophenyl)-7-aza-indole;

6-(2'-thienylmethylamino)-3-(4-pyridyl)-2-(4-fluorophenyl)-7-aza-indole;

6-(3',3'di-phenylpropylamino)-3-(4-pyridyl)-2-(4-fluorophenyl)-7-aza-indole;

6-(ethylamino)-3-(4-pyridyl)-2-(4-fluorophenyl)-7-aza-indole;

6-(3'-phenyl-1'-oxo-2'-(R,S)-methylpropylamino)-3-(4-pyridyl)-2-(4-fluorophenyl)-7-aza-indole;

6-(2'-amino-1'-oxo-ethylamino)-3-(4-pyridyl)-2-(4-fluorophenyl)-1-methyl-7-aza-indole;

6-(3',3'-dimethyl-1-oxo-butylamino)-3-(4-pyridyl)-2-(4-fluorophenyl)-7-aza-indole;

6-(ethoxycarbonylamino)-3-(4-pyridyl)-2-(4-fluorophenyl)-7-aza-indole;

6-(2'S-amino-1'-oxo-propylamino)-3-(4-pyridyl)-2-(4-fluorophenyl)-1-methyl-7-aza-indole;

6-(2'S-amino-1'-oxo-propylamino)-3-(4-pyridyl)-2-(4-fluorophenyl)-1-isobutyl-7-aza-indole; and 6-(2'S-amino-1'-oxo-propylamino)-3-(4-pyridyl)-2-(4-fluorophenyl)-1-cyclohexylmethyl-7-aza-indole.

As utilized herein, the following terms shall have the following meanings:

"Alkyl", alone or in combination, means a straight-chain or branched-chain alkyl radical containing preferably 1–15 carbon atoms ($C_1$–$C_5$), more preferably 1–8 carbon atoms ($C_1$–$C_8$), even more preferably 1–6 carbon atoms ($C_1$–$C_6$), yet more preferably 1–4 carbon atoms ($C_1$–$C_4$), still more preferably 1–3 carbon atoms ($C_1$–$C_3$), and most preferably 1–2 carbon atoms ($C_1$–$C_2$). Examples of such radicals include methyl, ethyl, n-propyl, isopropyl, n-butyl, isobutyl, sec-butyl, tert-butyl, pentyl, iso-amyl, hexyl, octyl and the like.

"Hydroxyalkyl", alone or in combination, means an alkyl radical as defined above wherein at least one hydrogen radical is replaced with a hydroxyl radical, preferably 1–3 hydrogen radicals are replaced by hydroxyl radicals, more preferably 1–2 hydrogen radicals are replaced by hydroxyl radicals, and most preferably one hydrogen radical is replaced by a hydroxyl radical. Examples of such radicals include hydroxymethyl, 1-, 2-hydroxyethyl, 1-, 2-, 3-hydroxypropyl, 1,3-dihydroxy-2-propyl, 1,3-dihydroxybutyl, 1,2,3,4,5,6-hexahydroxy-2-hexyl and the like.

"Alkenyl", alone or in combination, means a straight-chain or branched-chain hydrocarbon radical having one or more double bonds, preferably 1–2 double bonds and more preferably one double bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkenyl radicals include ethenyl, propenyl, 2-methylpropenyl, 1,4-butadienyl and the like.

"Alkynyl", alone or in combination, means a straight-chain or branched chain hydrocarbon radical having one or more triple bonds, preferably 1–2 triple bonds and more preferably one triple bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkynyl radicals include ethynyl, propynyl (propargyl), butynyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as defined above and "C(O)" is a carbonyl radical.

"Alkoxycarbonylamino", alone or in combination, means a radical of the type "R—O—C(O)—NH—" wherein "R—O—C(O)" is an alkoxycarbonyl radical as defined above, wherein the amino radical may optionally be substituted, such as with alkyl, aryl, aralkyl, cycloalkyl, cycloalkylalkyl and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio and the like.

"Alkylsulfinyl", alone or in combination, means a radical of the type "R—S(O)—" wherein "R" is an alkyl radical as defined above and "S(O)" is a mono-oxygenated sulfur atom. Examples of such alkylsulfinyl radicals include methylsulfinyl, ethylsulfinyl, n-propylsulfinyl, isopropylsulfinyl, n-butylsulfinyl, iso-butylsulfinyl, sec-butylsulfinyl, tert-butylsulfinyl and the like.

"Alkylsulfonyl", alone or in combination, means a radical of the type "R—S(O)$_2$—" wherein "R" is an alkyl radical as defined above and "S(O)$_2$—" is a di-oxygenated sulfur atom. Examples of such alkylsulfonyl radicals include methylsulfonyl, ethylsulfonyl, n-propylsulfonyl, isopropylsulfonyl, n-butylsulfonyl, iso-butylsulfonyl, sec-butylsulfonyl, tert-butylsulfonyl and the like.

"Alkylsulfonylamino", alone or in combination, means a radical of the type "R—S(O)$_2$—NH—" wherein "R—S(O)$_2$—" is an alkylsulfonyl radical as defined above, wherein the amino radical may optionally be substituted, such as with alkyl, aryl, aralkyl, cycloalkyl, cycloalkylalkyl and the like.

"Aryl", alone or in combination, means a phenyl or naphthyl radical which is optionally substituted with one or more substituents selected from alkyl, alkoxy, halogen, hydroxy, amino, azido, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamido, N,N-dialkylamido, aralkoxycarbonylamino, alkylthio, alkylsulfinyl, alkylsulfonyl and the like. Examples of aryl radicals are phenyl, p-tolyl, 4-methoxyphenyl, 4-(tert-butoxy)phenyl, 3-methyl-4-methoxyphenyl, 4-$CF_3$-phenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like.

"Aralkyl", alone or in combination, means an alkyl radical as defined above in which at least one hydrogen atom, preferably 1–2, is replaced by an aryl radical as defined above, such as benzyl, 1-, 2-phenylethyl, dibenzylmethyl, hydroxyphenylmethyl, methylphenylmethyl, diphenylmethyl, dichlorophenylmethyl, 4-methoxyphenylmethyl and the like.

"Aralkoxy", alone or in combination, means an alkoxy radical as defined above in which at least one hydrogen atom, preferably 1–2, is replaced by an aryl radical as defined above,. such as benzyloxy, 1-, 2-phenylethoxy, dibenzylmethoxy, hydroxyphenylmethoxy, methylphenylmethoxy, dichlorophenylmethoxy, 4-methoxyphenylmethoxy and the like.

"Aralkoxycarbonyl", alone or in combination, means a radical of the type "R—O—C(O)—" wherein "R—O—" is an aralkoxy radical as defined above and "—C(O)—" is a carbonyl radical.

"Aryloxyl", alone or in combination, means a radical of the type "R—O—" wherein "R" is an aryl radical as defined above.

"Alkanoyl", alone or in combination, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

"Alkanoylamino", alone or in combination, means a radical of the type "R—C(O)—NH—" wherein "R—C(O)—" is an alkanoyl radical as defined above, wherein the amino radical may optionally be substituted, such as with alkyl, aryl, aralkyl, cycloalkyl, cycloalkylalkyl and the like.

"Aminocarbonyl", alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. "Aminocarbonylamino", alone or in combination, means an amino substituted carbonyl substituted on a second amino (ureido) radical, wherein each amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Aminoalkanoyl", alone or in combination, means an alkanoyl radical as defined above derived in which at least one, preferably 1–2, hydrogen atom is replaced by an amino radical, wherein each amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Benzo", alone or in combination, means the divalent radical $C_6H_4=$ derived from benzene.

"Bicyclic" as used herein is intended to include both fused ring systems, such as naphthyl and β-carbolinyl, and substituted ring systems, such as biphenyl, phenylpyridyl, naphthyl and diphenylpiperazinyl.

"Cycloalkyl", alone or in combination, means a saturated or partially saturated, preferably one double bond, monocyclic or bicyclic alkyl radical, preferably monocyclic, containing preferably 3–10 carbon atoms ($C_3$–$C_{10}$) more preferably 3–8 carbon atoms ($C_3$–$C_8$), even more preferably 3–6 carbon atoms ($C_3$–$C_6$), which is optionally be benzo fused and which is optionally substituted as defined herein with respect to the definition of aryl. Examples of such cycloalkyl radicals include cyclopropyl, cyclobutyl, cyclopentyl, cyclohexyl, dihydroxycyclohexyl, cycloheptyl, octahydronaphthyl, tetrahydronaphthyl, dimethoxytetrahydronaphthyl, 2,3-dihydro-1H-indenyl and the like.

"Cycloalkylalkyl", alone or in combination, means an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, hydroxycyclopentylpropyl, tetrahydronaphthylpropyl, cyclohexylbutyl and the like. "cycloalkylcarbonyl" means an acyl radical of the formula cycloalkyl-C(O)— in which the term "cycloalkyl" has the significance give above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl and the like.

"Heteroatoms" means nitrogen, oxygen and sulfur heteroatoms.

"Heterocyclyl", alone or in combination, means a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 carbon atoms and more preferably 5–6 carbon atoms, and benzo fused ring systems. "Heterocyclyl" radicals may optionally be substituted on at least one, preferably 1–4, more preferably 1–3, even more preferably 1–2, carbon atoms by halogen, alkyl, alkoxy, hydroxy, oxo, thioxo, aryl, aralkyl, heteroaryl, hetoroaralkyl, amidino, N-alkylamidino, alkoxycarbonylamino, alkylsulfonylamino and the like, and/or on a secondary nitrogen atom by hydroxy, alkyl, aralkoxycarbonyl, alkanoyl, alkoxycarbonyl, heteroaralkyl, aryl or aralkyl radicals. More preferably, "heterocyclyl", alone or in combination, is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals. Examples of such heterocyclyl radicals include pyrrolidinyl, piperidinyl, piperazinyl, morpholinyl, thiamorpholinyl, 4-benzyl-piperazin-1-yl, pyrimidinyl, tetrahydrofuryl, pyrazolidonyl, pyrazolinyl, pyridazinonyl, pyrrolidonyl, tetrahydrothienyl and its sulfoxide and sulfone derivatives, 2,3-dihydroindolyl, tetrahydroquinolinyl, 1,2,3,4-tetrahydroisoquinolinyl, 1,2,3,4-tetrahydro-1-oxo-isoquinolinyl, 2,3-dihydrobenzofuryl, benzopyranyl, methylenedioxyphenyl, ethylenedioxyphenyl and the like.

"Heterocyclylalkyl", alone or in combination, means an alkyl radical as defined above in which at least one hydrogen atom, preferably 1–2, is replaced by a heterocyclyl radical as defined above, such as pyrrolidinylmethyl, tetrahydrothienylmethyl, piperidinylethyl and the like.

"Heteroaryl", alone or in combination, means a monocyclic or bicyclic, preferably monocyclic, aromatic heterocycle radical, having at least one, preferably 1 to 4, more preferably 1 to 3, even more preferably 1–2, nitrogen, oxygen or sulfur atom ring member and having preferably 5–6 ring members in each ring, which is optionally benzo fused or saturated carbocyclic fused, preferably 3–4 carbon atoms ($C_3$–$C_4$) and which is optionally substituted as defined above with respect to the definitions of aryl and heterocyclyl. More preferably, "heteroaryl", alone or in combination, is a radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused. Examples of such heteroaryl groups include imidazolyl, 1-benzyloxycarbonylimidazol-4-yl, pyrrolyl, pyrazolyl, pyridyl, 2-(1-piperidinyl)pyridyl, 2-(4-benzyl piperazin-1-yl)-1-pyridinyl, pyrazinyl, triazolyl, furyl, thienyl, oxazolyl, thiazolyl, indolyl, quinolinyl, 1-oxido-2-quinolinyl, isoquinolinyl, 5,6,7,8-tetrahydroquinolyl, 5,6,7,8-tetrahydroisoquinolinyl, quinoxalinyl, benzothiazolyl, β-carbolinyl, benzofuryl, benzimidazolyl, benzoxazolyl and the like.

"Heteroaralkyl", alone or in combination, means an alkyl radical as defined above in which at least one hydrogen atom, preferably 1–2, is replaced by a heteroaryl radical as defined above, such as 3-furylpropyl, 2-pyrrolyl propyl, chloroquinolinylmethyl, 2-thienylethyl, pyridylmethyl, 1-imidazolylethyl and the like.

"Halogen" and "halo", alone or in combination, means fluoro, chloro, bromo or iodo radicals.

"Haloalkyl", alone or in combination, means an alkyl radical as defined above in which at least one hydrogen atom, preferably 1–3, is replaced by a halogen radical, more preferably fluoro or chloro radicals. Examples of such haloalkyl radicals include 1,1,1-trifluoroethyl, chloromethyl, 1-bromoethyl, fluoromethyl, difluoromethyl, trifluoromethyl, bis(trifluoromethyl) methyl and the like.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis (dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

Procedures for preparing the compounds of this invention are set forth below. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Preparation of Compounds of Formula I

The compounds of the present invention represented by Formula I above can be prepared utilizing the following general procedures as schematically shown in Schemes I and II.

SCHEME I

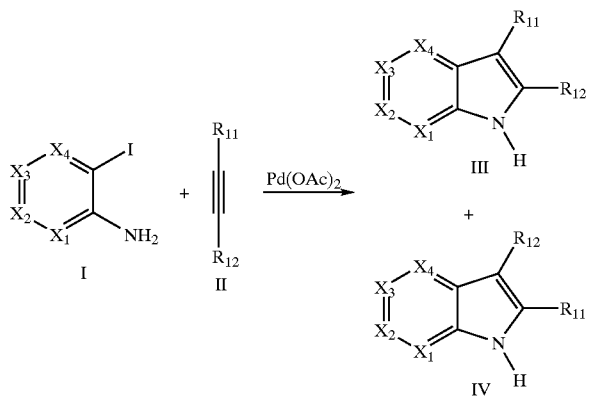

SCHEME II

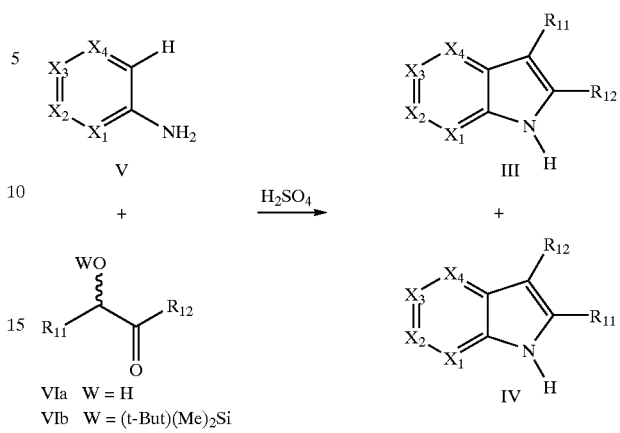

Several types of indole and azaindole synthesis can be used to prepare the compounds of this invention which are included by reference (for reviews of indole synthesis see G. Gribble Recent Developments in Indole Ring Synthesis-Methodology and Applications in Contemporary Organic Synthesis p-145–172; R. Sundberg and P. V. Nguyen Five Membered Ring Systems: Pyrroles and Benzo Derivatives, Chapter 5, Comprehensive Heterocyclic Chemistry) and the schemes shown below.

A general synthesis. of indoles and azaindoles useful for the preparation of the novel compounds of this invention is illustrated in Scheme I whereby an appropriately substituted acetylene (II) is coupled with an ortho iodoaniline (I) or a 1,2-iodoaminoheterocycle (for example, 2-amino-3-iodopyridine) using a palladium (0) mediated coupling under the conditions of Larock and coworkers (tetrabutylammonium chloride 1 eq., potassium acetate 5 eq., and triphenylphosphine (5 mol %), Tet. Lett. 1993, 2823–2826) to afford a mixture of regioisomeric indoles or azaindoles (III and IV) that can be separated by chromatography. Preferably, when utilizing the general synthesis of Scheme I in the preparation of the novel compounds of this invention, $R_1$, $R_2$, $R_3$ and $R_4$ will not contain halogen substituted aryl or heteroaryl and other radicals well known to those. skilled in the art which have the potential of interfering with, competing with or inhibiting the ring formation reaction.

A second general synthesis of indoles and azaindoles useful for the preparation of the novel compounds of this invention is illustrated in Scheme II whereby an appropriately substituted alpha-hydroxyketone (VI) or alpha-silyloxyketone (VIa) is coupled with an appropriately substituted aniline or amino substituted heterocycle (V) (for example, 2-aminopyridine, 3-aminopyridine, 4-aminopyridine, 3-amino-6-chloro pyridazine, 3-phenyl-6-aminopyridazine, 4-amino pyridazine, 3-methoxy-4-amino-6-chloropyridazine, 4-amino-2,6-dichloropyridine, 4-amino-2-chloropyridine, 4-amino-5-cyano-2-methoxypyridine, 4-amino-2-methyl pyridine, 4-amino-5-cyano-2-methoxypyridine, 2-amino-4-methylpyridine, 2-amino-4,6-dimethylpyridine, 2-amino-5-bromopyridine, 6-aminonicotinamide, 3-amino-2-chloro pyridine, 5-amino-2-chloropyridine, 5-amino-2-methoxy pyridine, 3-amino-2,6-dimethoxypyridine, 2,6-diamino pyridine, 2-aminopyrazine and 2,4-diamino pyrimidine, which are commercially available) under acid catalysis (in concentrated sulfuric acid at 190° C. see: Herbert et al J. Chem.

Soc. C 1969, p. 1505 or preferably under catalysis by p-toluenesulfonic acid in xylene with heat, see J. Szmuskovicz U.S. Pat. No. 3,565,912) to afford the regioisomeric indoles (III and IV) that can be separated by chromatography. Preferably, when utilizing the general synthesis of Scheme II in the preparation of the novel compounds of this invention, $R_1$, $R_2$, $R_3$ and $R_4$ will not contain an amino substituted aryl or heteroaryl and other radicals well known to those skilled in the art which have the potential of interfering with, competing with or inhibiting the ring formation reaction. The yields for the general reaction of Scheme II are more favorable when the substituted aniline or amino substituted heterocycle (V) is electron rich. Preferably, when $R_1$, $R_2$, $R_3$ or $R_4$ represent an electron withdrawing group directly attached to the aromatic ring, the electron withdrawing substituent should be introduced after the ring formation of Scheme II.

In a third general synthesis of indoles and azaindoles useful for the preparation of the novel compounds of this invention is illustrated in Scheme III whereby the appropriate grignard reagent is added to the cyano functional group of a 2-amino-1-cyanoaryl or heteroaryl (for example, 3-amino-4-cyanopyridine, 2-amino-5-nitrobenzonitrile, 2-amino-6-fluorobenzonitrile SCHEME IIa

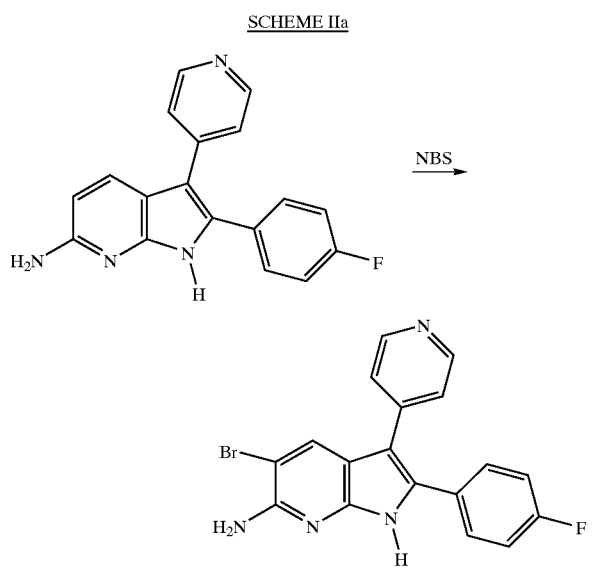

SCHEME IIb

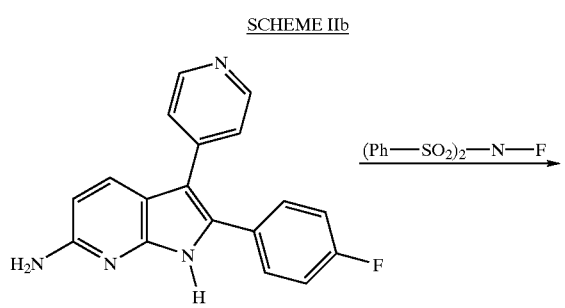

-continued

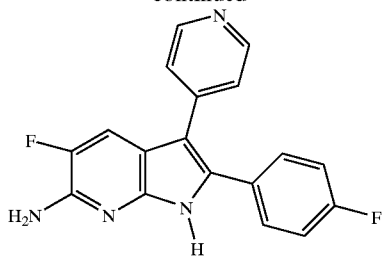

SCHEME III

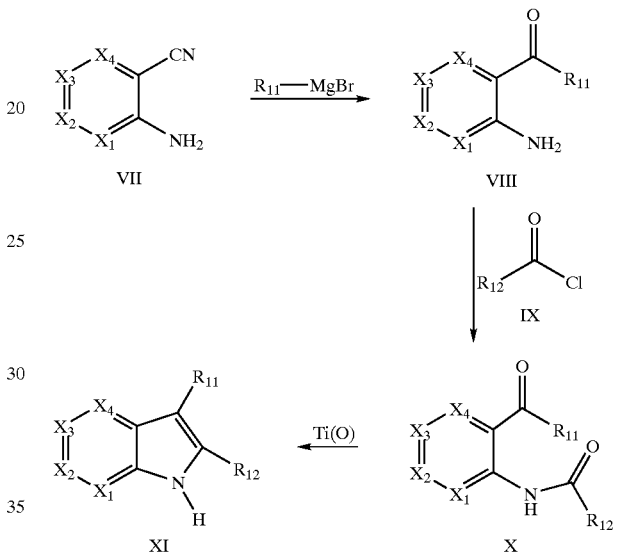

and 2-amino-5-chlorobenzonitrile, which are commercially available) system (VII) to afford the corresponding imine which upon hydrolysis affords the ketone (VIII). Alternatively, an ortho nitrobenzonitrile (for example, 2-methyl-6-nitrobenzonitrile, 5-chloro-2-nitrobenzonitrile, 4-cyano-3-nitrobenzotriflouride, 4,5-dimethoxy-2-nitrobenzonitrile, 4-chloro-2-nitrobenzonitrile, 6-nitro-o-anisonitrile and 6-bromo-2-cyano-4-nitroaniline, which are commercially available) can be converted into a 2-aminobenzonitrile as described by Jacini et al (Gazz. Chim. Ital. 1947, vol 77, 308). Acylation of the amino aryl or aminoheterocycle with the appropriate acid chloride (IX) (for example, benzoyl chloride, 3,5-bis(trifluoromethyl)benzoyl chloride, 2-bromobenzoyl chloride, 2-fluorobenzoyl chloride, pentafluorobenzoyl chloride 2,4-difluorobenzoyl chloride, 2,6-difluorobenzoyl chloride, 2,6-dichlorobenzoyl chloride, o-toluoyl chloride, m-anisoyl chloride, 3,4,5-trimethoxybenzoyl chloride, 4-biphenylcarbonyl chloride, 4-tert-butylbenzoyl chloride, 4-n-butylbenzoyl chloride, 4-cyanobenzoyl chloride, 2-naphthoyl chloride, 2,5-difluorobenzoyl chloride, 5-(dimethylsulfamoyl)-2-methoxybenzoyl chloride, 2,3-dichlorobenzoyl chloride, 1-naphthoyl chloride, 2-ethoxy-1-naphthoyl chloride and 2-naphthoyl chloride, which are commercially available) as shown in Scheme III affords the fused bicycle (III) after treatment with titanium (0) as described in the literature (Furstner et al Tet. Lett. 1991, 6695–6696). Such substituted benzoyl chlorides can be prepared from the corresponding commercially available benzoic acids by treatment with oxalyl chloride or thionyl chloride (Tet. Lett. 1993, 3543–3546; and Julia et al J. Chem. Soc. Perkin Trans. I 1991, Vol 5, 1101–1105, respectively).

SCHEME IV

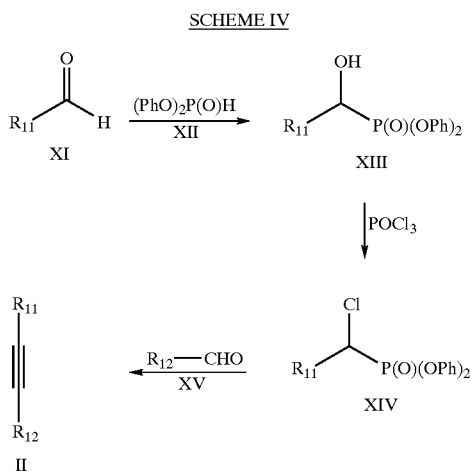

A general preparation of acetylenes for use in coupling in Scheme I is illustrated in Scheme IV. The appropriate aryl or heteroaryl aldehyde (XI) is reacted with diphenyl phosphite (XII) to afford the carbinol derivative (XIII) which is subsequently converted to the chloro derivative (XIV) by treatment with phosphorous oxychloride. Treatment of the chloromethanephosphonate with two equivalents of potassium t-butoxide followed by addition of the appropriate aldehyde (XV) affords the desired acetylene derivative (II) for use in Scheme I.

For purposes of illustration, examples of commercially available aryl aldehydes (XI) include 3-phenoxybenzaldehyde, 6-bromoveratraldehyde, 2-bromo benzaldehyde, 2-fluorobenzaldehyde, 4-fluoro benzaldehyde, 2-chlorobenzaldehyde, 2,4-dichloro benzaldehyde, 2-chloro-6-fluorobenzaldehyde, o-anisaldehyde, 2,3-dimethoxybenzaldehyde, 3-cyano benzaldehyde, 3-fluoro-p-anisaldehyde, 3-(3,4-dichlorophenoxy)benzaldehyde, 3-(3-(trifluoromethyl) phenoxy)benzaldehyde, 3-(4-methoxyphenoxy) benzaldehyde, 3-methyl-p-anisaldehyde, 4,4'-ethylbiphenyl-4-carboxaldehyde, 2-chloro-4-dimethylaminobenzaldehyde, 2,4,5-triethoxybenzaldehyde, 1-naphthaldehyde, 2-methoxy-1-naphthaldehyde, 4-methoxy-1 naphthaldehyde, 4-dimethylamino-1-naphthaldehyde, 4-methyl-1-naphthaldehyde, 2-benzyloxy-1-naphthaldehyde, 2-(2,4-dichlorobenzyloxy)-1-naphthaldehyde, 2-naphthaldehyde, 1-bromo-2-naphthaldehyde, 6-methoxy-2-naphthaldehyde and 7-methyl-2-naphthaldehyde.

For purposes of illustration, examples of commercially available heteroaryl aldehydes (XI) include 2,6-diphenyl-4-pyridinecarboxaldehyde, quinoline-3-carboxaldehyde, 2-chloro-3-quinolinecarboxaldehyde, 2-chloro-6-methoxy-3-quinolinecarboxaldehyde, 2-imidazolecarboxaldehyde, N-1-benzyl-2-imidazole carboxaldehyde, 2-methyl-3-imidazolecarboxaldehyde, 3-imidazolecarboxaldehyde, 2-ethyl-4-methyl-3-imidazolecarboxaldehyde, 4-methyl-5-imidazole carboxaldehyde and 2-phenyl-4-imidazolecarboxaldehyde.

Further, commercially available heteroaryl carboxylic acids or derivatives thereof can be converted to heteroaryl aldehydes by standard synthetic transformations well known to those skilled in the art. For example, heteroarylester can be reduced to the aldehyde by treatment with diisobutylaluminum hydride. For purposes of illustration, commercially available heteroaryl-carboxylic acids or derivatives thereof that can be converted into heteroaryl aldehydes (XI) include methyl 2-chloro-6-methyl-4-pyrimidinecarboxylate; 4-carboxypyrimidine; methyl 2,6-dimethylamino-4-pyrimidine carboxylate; and methyl 4,6-diphenyl-2-pyrimidine carboxylate. Alternatively, heteroaryl-halides can be converted into heteroaryl aldehydes (XI) by lithium-halogen exchange and quenching of the anion with dimethylformamide. For purposes of illustration, commercially available heteroarylhalides that can be converted into heteroaryl aldehydes (XI) include 6-chloro-2,4-dimethoxypyrimidine; 4-chloro-2-methylthio pyrimidine; 2-amino-4-chloro-6-methylpyrimidine; 4-chloro-2-phenylquinazoline; 4-chloro-2-methylquinoline; 4-chloro-2-methylquinoline; 4-chloro-7-(trifluoromethyl) quinoline; 4-chloro-6-methoxyquinoline; 4-chloro-2-picoline; 2,5-dimethyl-4-bromopyridine; 2-ethoxy-4-bromopyridine; 3-amino-4-chloroquinoline; and 3-amino-4-chloropyridine (note: the amino group of the substituted heteroaryl halide derivatives would first be suitably protected).

The alphahydroxyketone (VIa) or alphasilyloxyketone (VIb) of Scheme II can be prepared, for example when $R_{11}$ is 4-pyridyl or 4-quinolinyl, by generating the anion of the protected silyl ether (XVI) and reacting it with the N-methyl-N-methoxyamide (XVII) as shown in Scheme Va (Gallagher et al Biorg. Med. Chem. Lett. 1995, 1171–1176). The N-methyl-N-methoxyamide (XVII) can be obtained through reaction of $R_{12}$—C(O)Cl (for example, 3,5-bis (trifluoromethyl)benzoyl chloride; 2-bromobenzoyl chloride; 2-fluorobenzoyl chloride; pentafluorobenzoyl chloride; 2,4-difluorobenzoyl chloride; 2,6-difluoro benzoyl chloride; 2,6-dichlorobenzoyl chloride; o-toluoyl chloride; m-anisoyl chloride; 3,4,5-trimethoxy benzoyl chloride; 4-biphenylcarbonyl chloride; 4-tert-butyl benzoyl chloride; 4-n-butylbenzoyl chloride; 4-cyano benzoyl chloride; 2-naphthoyl chloride; 2,5-difluoro benzoyl chloride; 5-(dimethylsulfamoyl)-2-methoxybenzoyl chloride; 2,3-dichlorobenzoyl chloride; 1-naphthoyl chloride; 2-ethoxy-1-naphthoyl chloride; and 2-naphthoyl chloride, which are commercially available) with N,O-dimethylhydroxylamine in the presence of triethylamine. Such acid chlorides can be prepared from the corresponding $R_{12}$—C(O)OH by treatment with oxalyl chloride or thionyl chloride (Tet. Lett. 1993, 3543–3546 and Julia et al J. Chem. Soc. Perkin Trans. I 1991, Vol 5, 1101–1105, respectively).

SCHEME Va

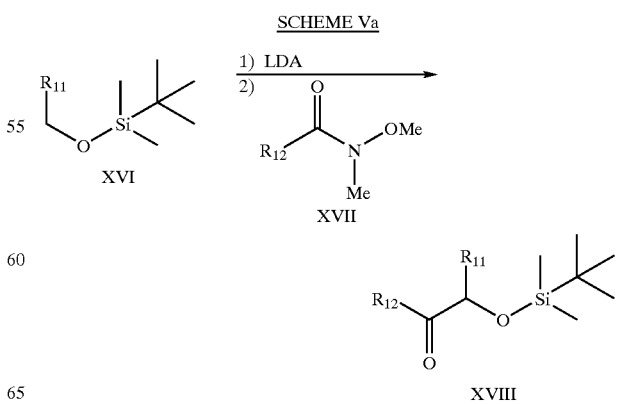

SCHEME Vb

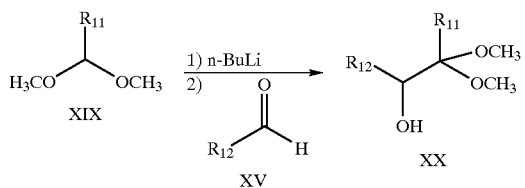

Alternatively, the dimethylketal XX, prepared according to Scheme Vb, can be used in the process of Scheme II in place of the alphahydroxyketone (VIa) and alphasilyloxyketone (VIb). The dimethylketal XX can be prepared by reacting the anion of the dimethoxyacetal XIX with the aldehyde XV. The dimethoxyacetal XIX can be readily prepared from the corresponding aldehyde XI (for example, 2,6-diphenyl-4-pyridinecarboxaldehyde; quinoline-3-carboxaldehyde; 2-chloro-3-quinoline carboxaldehyde; 2-chloro-6-methoxy-3-quinoline carboxaldehyde; 2-imidazolecarboxaldehyde; N-1-benzyl-2-imidazolecarboxaldehyde; 2-methyl-3-imidazole carboxaldehyde; 3-imidazolecarboxaldehyde; 2-ethyl-4-methyl-3-imidazolecarboxaldehyde; 4-methyl-5-imidazole carboxaldehyde; and 2-phenyl-4-imidazolecarboxaldehyde, which are commercially available) using methods well know to those skilled in the art.

Alternatively, indoles or azaindoles (III) can be prepared (Scheme VI) by reacting 2-substituted indoles or azaindoles (XIX) (for example, 2-(4-fluorophenyl) indole; 2-(2-naphthyl)indole; and 2-(4-chlorophenyl) indole, which are commercially available) with $R_{11}$—L, where L is a leaving group such as chloro, bromo, iodo, and the like radicals (for example, 4-chloropyridine, 4-chloroquinoline or 4-chloropyrimidine, which are commercially available). The 2-substituted indole or azaindole (XIX) can be treated with methyl magnesium bromide in ether followed by the addition of $R_{11}$—L and heated in a metal bomb at 160° C. for 20 hours to afford the indole or azaindole (III) (U.S. Pat. No. 3,551,567).

SCHEME VI

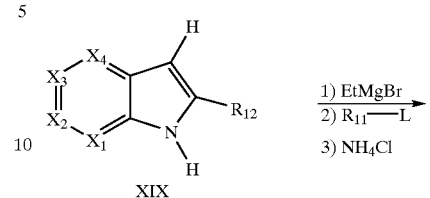

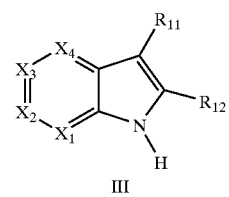

The following is included to further illustrate synthetic procedures useful in the preparation of the novel compounds of this invention. A specific example of a palladium mediated coupling as described in Scheme I is illustrated in Scheme VII wherein 1-(4-pyridyl)-2-(4-fluorophenyl) ethyne (1) and 2-iodoaniline (2) affords the regioisomeric 2,3-disubstituted indoles (3) and (4) as a 1:4 mixture, respectively. Compound (4) can be separated from compound (3) via flash chromatography.

SCHEME VII

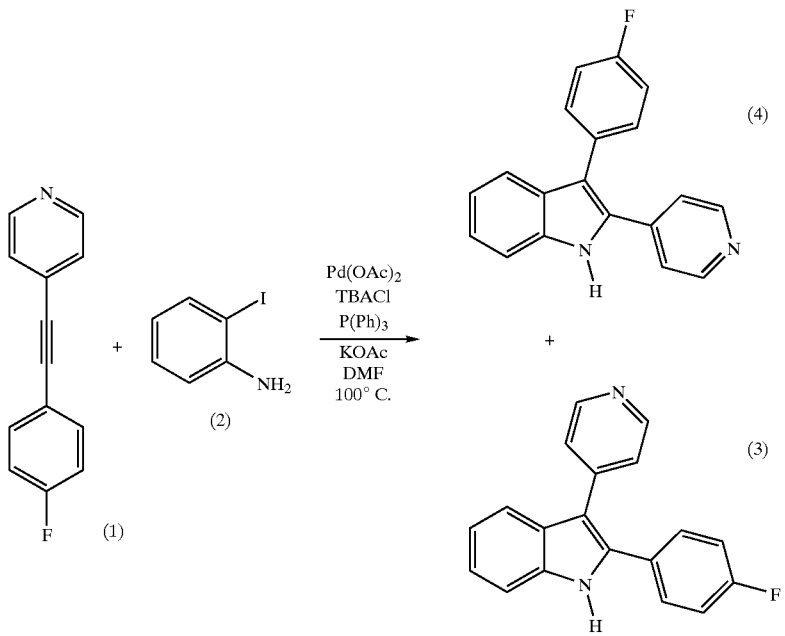

Alternatively, substituted acetylenes and iodoanilines can be coupled via a palladium mediated process as described in Scheme I. Substituted 2-iodoanilines can either be purchased or prepared by standard methods well known to those skilled in the art. For instance, monoiodination of a substituted aniline derivative would afford the 2-iodoaniline derivative using a variety of iodination reagents, such as N-iodo succinimide. Substituted acetylenes can be obtained as described in Scheme IV as illustrated in Scheme VIII for 1-(4-pyridyl)-2-(4-fluorophenyl)ethyne (1). The adduct (6) of diphenylphosphite and 4-pyridinecarboxaldehyde (5) is treated with phosphorous oxychloride to afford the chloro derivative (7). Condensation and elimination to the alkyne (1) is effected by treating the chloro derivative (7) and 4-fluorobenzaldehyde (8) with 2.1 equivalents of potassium t-butoxide.

SCHEME VIII

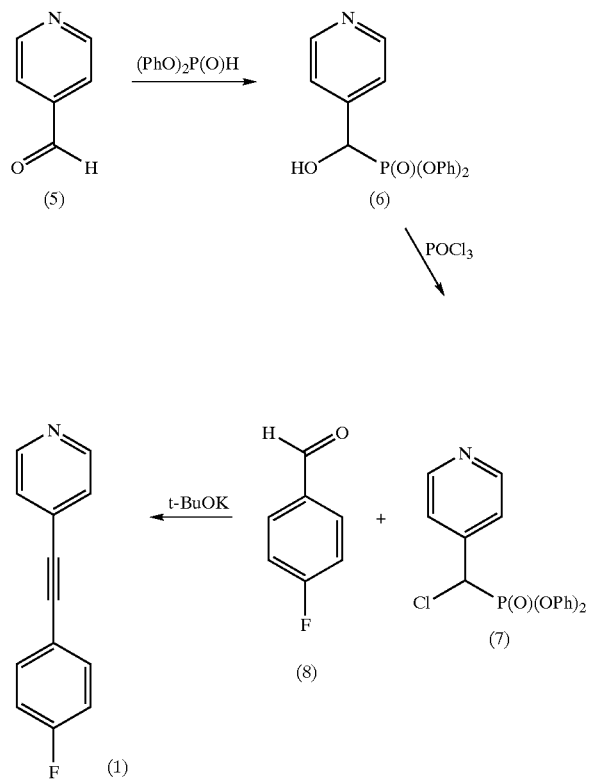

Scheme IX illustrates the preparation of substituted indoles according to the method of Scheme III, a titanium oxide mediated coupling. The grignard of 4-bromopyridine (10) is prepared by low temperature treatment (−78° C.) with n-butyl lithium followed by treatment with magnesium bromide etherate. A cooled solution of the grignard of (10) is added to anthranilonitrile (9) at low temperature (−50° C.) followed by warming to room temperature. The resultant imine (11) is hydrolyzed by treatment with sulfuric acid to the anilinoketone (12). Acylation of the anilinoketone (12) with 4-fluorobenzoyl chloride (13) affords the ketoamide (14). The regiospecific synthesis of indole (3) is completed by treatment of the ketoamide (14) with titanium oxide.

SCHEME IX

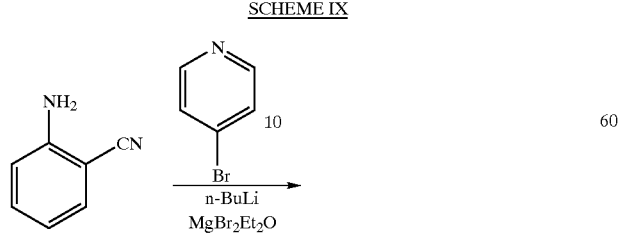

-continued

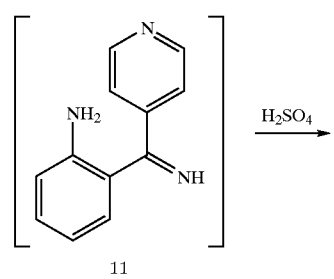

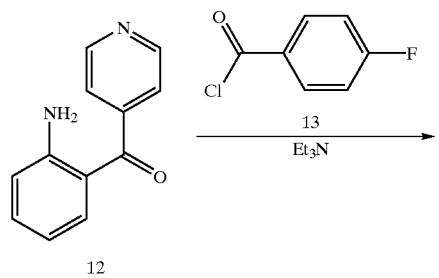

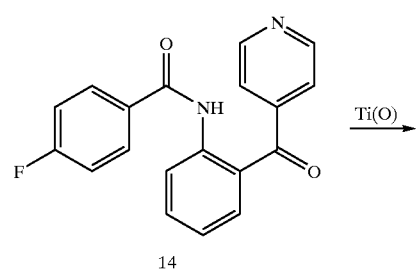

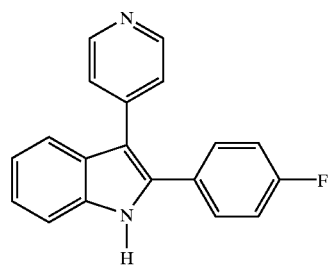

Scheme X illustrates the preparation of indoles and aza-indoles according to the method of Scheme II, acid mediated condensation of an aminoaryl or aminoheteroaryl and a substituted benzoin. Condensation of 2,6-diaminopyridine (15) with 1-(4-fluorophenyl)-2-t-butyldimethylsiloxy-2-(4-pyridyl)ethanone (16) is effected by treatment with an excess of p-toluenesulfonic acid in xylene at high temperatures to afford the azaindoles (17) and (18) which can be separated by flash chromatography.

Further fuctionalization of the 2,3-disubstituted indoles or azaindoles can be readily accomplished by reaction at an appropriately positioned group, such as an amino, carboxy, halo, substituted alkyl and the like group, on the 2,3-disubstituted indoles or azaindoles. Scheme XI illustrates functionalizing a 6-amino derivative (17) of a 2,3-disubstituted azaindole. Reaction of the 6-amino group of (17) with the mixed anhydride of N-4-t-butoxycarbonylaminobutyric acid (20) affords the N-4-t-butoxycarbonylaminobutanoyl compound (21), which can be readily converted into. the aminobutanoyl compound (22) by exposure to 90% trifluoroacetic acid and water for 1 hour. Similarly, the aminoalkylsulfonyl compound (26) can be prepared according to the method shown in Scheme XII.

-continued

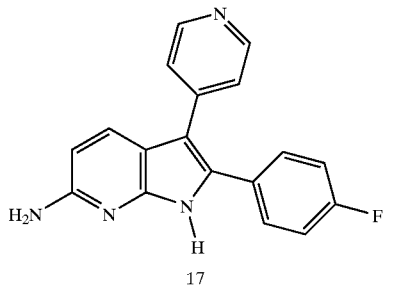

17

+

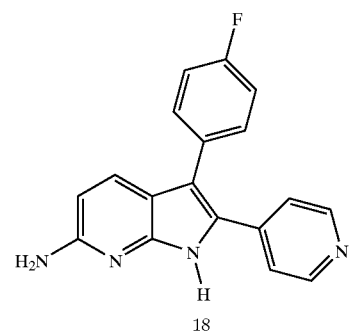

18

SCHEME X

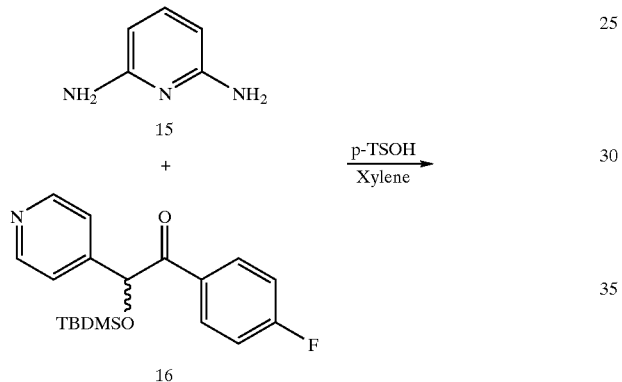

SCHEME XI

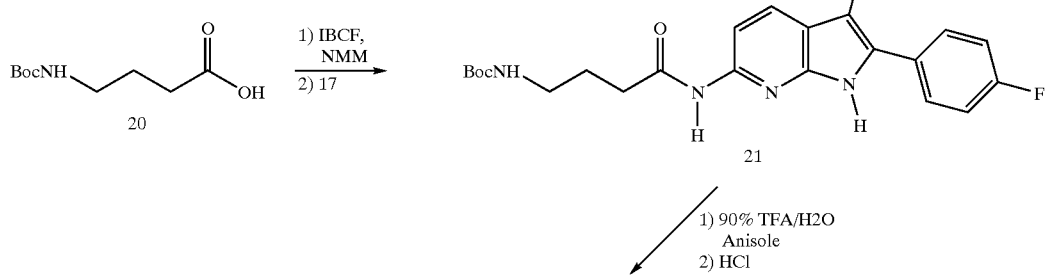

21

1) 90% TFA/H2O
   Anisole
2) HCl

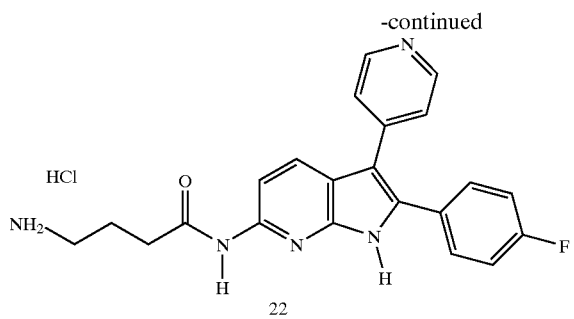

Further functionalization of 2,3-disubstituted indoles or azaindoles can be readily accomplished by site specific electrophilic substitution, and subsequent elaboration at the point of attachment of a newly introduced electrophile. For example, in Scheme XIII, N-bromosuccinimide (NBS) is reacted with compound (17) to introduce a bromo radical at the 5-position of (17) affording the bromo derivative (27). The bromo compound (27) can also be used to introduce other substituents at the 5-position using methods and reagents well known to those skilled in the art. Similarly, a fluoro radical can be introduced at the 5-position of (17) through the use of N-fluorobenzenesulfonimide to afford the fluoro derivative (28). Alternatively, a bromo compound like (27), or an appropriately 6-amino and indole NH protected derivative thereof, can be converted into the fluoro derivative by lithium halogen exchange followed by quenching of the lithio anion with N-fluorobenzene sulfonimide (Synlett. 187 (1991) and Tetrahedron Lett. 1631 (1992)). These reactions exemplify in a specific fashion the further substitution of an azaindole system after the indole has been formed by electrophilic substitution. In a more general sense, they demonstrate how other electrophilic agents (for example, iodine, Vilsmeier reagent, nitric acid and the like) can be used to substitute azaindoles and indoles in a specific fashion.

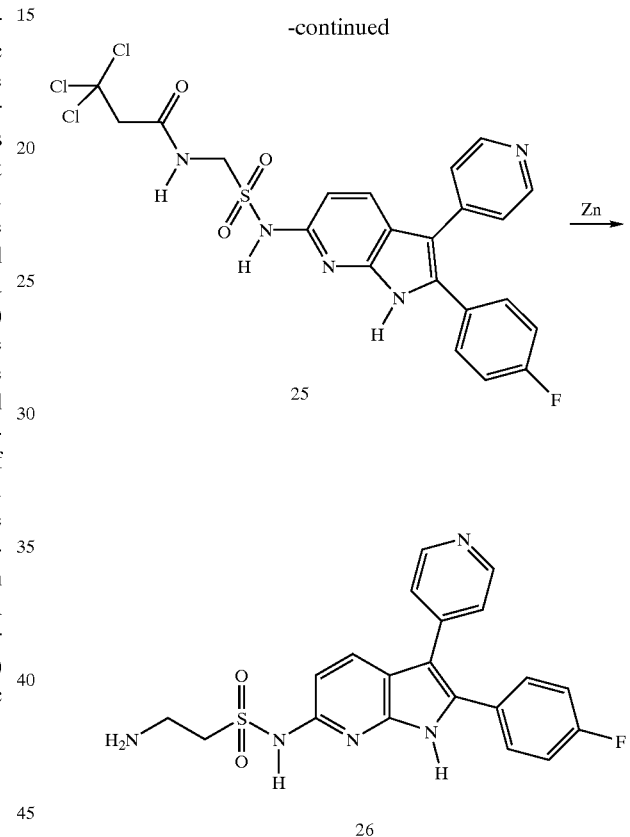

SCHEME XII

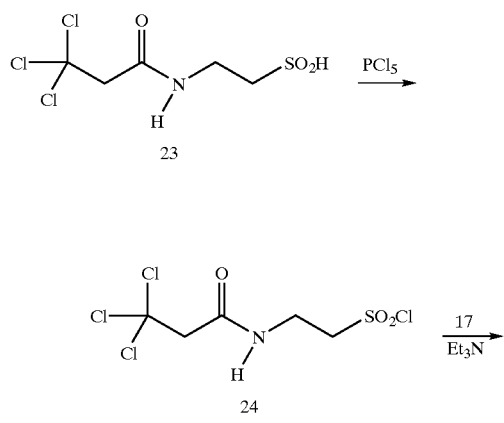

SCHEME XIII

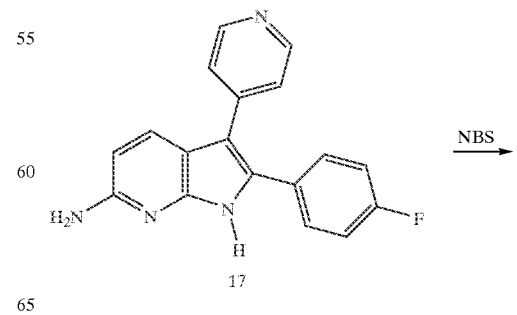

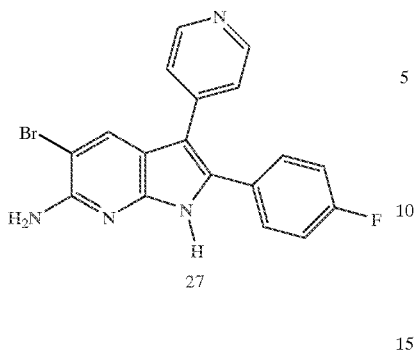
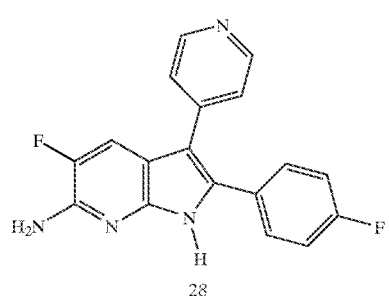
SCHEME XIV
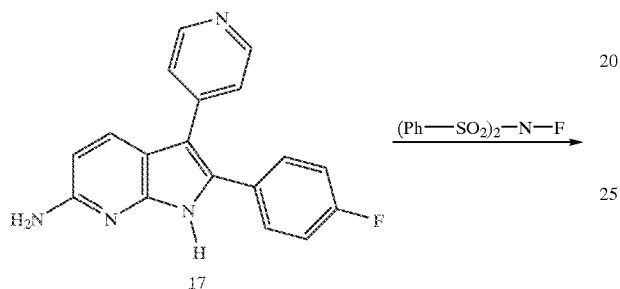
SCHEME XV
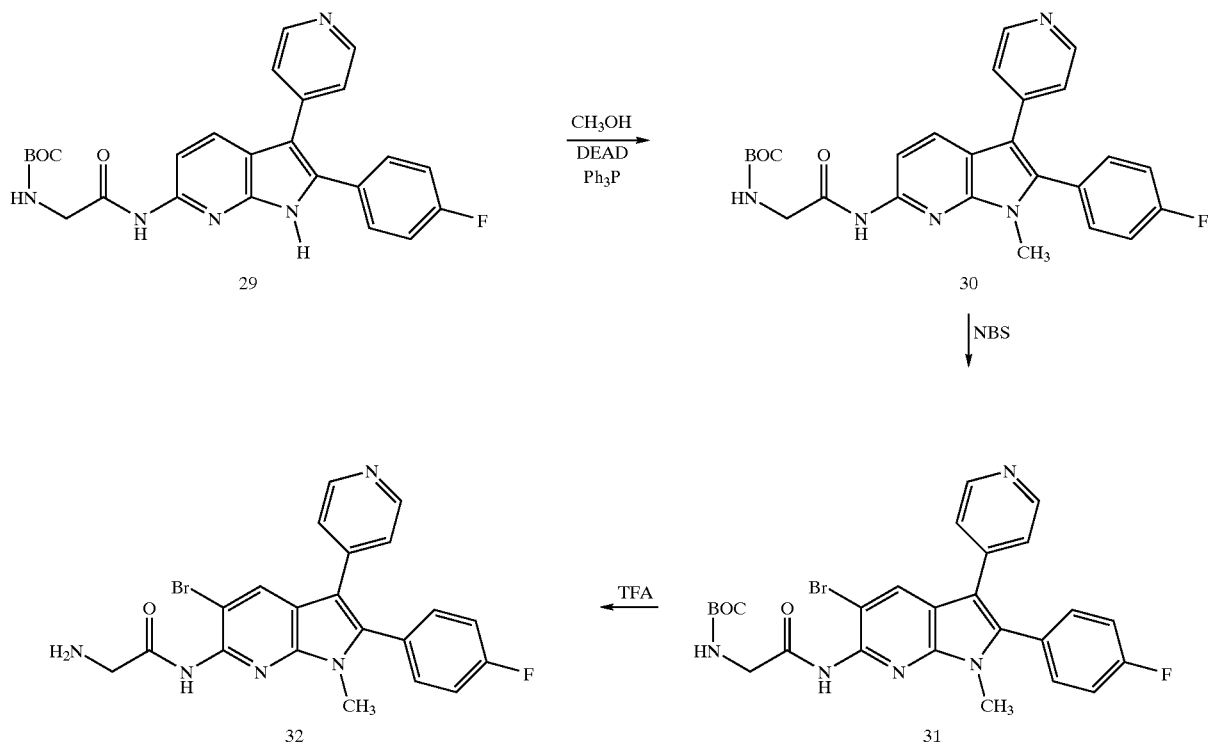
Further, functionalization of 2,3-disubstituted indoles or azaindoles can be readily accomplished at the indole nitrogen by utilizing the conditions of Mitsunobu wherein an appropriate alcohol is activated by treatment with triph enylphosphine and diethylazodicarboxylate (DEAD) and then reacted with the indole or azaindole compound. For example, in Scheme XV, the indole nitrogen of (29) is N-methylated under the Mitsunobu conditions and then reacted with NBS to afford the 5-bromo-N-1-methylderivative followed by deprotection affording (32).

SCHEME XVI

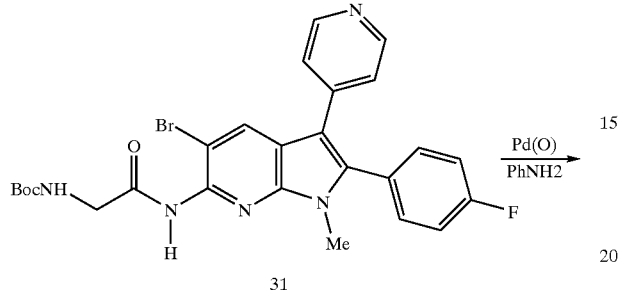

SCHEME XVIII

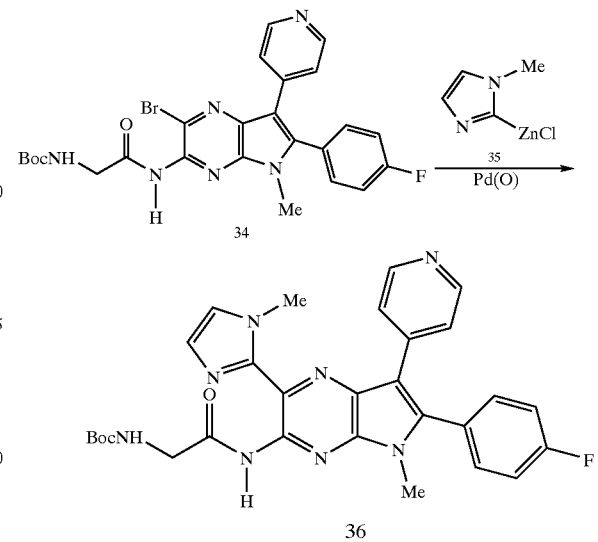

Further, functionalization of 2,3-disubstituted indoles or azaindoles can be readily accomplished by site specific electrophilic halogenation followed by palladium mediated coupling to introduce aryl substituent. Alternatively, an aryl halide can be converted into an aryl stannane by lithium halogen exchange followed by quenching with a trialkyl-stannyl chloride (for example, tributylstannyl chloride or trimethylstannyl chloride). The aryl stannane can then be reacted in the presence of palladium (O) in a coupling process. Those skilled in the art are well versed in the diverse conditions and methods available for palladium (O) assisted couplings (Palladium Reagents and Catalysts—Innovations in Organic Synthesis by Jiro Tsuji, Wiley (1995); and Palladium Reagents in Organic Syntheses by Heck, Academic Press (1985)).

SCHEME XVII

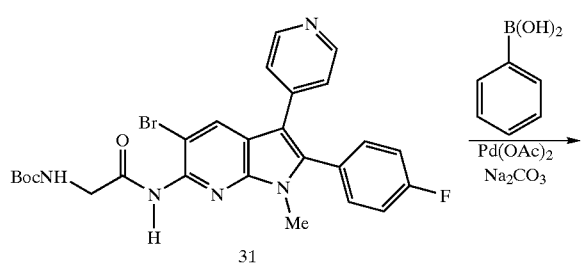

SCHEME XIX

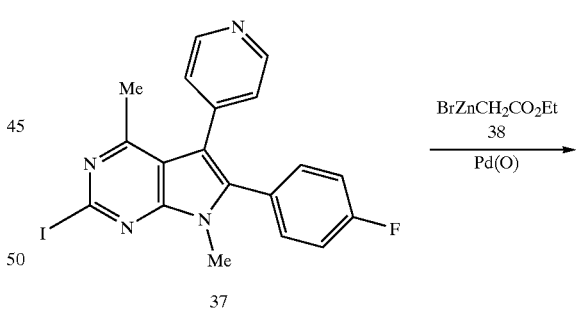

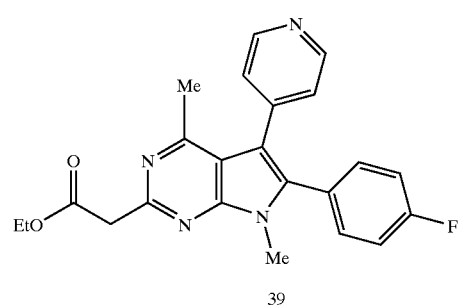

SCHEME XX

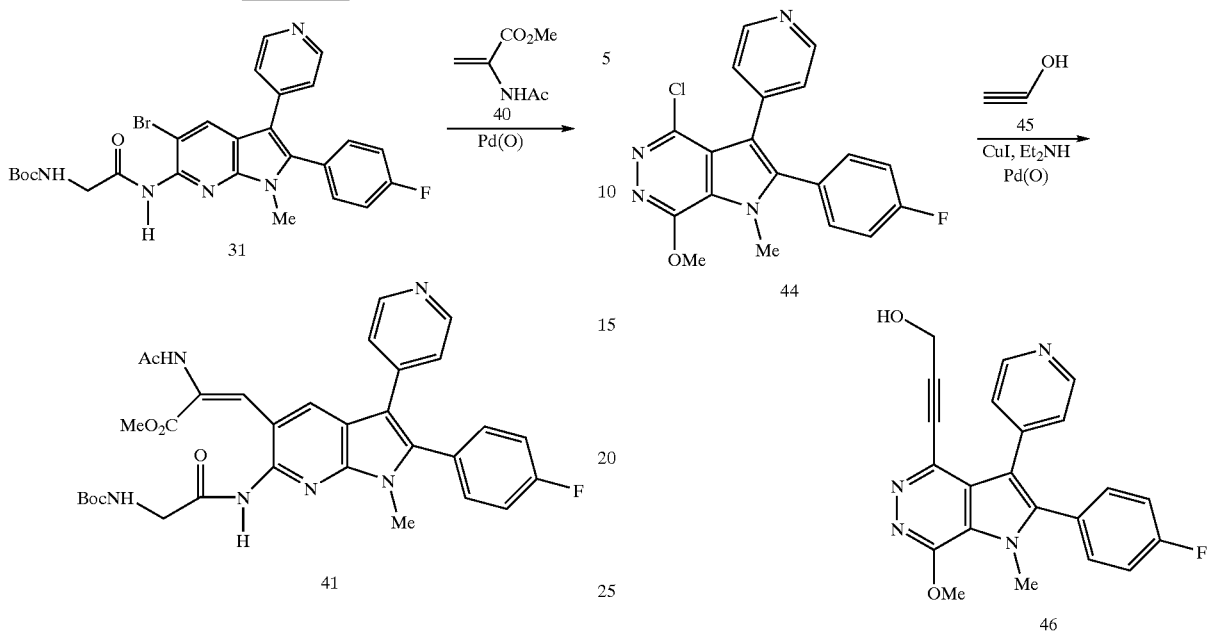

SCHEME XXI

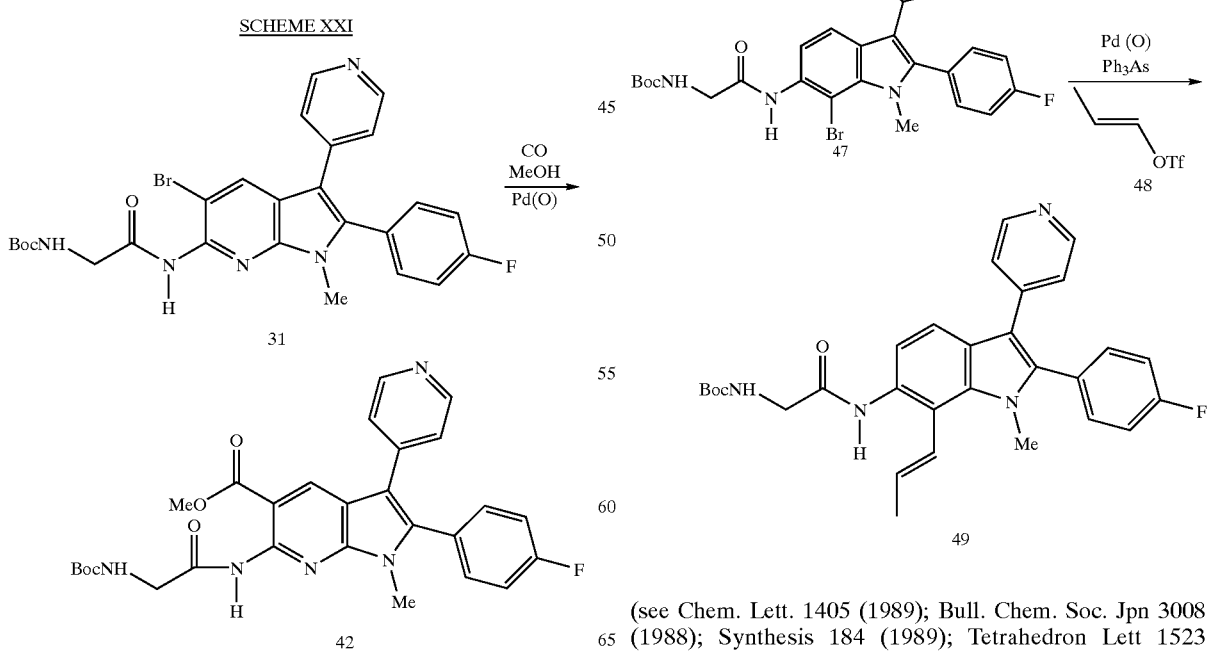

Schemes XVI–XXIII illustrate the use of palladium mediated couplings to prepare compounds of this invention. For example, bromo compound (31) can be coupled to aniline (other amines work as well, see Buchwald et al., J. Am. Chem. Soc. 7901 (1994); Buchwaid et al., Angew. Chem. Int. Ed. Engl. 1348 (1995); Hartwig et al., J. Am. Chem. Soc. 5969 (1994)) in a palladium (0) mediated coupling to afford compound (33) as illustrated in Scheme XVI. Alternatively, compound (31) can be coupled with an aryl boronic acid to afford a phenyl substituted derivative (43) as illustrated in Scheme XVII

SCHEME XXII

SCHEME XXIII (see Chem. Lett. 1405 (1989); Bull. Chem. Soc. Jpn 3008 (1988); Synthesis 184 (1989); Tetrahedron Lett 1523 (1990)). Bromo compound (34) can be coupled to a heterocycle like imidazole as exemplified in Scheme XVIII which has been demonstrated in the literature for similar systems ((35) plus 2-bromopyridine using tetrakistriphenylphosphine palladium (O), A. S. Bell et al., Tetrahedron Lett. 5013 (1988) and Synthesis 843 (1987)). Compound (37) (Scheme IXX) can be prepared from 4-amino-2-mercapto-6-methylpyrimidine by conversion to the corresponding 2-iodo derivative (iodine and hydrogen iodide in analogy to the conditions of bromine and HBr found in Zh. Org. Khim. (1991) 2235–2236) then converted into (37) in the manner illustrated in Scheme X. The Reformatsky reagent (38) can be coupled to the iodo derivative (37) using tetrakistriphenylphosphine

SCHEME XXIV

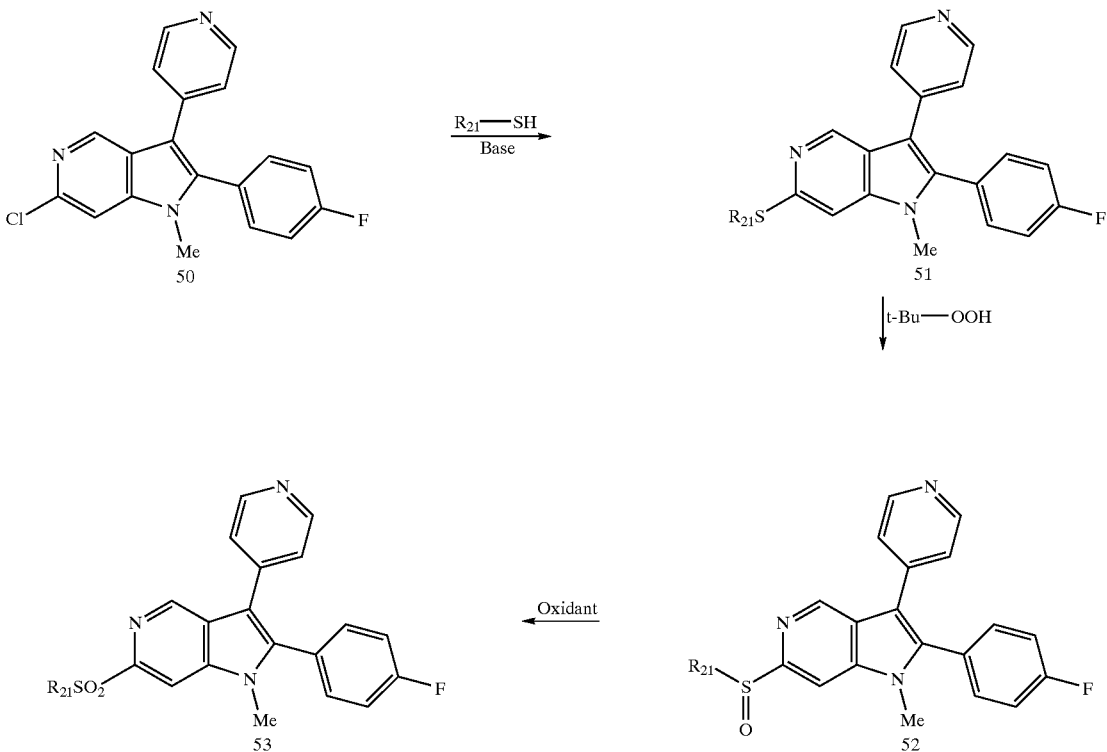

palladium (0) as in a similar manner to the previously described coupling with 4,6-dimethyl-2-iodopyrimidine (see: Yamanaka et al., Chem. Pharm. Bull. 4309 (1985)). An unnatural amino acid can be prepared directly from compound (41) of Scheme XX by reduction (for example, hydrogen gas in the presence of Rh(DIPAMP)). Compound (41) itself can be obtained through a palladium (O) mediated coupling of eneamide (40) directly with bromo derivative (41) utilizing the previously employed conditions for similar transformations (Pd2(dba)3, (o-tol)3P, Et3N, acetonitrile, see J Org. Chem. 2584 (1991); Synthesis 414 (1989); J. Org. Chem. 1289 (1991); Tetrahedron 7151 (1990)). The bromo derivative (31) can be converted to the carboxymethyl derivative (42) as illustrated in Scheme XXI utilizing the previously employed conditions for similar transformations (Pd2(dba)3, triphenylphosphine, methanol, carbon monoxide used with 2,6-dichloropyrazine, see Synthesis 923 (1990)). An acetylenic group can be directly coupled to the azaindole or indole as illustrated in Scheme XXII utilizing the previously employed conditions for similar transformations (tetrakistriphenylphosphine palladium (O), CuI, Et3N —see: Synthesis 728 (1984)). Compound (44) can be obtained utilizing commercially available 3-methoxy-4-amino-6-chloro-pyridazine in the manner of Scheme X. Vinyl functionalization of the appropriate 2,3-disubstituted indoles or azaindoles can be readily

SCHEME XXV

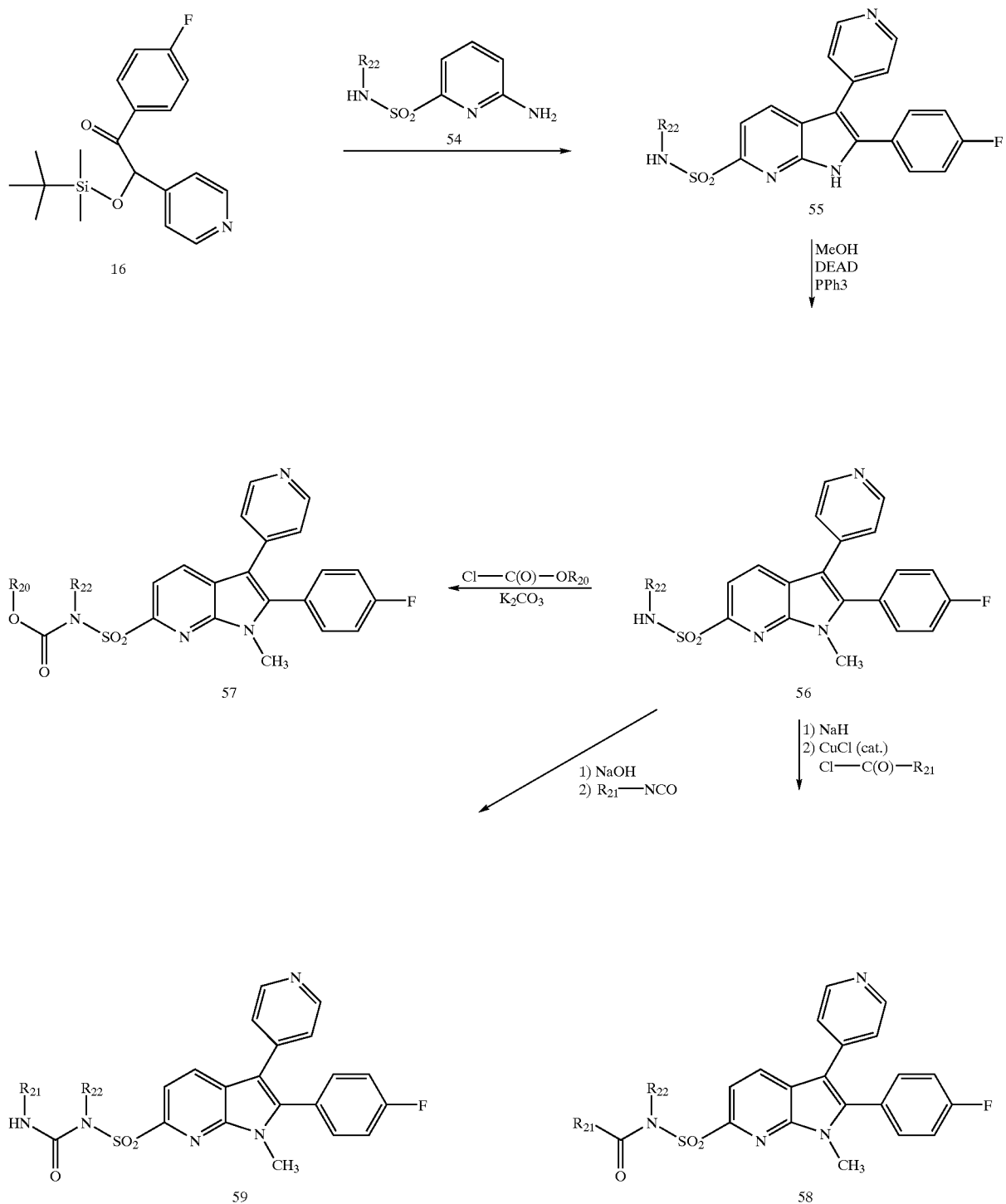

accomplished as illustrated in Scheme XXIII. Conversion of the bromo derivative (47) of Scheme XXIII to the tributyl stannyl derivative as described above can be followed by a palladium (0) mediated coupling to a vinyl triflate utilizing the previously employed conditions for similar transformations (Pd2(dba)3, Ph3As, NMP, see Tetrahedron Lett. 4243 (1991)). Compound (47) can be obtained from 3-amino-2-bromoaniline in a similar manner to Scheme X.

SCHEME XXVI

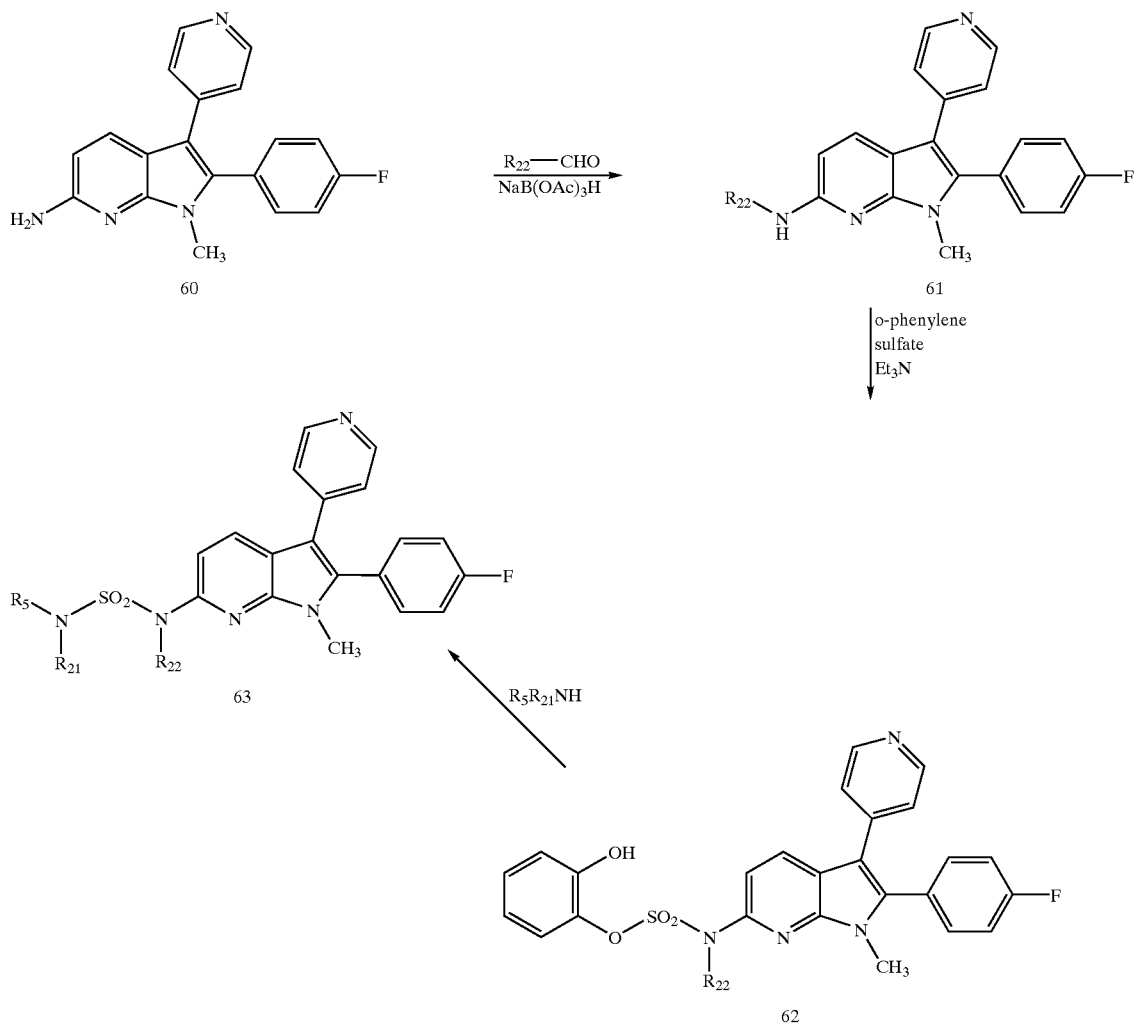

Further functionalization of the appropriate 2,3-disubstituted indoles or azaindoles can be readily accomplished by introduction of a sulfide group as illustrated in Scheme XXIV or alternatively the thiol can be introduced prior to indole formation. Examples of thiol introduction include alkyl thiol (Rumler et al., Pharmazie (1990) 657–659) and thiol itself (Pascual et al., Bull. Soc. Chim. Belg. 101:297–302 (1992)). For example, the chlorogroup of compound (50) can be displaced by a thiol reagent. The sulfide (51) can be oxidized to the sulfoxide (52) by treatment with t-butylhydroperoxide in the presence of the pyridine (Kagan et al., Tetrahedron asymmetry (1990) 597–610) or further oxidized to the sulfone (53) (Trost et al., Tetrahedron Lett (1981) 1287).

A sulfonamide radical can be introduced prior to the indole forming process (Schemes I or II) and then further fuctionalized as illustrated in Scheme XXV. Reaction of the sulfonamide (56) with excess chloroformates results in formation of compound (57) wherein $CR_3$=—$S(O)_2$—$NR_{22}$—$C(O)$—$OR20$ (J. Med. Chem. (1990) 2393–2407). Reaction of. the sulfonamide (56) with acid chlorides after deprotonation of the sulfonamide with sodium hydride results in formation of compound (58) wherein $CR_3$=—$S(O)_2$—$NR_{22}$—$C(O)$—$R_{21}$ (Curran, J. Org. Chem. (1990) 4584–4595). Reaction of the sulfonamide (56) with isocyanates results in the formation of compound (59) wherein $CR_3$=—$S(O)_2$—$NR_{22}$—$C(O)$—$NR_5R_{21}$ where $R_5$=hydrogen (Howbert et al., J. Med. Chem. (1990) 2393–2407).

Introduction of the substituent $CR_3$=—$NR_{22}$—$S(O)_2$—$NR_5R_{21}$ can be accomplished as illustrated in Scheme XXVI. First, the amino group of compound (60) can be alkylated in a reductive amination to afford compound (61). Then the alkylated amino substituent of compound (61) can be reacted with o-phenylene sulfate to afford (62) followed by further reaction with a second amine as illustrated in Scheme XXVI to afford compound (63) wherein $CR_3$=—$NR_{22}$—$S(O)_2$—$NR_5R_{21}$ (Lee et al., Bull. Korean Chem. Soc. (1992), 357).

Additional methods of indole and azaindole preparation are included by reference: G. Gribble Recent Developments in Indole Ring Synthesis-Methodology and Applications in Contemporary Organic Synthesis p-145–172; R. Sundberg and P. V. Nguyen Five Membered Ring Systems: Pyrroles and Benzo Derivatives, Chapter 5, Comprehensive Heterocyclic Chemistry. It will be understood that these novel compounds are not limited to the disclosed methods of making them.

Sulfonyl halides can be prepared by the reaction of a suitable alkyl, aryl, heteroaryl, heterocyclyl and the like Grignard or lithium reagents with sulfuryl chloride, or sulfur dioxide followed by oxidation with a halogen, preferably chlorine. Alkyl, aryl, heteroaryl, heterocyclyl and the like Grignard or lithium reagents can be prepared from their corresponding halide (such as chloro or bromo) compounds which are commercially available or readily prepared from commercially available starting materials using known methods in the art. Alternatively, mercaptans may be oxidized to sulfonyl chlorides using chlorine in the presence of water under carefully controlled conditions. Additionally, sulfonic acids may be converted into sulfonyl halides using reagents such as PCl, SOCl$_2$, ClC(O)C(O)Cl and the like, and also to anhydrides using suitable dehydrating reagents. The sulfonic acids are either commercially available or may be prepared using procedures well known in the art from commercially available starting materials. In place of the sulfonyl halides, sulfinyl halides or sulfenyl halides can be utilized to prepare compounds wherein the sulfonyl moiety is replaced by an sulfinyl or thio moiety, respectively. Arylsulfonic acids, benzo fused heterocyclyl sulfonic acids or heteroaryl sulfonic acids can be prepared by sulfonation of the aromatic ring by well known methods in the art, such as by reaction with sulfuric acid, SO$_3$, SO$_3$ complexes, such as DMF(SO$_3$), pyridine(SO$_3$), N,N-dimethylacetamide (SO$_3$), and the like. Preferably, such sulfonyl halides are prepared from such aromatic compounds by reaction with DMF(SO$_3$) and SOCl$_2$ or ClC(O)C(O)Cl. The reactions may be performed stepwise or in a single pot.

Alkyl sulfonic acids, aryl sulfonic acids, heterocyclyl sulfonic acids, heteroaryl sulfonic acids, alkylmercaptans, arylmercaptans, heterocyclylmercaptans, heteroarylmercaptans, alkylhalides, arylhalides, heterocyclylhalides, heteroarylhalides, and the like are commercially available or can be readily prepared from starting materials commercially available using standard methods well known in the art.

Thioether derivatives can be converted into the corresponding sulfone or sulfoxide by oxidizing the thioether derivative with a suitable oxidation agent in a suitable solvent. Suitable oxidation agents include, for example, hydrogen peroxide, sodium meta-perborate, oxone (potassium peroxy monosulfate), meta-chloroperoxybenzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Prodrugs of the compounds of this invention are also contemplated by this invention. A prodrug is an active or inactive compound that is modified chemically through in vivo physicological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples illustrate the preparation of compounds of the present invention and intermediates useful in preparing the compounds of the present invention.

EXAMPLE 1

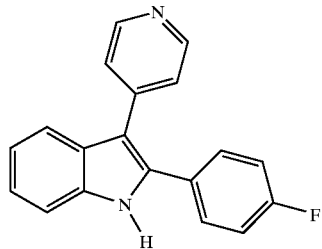

3

Section A
1-(4-Pyridyl)-2- (4-fluorophenyl)ethyne (1)

4-pyridinecarboxaldehyde (5) (25.0 g, 0.232 mol) was added dropwise over 1 h to a cooled solution (0° C.) of diphenylphosphite (54.0 g, 0.23 mol) and THF (100 mL). After complete addition, the reaction was allowed to warm to 23° C. After 16 h, the reaction was concentrated in vacuo and purified by direct application to flash chromatography (100% ethyl acetate) which afforded 4-pyridyl-hydroxymethyldiphenylphosphonate (6): Mass Spectrum (CI) 342 (MH+). 4-pyridyl-hydroxymethyldiphenylphosphonate (6) (15.3 g, 46 mmol), diethylaniline (4 mL), and phosphorous oxychloride (50 mL) were warmed to 90° C. for 16 h. The reaction was quenched by pouring the reaction mixture over ice (400 g). Potassium carbonate was added until a pH of 8 was obtained for the solution followed by extraction with methylene chloride (3×200 mL). After drying (MgSO4), the reaction was concentrated to afford crude 4-pyridyl-chloromethyldiphenylphosphonate (7) as a solid which was used in the next step without further purification: Mass Spectrum (CI) 360 (MH+). Potassium t-butoxide (3.30 g, 29.2 mmol) was added as a solid to 4-pyridyl-chloromethyldiphenylphosphonate (7) (5.00 g, 13.9 mmol), 4-fluorobenzaldehyde (8) (2.00 g, 15.3 mmol), and THF (70 mL) at 23° C. under argon. After 16 h, the reaction was quenched by adding to water (200 mL) over 3 min. After adjusting the pH of the solution to 7 with 1 N HCl, the mixture was extracted with ethyl acetate (3×350 mL), and dried (MgSO4). After concentration in vacuo, the residue was purified by flash chromatography (ethyl acetate:methylene chloride 1:1) to afford 1-(4-pyridyl)-2-(4-fluorophenyl)ethyne (1) as a solid: Mass Spectrum (CI) 198 (MH+).

3-(4-Pyridyl)-2-(4-fluorophenyl)indole (3)

2-Iodoaniline (2) (525 mg, 2.40 mmol) was added to palladium acetate (26.9 mg, 0.120 mmol), triphenyl phosphine (31.5 mg, 0 .120 mmol), potassium acetate (1.18 g, 12.0 mmol), tetrabutylammonium chloride (547 mg, 2.40 mmol), 1-(4-pyridyl)-2-(4-fluorophenyl)ethyne (1) (1.0 g, 4.8 mmol), and DMF (20 mL). The reaction was warmed to 100° C. for 17 h under argon. After cooling to 23° C., the reaction was poured into water (200 mL), extracted with ethyl acetate (3×100 mL), and dried (MgSO4). After concentration in vacuo, the residue was purified by flash chromatography on silica gel (methanol:ethyl acetate 1:19) to afford indoles (3) and (4) as a mixture of regioisomers (4:1): Mass Spectrum (CI) 289 (MH+).

Section B 4-(2-Aminobenzoyl)pyridine (12)

4-Bromopyridine (10) (49.38 g, 0.254 mol, free based from the hydrochloride by partitioning between ether and saturated bicarbonate) and diethyl ether (200 mL) was added over 1 h to a cooled solution (−78° C.) of n-butyl lithium (0.381 mol of a 2.5 M solution in hexane) under argon. After 30 min at (−78° C.), magnesium bromide diethyl etherate (98.37 g, 0.381 mol) was added via a dry powder addition funnel. After 1 h at −78° C., the reaction mixture was transferred to a jacketed addition funnel at −50° C., the solution was added to a cooled solution (−50° C.) of anthranilonitrile (15.0 g, 0.127 mol) and benzene (400 mL) over 10 minutes. The reaction was allowed to warm to 23° C. After 16 h, the reaction was poured into 18% sulfuric acid (100 mL), and was digested for 1 h. The resultant mixture was extracted with ethyl acetate ((400 mL), washed with water (3×400 mL), and dried (MgSO4). After concentration in vacuo, the residue was purified by flash chromatography in a step gradient fashion (one liter methylene chloride; one liter ethyl acetate:methylene chloride 1:9; one liter ethyl acetate:methylene chloride 2:8; one liter ethyl acetate:methylene chloride 3:7; one liter ethyl acetate:methylene chloride 4:6) which afforded 4-(2-aminobenzoyl)pyridine (12) as a solid : Mass Spectrum (CI) 199 (MH+).

Alternatively, to a solution of 1-iodo-2-nitrobenzene (3.76 g, 15.1 mmol) in dry THF (80 mL) at −78° C. was added n-butyl lithium (7.54 mL, 18.9 mmol) over 5 min. After 40 min at −78° C., ethyl isonicotinate was added in one portion in dry THF (70 mL). After 10 min, the reaction was allowed to warm to 0° C. for 10 min then quenched with 20 mL of glacial acetic acid: 30 mL of water. After adjusting the pH to 8 with saturated bicarbonate solution, the mixture was extracted with ethyl acetate (1×500 mL), washed with brine (2×500 mL), dried ($Na_2SO_4$). After concentration in vacuo, the reaction mixture was treated with 120 mL of 5 N NaOH: methanol: water (1:1:1). After removal of methanol in vacuo, the reaction mixture was extracted with ethyl acetate (1×500 mL), then dried ($Na_2SO_4$). After concentration in vacuo, the residue was purified by applying flash chromatography (step gradient methylene chloride 100% ; the 20% ethyl acetate: methylene chloride: then 40% ethyl acetate : methylene chloride) to afford 4-(2-nitobenzoyl)pyridine. 4-(2-Nitrobenzoyl) pyridine (100 mg, 0.44 mmol), stannous chloride dihydrate (297 mg, 1.32 mmol), and 1.1 mL of concentrated hydrochloric acid were warmed to 100° C. for 10 minutes. After cooling to 23° C., the reaction was poured into water (10 mL) and 5 N sodium hydroxide (14 mL) followed by extraction with ethyl acetate (2×50 mL). The ethyl acetate layer was washed with brine (1×20 mL), dried ($Na_2SO_4$), and conentarted in vacuo to afford 4-(2-aminobenzoyl)pyridine (12).

4-(2-(4-Fluoro-N-benzoylamino)benzoyl)pyridine (14)

4-Fluorobenzoyl chloride (78.0 mg, 0.55 mmol) was added to 4-(2-aminobenzoyl)pyridine (12) (100 mg, 0.50 mmol), triethylamine (0.35 mL, 2.52 mL), and chloroform (5.0 mL) at 23° C. under argon. After 24 h at 23° C., the reaction was poured into water (50 mL), extracted with ethyl acetate (3×50 mL), and dried (MgSO4). After concentration in vacuo, the residue was purified by flash chromatography (ethyl acetate: methylene chloride 1:1) to afford 4-(2-(4-fluoro-N-benzoylamino)benzoyl) pyridine (14): Mass Spectrum (CI) 321 (MH+).

3-(4-Pyridyl)-2-(4-fluorophenyl)indole (3)

Graphite (272 mg, 3.63 mmol) and potassium (100 mg, 0.33 mmol) were warmed to 150° C. under argon in a 250 mL round bottom flask with stirring for 25 min. THF (30 mL) was added via syringe to the hot bronze colored solid followed by a suspension of titanium (III) chloride (254 mg, 1.65 mmol) in THF (20 mL). The resultant black solution was allowed to reflux for 1 h. 4-(2-(4-fluoro-N-benzoylamino)benzoyl)pyridine (14) (100 mg, 0.33 mmol) and THF (20 mL) were then added to the hot (65° C.) reaction mixture over 5 min. After 1 h at 65° C., the reaction was cooled to 23° C. the filtered through a silica gel pad (20 g). After concentration in vacuo, the residue was purified by flash chromatography (ethyl acetate:methylene chloride 1:1) to afford 3-(4-pyridyl)-2-(4-fluorophenyl)indole (3): Mass spectrum (CI) 289 (MH+).

The following compounds were made using the above titanium (0) mediated ring closure with the appropriate acid chlorides to afford amide (X) which was closed to indole XI. It should be noted that in the case of 2-(3-bromothiophene) carbonyl chloride the amide X contains the bromo atom on the thiophene, but the ring closing (Ti) process removed the bromo from the thiophene resulting in the hydrido replacement.

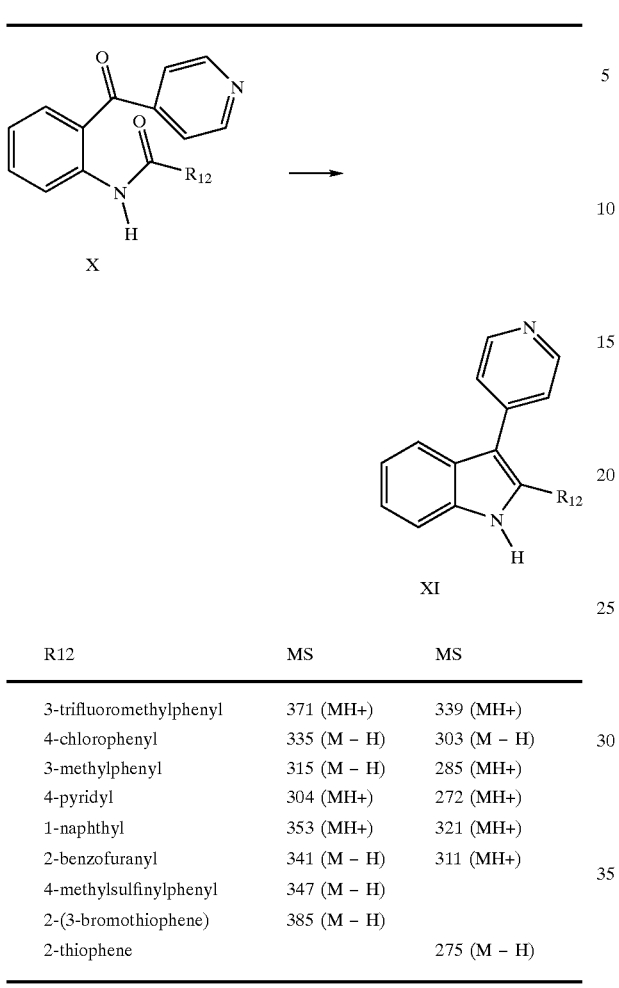

| R12 | MS | MS |
|---|---|---|
| 3-trifluoromethylphenyl | 371 (MH+) | 339 (MH+) |
| 4-chlorophenyl | 335 (M − H) | 303 (M − H) |
| 3-methylphenyl | 315 (M − H) | 285 (MH+) |
| 4-pyridyl | 304 (MH+) | 272 (MH+) |
| 1-naphthyl | 353 (MH+) | 321 (MH+) |
| 2-benzofuranyl | 341 (M − H) | 311 (MH+) |
| 4-methylsulfinylphenyl | 347 (M − H) | |
| 2-(3-bromothiophene) | 385 (M − H) | |
| 2-thiophene | | 275 (M − H) |

EXAMPLE 2

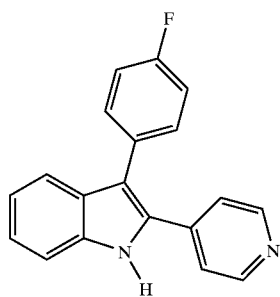

3-(4-Fluorophenyl)-2-(4-pyridyl)indole (4)

A portion of the 4:1 regioisomers from Section A of example 1, compounds (4):(3), was submitted to purification via flash chromatography (100% ethyl acetate) affording (4) in a pure state: Mass Spectrum (CI) 289 (MH+).

EXAMPLE 3

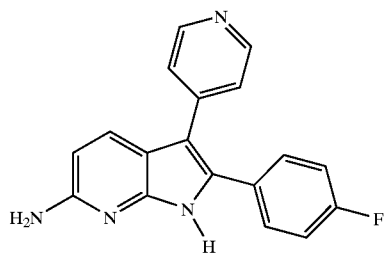

6-Amino-3-(4-pyridyl)-2-(4-fluorophenyl)-7-aza-indole (17)

1-(4-Fluorophenyl)-2-t-butyldimethylsiloxy-2-(4-pyridyl)ethanone (16) (3.45 g, 10.0 mmol), 2,6-diaminopyridine (1.09 g, 10.0 mmol), p-toluenesulfonic acid monohydrate (13.3 g, 70.0 mmol), and xylene (140 mL) were warmed to 60° C. under argon (note: all condensation reactions of this type were conducted behind an explosion shield). After 1 h at 60° C., the reaction was warmed to 135° C. for 3 h. After allowing the reaction to cool to 23° C., the top layer of xylene and p-toluenesulfonic acid was decanted from the bottom layer of gummy product residue. The lower product layer was partitioned between saturated bicarbonate (100 mL), and ethyl acetate (250 mL). The ethyl acetate layer was washed with brine (1×100 mL), and dried (Na2SO4). After concentration in vacuo, the residue was purified by applying flash chromatography (2 liters of ethyl acetate: hexane 7:3 followed by 100% ethyl acetate) to afford the cleanly separated regioisomer (17): Mass Spectrum (CI) 305 (MH+).

EXAMPLE 4

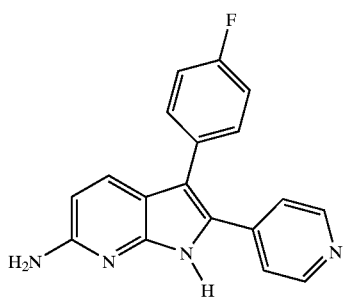

6-Amino-3-(4-fluorophenyl)-2-(4-pyridyl)-7-aza-indole (18)

A lower RF product from Example 3 was repurified by flash chromatography (100% ethyl acetate) to afford (18) as a solid: Mass Spectrum (CI) 305 (MH+).

EXAMPLE 5

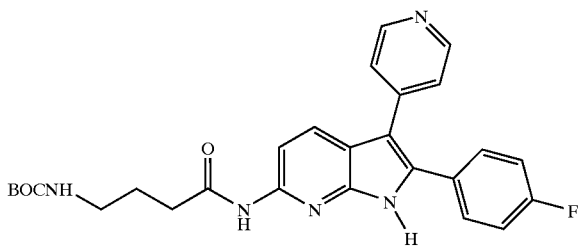

6-(4'-t-Butoxycarbonylamino-1'-oxo-butylamino)-3-(4-pyridyl)-2-(4-fluorophenyl)-7-aza-indole (20)

General Procedure for mixed anhydride coupling—Isobutyl chloroformate (32 ml, 0.24 mmol) was added dropwise to a −20–30° C. solution of 4-t-butoxycarbonyl aminobutyric acid (19) (50.1 mg, 0.247 mmol), 4-methylmorpholine (124 ml, 1.23 mmol), and THF (2 mL). After 20 min at −20–30° C., 6-Amino-3-(4-pyridyl)-2-(4-fluorophenyl)-7-aza-indole (17) (75 mg, 0.24 mmol) and THF (3 mL) was added in one portion. The reaction was allowed to warm to 23° C. After 16 h at 23° C., the reaction was poured into saturated bicarbonate (80 mL), extracted with ethyl acetate (2×100 mL), washed with brine (1×100 mL), and dried (Na2SO4). After concentration in vacuo, the residue was purified by application to two preparative chromatography plates (silica gel 2 mm thickness, 100% ethyl acetate) to afford 6-(4'-t-butoxycarbonylamino-1'-oxo-butylamino)-3-(4-pyridyl)-2-(4-fluorophenyl)-7-aza-indole (20) as a solid: Mass Spectrum (CI) 489 (MH+). Ethyl chloroformate can be used in place of isobutyl chloroformate in this process.

EXAMPLE 6

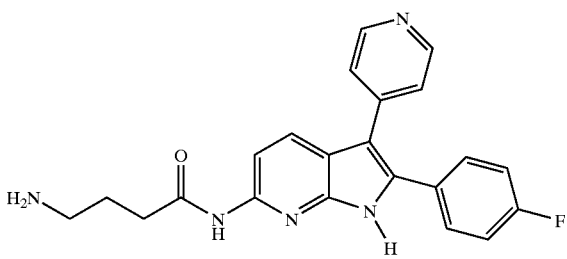

6-(4'-Amino-1'-oxo-butylamino)-3-(4-pyridyl)-2-(4-fluorophenyl)-7-aza-indole (21)

A solution of trifluoroacetic acid:water: anisole (900 ml:100 ml: 39 ml) was added to 6-(4'-t-butoxy carbonylamino-2'-oxo-amino)-3-(4-pyridyl)-2-(4-fluorophenyl)-7-aza-indole (20) (38 mg, 0.078 mmol) at 23° C. After 1 h at 23° C., the reaction was concentrated with a stream of nitrogen in a ventilated hood. The residue was triturated with 2 mL of ether, the resultant solid filtered and washed with ether (3×2 mL). The TFA salt of (21) was dissolved in 2 mL of water containing 3 equivalents of 1 N HCl and subsequently freeze-dried to afford the HCl salt of 6-(4'-amino-2'-oxo-amino)-3-(4-pyridyl)-2-(4-fluorophenyl)-7-aza-indole (21). The HCl salt was used in biological testing or alternatively the free base can be used in biological testing which was obtained by partioning the hydrochloride salt between ethyl acetate and saturated bicarbonate. The ethyl acetate layer was dried (Na2SO4), and concentrated in vacuo to afford 6-(4'-amino-1'-oxo-butylamino)-3-(4-pyridyl)-2-(4-fluorophenyl)-7-aza-indole (21) as a solid: Mass Spectrum (CI) 389 (MH+).

EXAMPLE 7

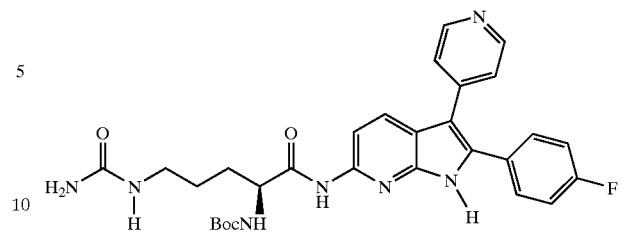

6-(5'-Ureido-1'-oxo-2'-t-butoxycarbonylaminopentylamino)-3-(4-pyridyl)-2-(4-fluorophenyl)-7-aza-indole (26)

Compound (26) was prepared in the manner of example 5 with the following substitution: N-a-t-Boc-citrulline was used in place of N-t-Boc-g-aminobutyric acid which afforded 6-(5'-ureido-1'-oxo-2'-t-butoxycarbonylaminopentylamino)-3-(4-pyridyl)-2-(4-fluorophenyl)-7-aza-indole (26) after preparative plate chromatography: Mass Spectrum (CI) 562 (MH+).

EXAMPLE 8

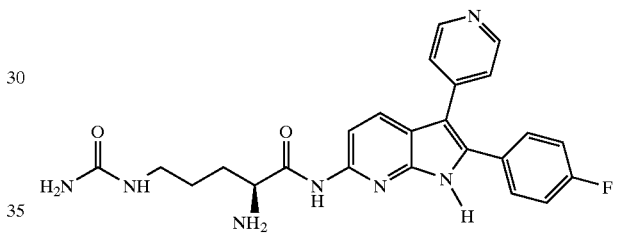

6-(5'-Ureido-1'-oxo-2'-aminopentylamino)-3-(4-pyridyl)-2-(4-fluorophenyl)-7-aza-indole (27)

Compound (27) was prepared from compound (26) in the manner of example 6 which afforded 6-(5'-ureido- 2'-oxo-3'-aminopentylamino)-3-(4-pyridyl)-2-(4-fluorophenyl)-7-aza-indole (27): Mass Spectrum (CI) 462 (MH+).

EXAMPLE 9

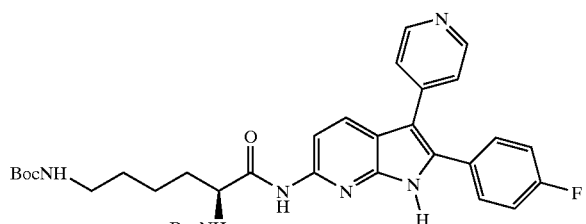

6-(6'-t-Butoxycarbonylamino-1'-oxo-2'-butoxycarbonylaminohexylamino)-3-(4-pyridyl)-2-(4-fluorophenyl)-7-aza-indole (28)

Compound (28) was prepared in the manner of example 5 with the following substitution: N-a-t-Boc-e-Boc-lysine was used in place of N-t-Boc-g-aminobutyric acid which afforded 6-(6'-t-Butoxycarbonylamino-1'-oxo-2'-t-butoxycarbonylaminopentylamino)-3-(4-pyridyl)-2-(4-fluoro-phenyl)-7-aza-indole (28) after preparative plate chromatography: Mass Spectrum (CI) 633 (MH+).

EXAMPLE 10

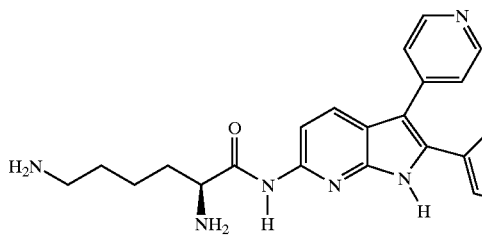

6-(6'-Amino-1'-oxo-2'-aminohexylamino)-3-(4-pyridyl)-2-(4-fluorophenyl)-7-aza-indole (29)

Compound (29) was prepared from compound (28) in the manner of example 6 which afforded 6-(6'-amino-1'-oxo-2'-aminohexylamino)-3-(4-pyridyl)-2-(4-fluorophenyl)-7-aza-indole (29): Mass Spectrum (CI) 433 (MH+).

EXAMPLE 11

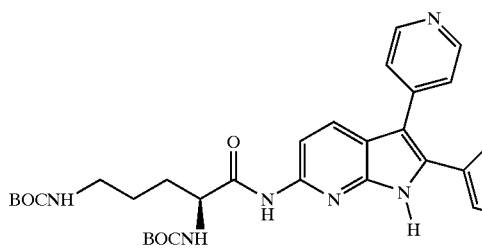

6-(5'-t-Butoxycarbonylamino-1'-oxo-2'-t-butoxycarbonylaminopentylamino)-3-(4-pyridyl)-2-(4-fluorophenyl)-7-aza-indole (30)

Compound (30) was prepared in the manner of example 5 with the following substitution: N-a-t-Boc-d-Boc-ornithine was used in place of N-t-Boc-g-aminobutyric acid which afforded 6-(5'-t-Butoxycarbonylamino-1'-oxo-2'-t-butoxycarbonylaminopentylamino)-3-(4-pyridyl)-2-(4-fluorophenyl)-7-aza-indole (30) after preparative plate chromatography: Mass Spectrum (CI) 619 (MH+).

EXAMPLE 12

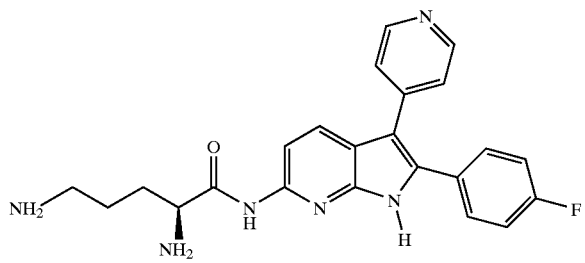

6-(5'-Amino-1'-oxo-2'-aminopentylamino)-3-(4-pyridyl)-2-(4-fluorophenyl)-7-aza-indole (31)

Compound (31) was prepared from compound (30) in the manner of example 6 which afforded 6-(5'-amino-1'-oxo-2'-aminopentylamino)-3-(4-pyridyl)-2-(4-fluorophenyl)-7-aza-indole (31): Mass Spectrum (CI) 419 (MH+).

EXAMPLE 13

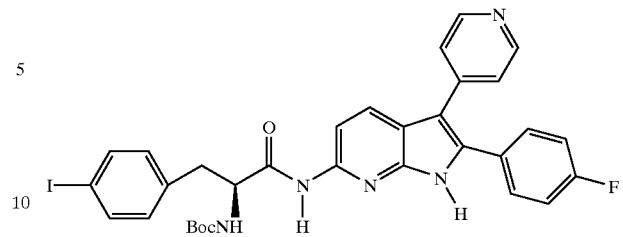

6-(3'-(4-Iodophenyl)-1'-oxo-2'-t-butoxycarbonylaminopropylamino)-3-(4-pyridyl)-2-(4-fluorophenyl)-7-aza-indole (32)

Compound (32) was prepared in the manner of example 5 with the following substitution: N-a-t-Boc-p-iodo-phenylalanine was used in place of N-t-Boc-g-aminobutyric acid which afforded 6-(3'-(4-iodophenyl)-1'-oxo-2'-t-butoxycarbonylaminopropylamino)-3-(4-pyridyl)-2-(4-fluorophenyl)-7-aza-indole (32) after preparative plate chromatography: Mass Spectrum (CI) 678 (MH+).

EXAMPLE 14

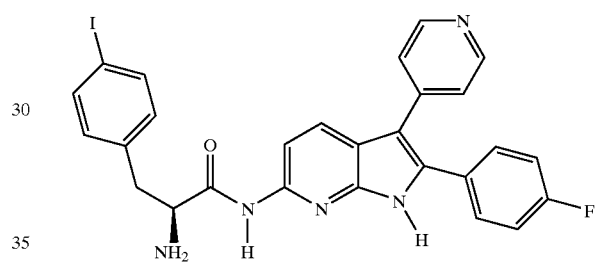

6-(3'-(4-Iodophenyl)-1'-oxo-2'-aminoDropylamino)-3-(4-pyridyl)-2-(4-flubrophenyl)-7-aza-indole (33)

Compound (33) was prepared from compound (32) in the manner of example 6 which afforded 6-(3'-(4-iodophenyl)-1'-oxo-2'-aminopropylamino)-3-(4-pyridyl)-2-(4-fluorophenyl)-7-aza-indole (33): Mass Spectrum (CI) 578 (MH+).

EXAMPLE 15

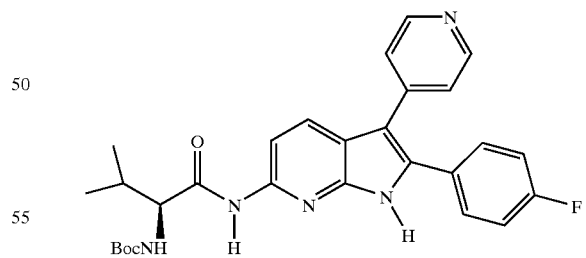

6-(3'-Methyl-1'-oxo-2'-t-butoxycarbonylaminobutylamino)-3-(4-pyridyl)-2-(4-fluorophenyl)-7-aza-indole (34)

Compound (34) was prepared in the manner of example 5 with the following substitution: N-a-t-Boc-valine was used in place of N-t-Boc-g-aminobutyric acid which afforded 6-(3'-Methyl-1'-oxo-2'-t-butoxycarbonylaminobutylamino)-3-(4-pyridyl)-2-(4-fluorophenyl)-7-aza-indole (34) after preparative plate chromatography: Mass Spectrum (CI) 504 (MH+).

EXAMPLE 16

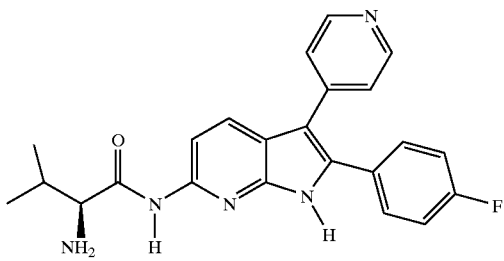

6-(3'-Methyl-1'-oxo-2'-aminobutylamino)-3-(4-pyridyl)-2-(4-fluorophenyl)-7-aza-indole (35)

Compound (35) was prepared from compound (34) in the manner of example 6 which afforded 6-(3'-Methyl-1'-oxo-2'-aminobutylamino)-3-(4-pyridyl)-2-(4-fluorophenyl)-7-aza-indole (35): Mass Spectrum (CI) 404 (MH+).

EXAMPLE 17

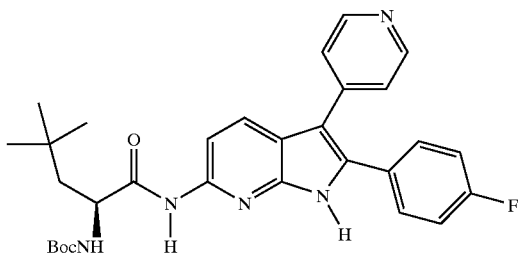

6-(4',4'-Dimethyl-1'-oxo-2'-t-butoxycarbonylaminopentylamino)-3-(4-pyridyl)-2-(4-fluorophenyl)-7-aza-indole (36)

Compound (36) was prepared in the manner of example 5 with the following substitution: N-a-t-Boc-b-t-butylalanine was used in place of N-t-Boc-g-aminobutyric acid which afforded 6-(4',4'-Dimethyl-1'-oxo-2'-t-butoxycarbonylaminopentylamino)-3-(4-pyridyl)-2-(4-fluorophenyl)-7-aza-indole (36) after preparative plate chromatography: Mass Spectrum (CI) 532 (MH+).

EXAMPLE 18

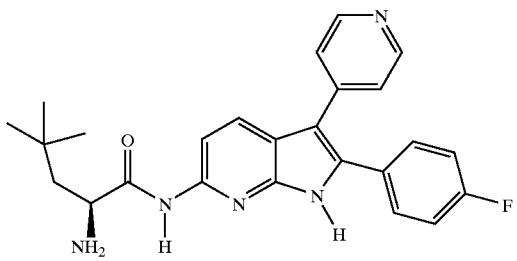

6-(4',4'-Dimethyl-1'-oxo-2'-aminopentylamino)-3-(4-pyridyl)-2-(4-fluorophenyl)-7-aza-indole (37)

Compound (37) was prepared from compound (36) in the manner of example 6 which afforded 6-(4',4'-Dimethyl-1'-oxo-2'-aminopentylamino)-3-(4-pyridyl)-2-(4-fluorophenyl)-7-aza-indole (37): Mass Spectrum (CI) 432 (MH+).

EXAMPLE 19

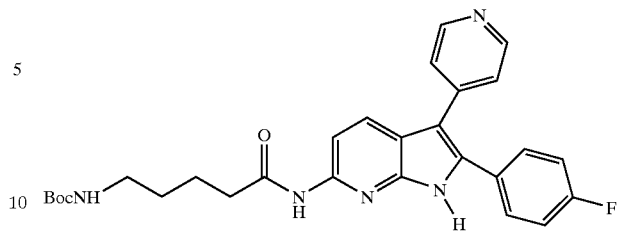

6-(5'-t-Butoxycarbonylamino-1'-oxo-pentylamino)-3-(4-pyridyl)-2-(4-fluorophenyl)-7-aza-indole (38)

Compound (38) was prepared in the manner of example 5 with the following substitution: N-t-Boc-5-aminovaleric acid was used in place of N-t-Boc-g-aminobutyric acid which afforded 6-(5'-t-butoxycarbonylamino-1'-oxo-pentylamino)-3-(4-pyridyl)-2-(4-fluoro-phenyl)-7-aza-indole (38) after preparative plate chromatography: Mass Spectrum (CI) 504 (MH+).

EXAMPLE 20

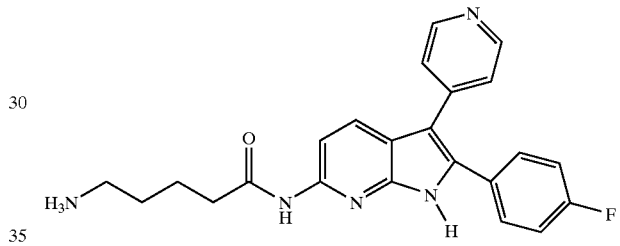

6-(5'-Amino-1'-oxo-pentylamino)-3-(4-pyridyl)-2-(4-fluorophenyl)-7-aza-indole (39)

Compound (39) was prepared from compound (38) in the manner of example 6 which afforded 6-(5'-amino-1'-oxo-pentylamino)-3-(4-pyridyl)-2-(4-fluorophenyl)-7-aza-indole (39): Mass Spectrum (CI) 404 (MH+).

EXAMPLE 21

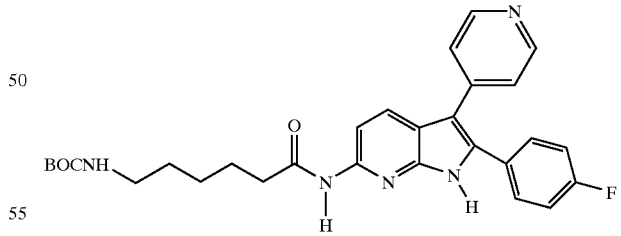

6-(6'-t-Butoxycarbonylamino-1'-oxo-hexylamino)-3-(4-pyridyl)-2-(4-fluorophenyl)-7-aza-indole (40)

Compound (40) was prepared in the manner of example 5 with the following substitution: N-t-Boc-6-aminocaproic acid was used in place of N-t-Boc-g-aminobutyric acid which afforded 6-(6'-t-butoxycarbonylamino-1'-oxo-hexylamino)-3-(4-pyridyl)-2-(4-fluoro-phenyl)-7-aza-indole (40) after preparative plate chromatography: Mass Spectrum (CI) 518 (MH+).

EXAMPLE 22

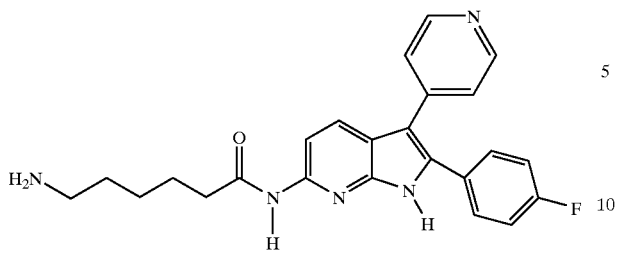

6-(6'-Amino-1'-oxo-hexylamino)-3-(4-pyridyl)-2-(4-fluorophenyl)-7-aza-indole (41)

Compound (41) was prepared from compound (40) in the manner of example 6 which afforded 6-(6'-amino-1'-oxo-hexylamino)-3-(4-pyridyl)-2-(4-fluorophenyl)-7-aza-indole (41): Mass Spectrum (CI) 418 (MH+).

EXAMPLE 23

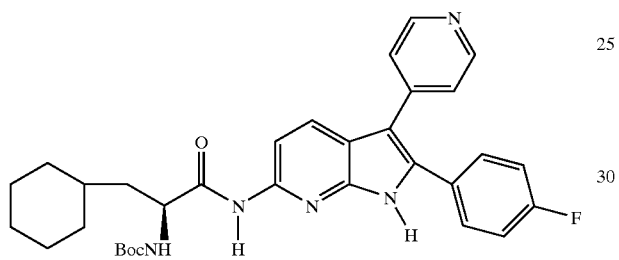

6-(3'-Cyclohexyl-1'-oxo-2'-t-butoxycarbonylaminopropylamino)-3-(4-pyridyl)-2-(4-fluorophenyl)-7-aza-indole (42)

Compound (42) was prepared in the manner of example 5 with the following substitution: N-a-t-Boc-b-cyclohexylalanine was used in place of N-t-Boc-g-aminobutyric acid which afforded 6-(3'-cyclohexyl-1'-oxo-2'-t-butoxycarbonylaminopropylamino)-3-(4-pyridyl)-2-(4-fluorophenyl)-7-aza-indole (42) after preparative plate chromatography: Mass Spectrum (CI) 558 (MH+).

EXAMPLE 24

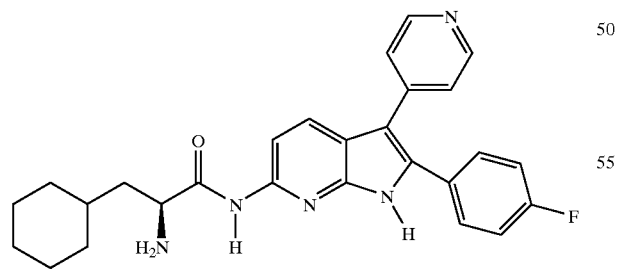

6-(3'-Cyclohexyl-1'-oxo-2'-aminopropylamino)-3-(4-pyridyl)-2-(4-fluorophenyl)-7-aza-indole (43)

Compound (43) was prepared from compound (42) in the manner of example 6 which afforded 6-(3'-cyclohexyl-1'-oxo-2'-aminopropylamino)-3- (4-pyridyl)-2-(4-fluorophenyl)-7-aza-indole (43): Mass Spectrum (CI) 458 (MH–).

EXAMPLE 25

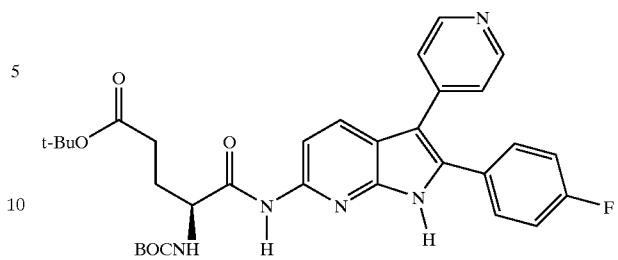

6-(4'-t-Butoxycarbonyl-1-oxo-2'-t-butoxycarbonylaminobutylamino)-3-(4-pyridyl)-2-(4-fluorophenyl)-7-aza-indole (44)

Compound (44).was prepared in the manner of example 5 with the following substitution: N-a-t-Boc-b-t-butylglutamic acid was used in place of N-t-Boc-g-aminobutyric acid which afforded 6-(4'-t-butoxycarbonyl-1'-oxo-2'-t-butoxycarbonylaminobutylamino)-3-(4-pyridyl)-2-(4-fluorophenyl)-7-aza-indole (44) after preparative plate chromatography: Mass Spectrum (CI) 590 (MH+).

EXAMPLE 26

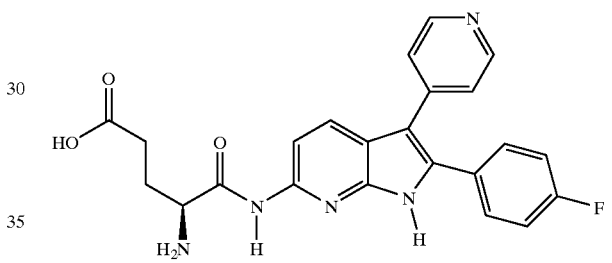

6-(4'-Carboxy-1'-oxo-2'-aminobutylamino)-3-(4-pyridyl)-2-(4-fluorophenyl)-7-aza-indole (45)

Compound (45) was prepared from compound (44) in the manner of example 6 which afforded 6-(4'-carboxy-1'-oxo-2'-aminobutylamino)-3-(4-pyridyl)-2-(4-fluorophenyl)-7-aza-indole (45): Mass Spectrum (CI) 434 (MH+).

EXAMPLE 27

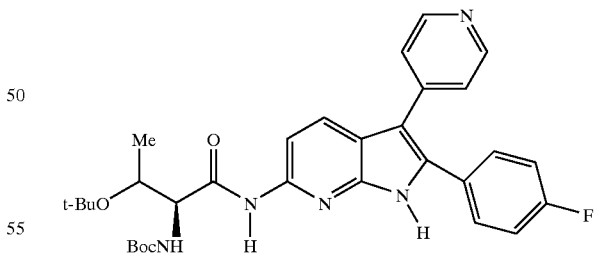

6-(3'-O-t-Butoxy-1'-oxo-2'-t-butoxycarbonylaminobutylamino)-3-(4-pyridyl)-2-(4-fluorophenyl)-7-aza-indole (46)

Compound (46) was prepared in the manner of example 5 with the following substitution: N-a-t-Boc-O-t-butylthreonine was used in place of N-t-Boc-g-aminobutyric acid which afforded 6-(3'-O-t-butoxy-1'-oxo-2'-t-butoxycarbonylaminobutylamino)-3-(4-pyridyl)-2-(4-fluorophenyl)-7-aza-indole (46) after preparative plate chromatography: Mass Spectrum (CI) 562 (MH+).

EXAMPLE 28

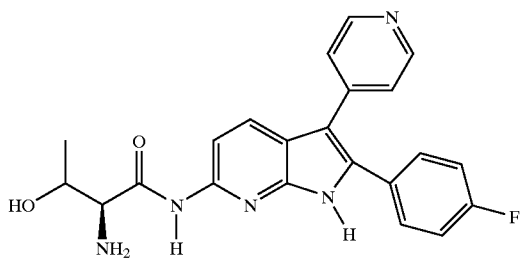

6-(3'-Hydroxy-1'-oxo-2'-aminobutylamino)-3-(4-pyridyl)-2-(4-fluorophenyl)-7-aza-indole (47)

Compound (47) was prepared from compound (46) in the manner of example 6 which afforded 6-(3'-hydroxy-1'-oxo-2'-aminobutylamino)-3-(4-pyridyl)-2-(4-fluorophenyl)-7-aza-indole (47): Mass Spectrum (CI) 406 (MH+).

EXAMPLE 29

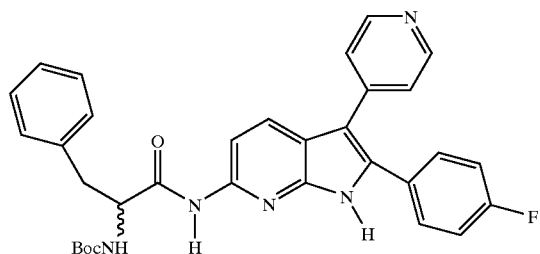

6-(3'-Phenyl-1'-oxo-2'-t-butoxycarbonylaminopropylamino)-3-(4-pyridyl)-2-(4-fluorophenyl)-7-aza-indole (48)

Compound (48) was prepared in the manner of example 5 with the following substitution: N-a-t-Boc-D,L-phenylalanine was used in place of N-t-Boc-g-aminobutyric acid which afforded 6-(3'-O-t-butoxy-1'-oxo-2'-t-butoxycarbonylaminobutylamino)-3-(4-pyridyl)-2-(4-fluorophenyl)-7-aza-indole (46) after preparative plate chromatography: Mass Spectrum (CI) 552 (MH+).

EXAMPLE 30

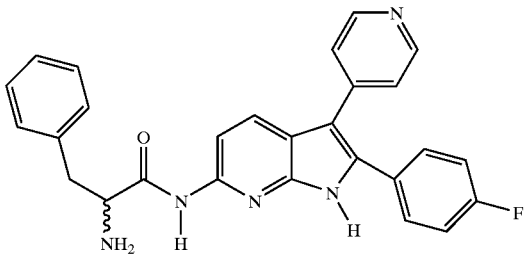

6-(3'-Phenyl-1'-oxo-2'-D,L-aminopropylamino)-3-(4-pyridyl)-2-(4-fluorophenyl)-7-aza-indole (49)

Compound (49) was prepared from compound (48) in the manner of example 6 which afforded 6-(3'-phenyl-1'-oxo-2'-aminopropylamino)-3-(4-pyridyl)-2-(4-fluorophenyl)-7-aza-indole (49): Mass Spectrum (CI) 452 (MH+).

EXAMPLE 31

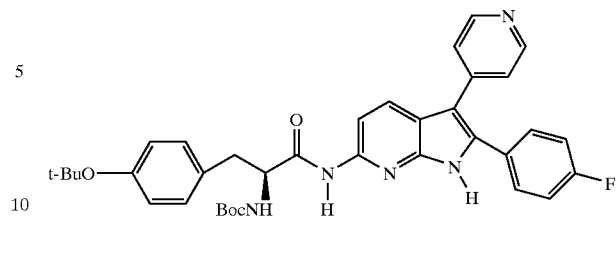

6-(3'-(4-t-Butoxyphenyl)-1'-oxo-2'-t-butoxycarbonylaminopropylamino)-3-(4-pyridyl)-2-(4-fluorophenyl)-7-aza-indole (50)

Compound (50) was prepared in the manner of example 5 with the following substitution: N-a-t-Boc-O-t-butyltyrosine was used in place of N-t-Boc-g-aminobutyric acid which afforded 6-(3'-(4-t-Butoxyphenyl)-1'-oxo-2'-t-butoxycarbonylaminopropyl amino)-3-(4-pyridyl)-2-(4-fluorophenyl)-7-aza-indole (50) after preparative plate chromatography: Mass Spectrum (CI) 624 (MH+).

EXAMPLE 32

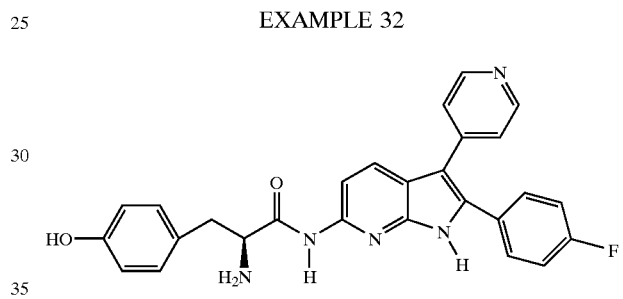

6-(3'-(4-Hydroxyphenyl)-1'-oxo-2'-aminopropylamino)-3-(4-pyridyl)-2-(4-fluorophenyl)-7-aza-indole (51)

Compound (51) was prepared from compound (50) in the manner of example 6 which afforded 6-(3'-(4-hydroxyphenyl)-1'-oxo-2'-aminopropylamino)-3-(4-pyridyl)-2-(4-fluorophenyl)-7-aza-indole (51): Mass Spectrum (CI) 468 (MH+).

EXAMPLE 33

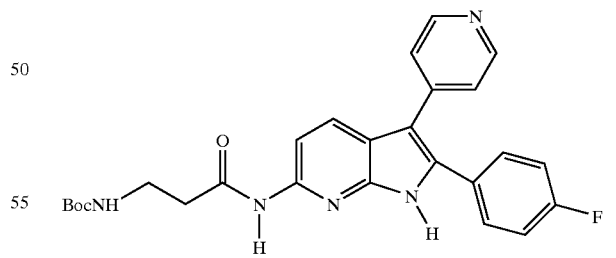

6-(3'-t-Butoxycarbonylamino-1'-oxo-propylamino)-3-(4-pyridyl)-2-(4-fluorophenyl)-7-aza-indole (52)

Compound (52) was prepared in the manner of example 5 with the following substitution: N-Boc-b-alanine was used in place of N-t-Boc-g-aminobutyric acid which afforded 6-(3'-t-butoxycarbonylamino-1'-oxo-propylamino)-3-(4-pyridyl)-2-(4-fluorophenyl)-7-aza-indole (52) after preparative plate chromatography: Mass Spectrum (CI) 476 (MH+).

EXAMPLE 34

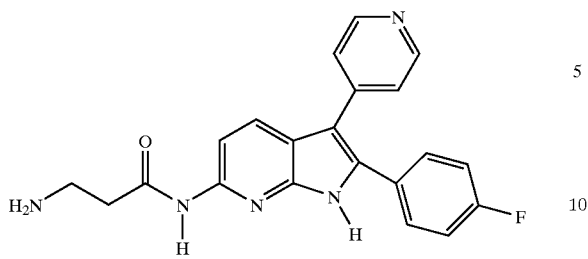

6-(3'-Amino-1'-oxo-propylamino)-3-(4-pyridyl)-2-(4-fluorophenyl)-7-aza-indole (53)

Compound (53) was prepared from compound (52) in the manner of example 6 which afforded 6-(3'-amino-1'-oxo-propylamino)-3-(4-pyridyl)-2-(4-fluorophenyl)-7-aza-indole (53): Mass Spectrum (CI) 376 (MH+).

EXAMPLE 35

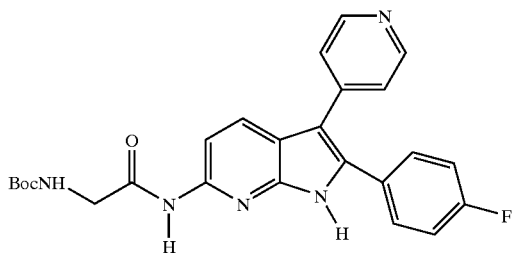

6-(2'-t-Butoxycarbonylamino-1'-oxo-ethylamino)-3-(4-pyridyl)-2-(4-fluorophenyl)-7-aza-indole (54)

Compound (54) was prepared in the manner of example 5 with the following substitution: N-Boc-glycine was used in place of N-t-Boc-g-aminobutyric acid which afforded 6-(2'-t-butoxycarbonylamino-1'-oxo-ethylamino)-3-(4-pyridyl)-2-(4-fluorophenyl)-7-aza-indole (54) after preparative plate chromatography: Mass Spectrum (CI) 461 (MH+).

EXAMPLE 36

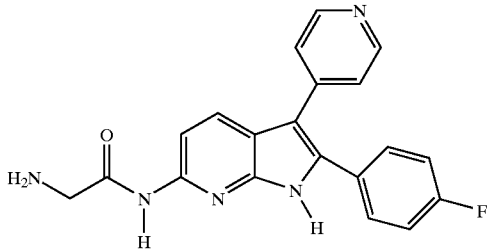

6-(2'-Amino-1'-oxo-ethylamino)-3-(4-pyridyl)-2-(4-fluorophenyl)-7-aza-indole (55)

An HCl dioxane solution (4N, anhydrous, 0.27 mL) was added to 6-(2'-t-butoxycarbonylamino-1'-oxo-ethylamino)-3-(4-pyridyl)-2-(4-fluoro-phenyl)-7-aza-indole (54) (50.0 mg, 0.11 mmol), anisole (59 ml, 0.55 mmol), and dioxane (4 mL) in one portion. After 30 min at 23° C., the reaction was concentrated with a stream of nitrogen in a hood. The residue was diluted with saturated bicarbonate (30 mL), extracted with ethyl acetate (3×50 mL), and dried (Na$_2$SO$_4$). After concentration in vacuo, the residue was purified by application of preparative plate chromatography (two 2 mm silica gel plates, ethyl acetate: methanol 19:1) to afford 6-(2'-amino-1-oxo-ethylamino)-3-(4-pyridyl)-2-(4-fluoro phenyl)-7-aza-indole (55): Mass Spectrum (CI) 362 (MH$^+$).

EXAMPLE 37

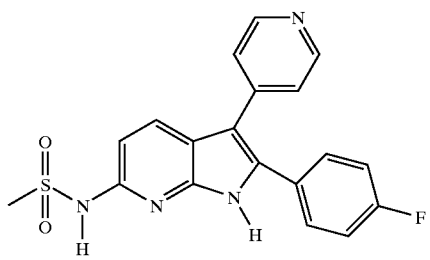

6-(Methylsulfonylamino)-3-(4-pyridyl)-2-(4-fluorophenyl)-7-aza-indole (56)

Methanesulfonyl chloride (5 ml, 0.07 mmol) was added dropwise to 6-amino-3-(4-pyridyl)-2-(4-fluorophenyl)-7-aza-indole (17) (20 mg, 0.066 mmol), dimethylamino pyridine (1 mg, 0.007 mmol), and chloroform (3 mL). After 24 h at 23° C., an additional 4 equivalents of methanesulfonyl chloride was added. After 4 h at 23° C., NaOH (10N, 3 mL) was added. After 3 h, the mixture was extracted with ethyl acetate (50 mL), washed with water (3×15 mL), and dried (Na$_2$SO$_4$). After concentration in vacuo, the residue was purified by application of preparative plate chromatography (two 2 mm silica gel plates, ethyl acetate) to afford 6-(methylsulfonyl amino)-3-(4-pyridyl)-2-(4-fluorophenyl)-7-aza-indole (56): Mass Spectrum (CI) 383 (MH$^+$).

EXAMPLE 38

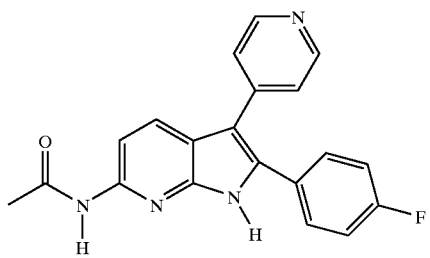

6-(1'-oxo-ethylamino)-3-(4-pyridyl)-2-(4-fluorophenyl)-7-aza-indole (57)

6-Amino-3-(4-pyridyl)-2-(4-fluorophenyl)-7-aza-indole (17) (50 mg, 0.164 mmol) and acetic anhydride (0.5 mL) were warmed to 60° C. for 1 h. After cooling to 23° C., the reaction was diluted with ethyl acetate (50 mL), washed with NaOH (1 N, 50 mL), and dried (Na$_2$SO$_4$). Concentration in vacuo afforded 6-(1'-oxo-ethylamino)-3-(4-pyridyl)-2-(4-fluorophenyl)-7-aza-indole (57): Mass Spectrum (CI) 347 (MH$^+$).

EXAMPLE 39

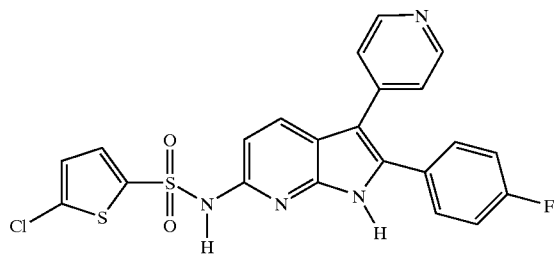

6-(2'-(5-Chlorothienyl)sulfonylamino)-3-(4-pyridyl)-2-(4-fluorophenyl)-7-aza-indole (58)

Compound (58) was prepared in the manner of example 37 with the following substitution: 5-chlorothienyl-2-sulfonyl chloride (4 equivalents) was used in place of methanesulfonyl chloride which afforded 6-(2'-(5-chlorothienyl)sulfonylamino)-3-(4-pyridyl)-2-(4-fluorophenyl)-7-aza-indole (58) after preparative plate chromatography: Mass Spectrum (CI) 485 (MH+).

EXAMPLE 40

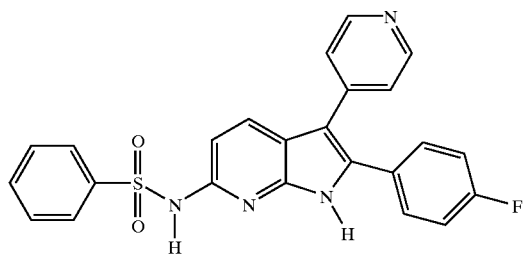

6-(Phenylsulfonylamino)-3-(4-pyridyl)-2-(4-fluorophenyl)-7-aza-indole (59)

Compound (59) was prepared in the manner of example 37 with the following substitution: phenylsulfonyl chloride (4 equivalents) was used in place of methanesulfonyl chloride which afforded 6-(2'-(5-chlorothienyl)sulfonylamino)-3-(4-pyridyl)-2-(4-fluorophenyl)-7-aza-indole (58) after preparative plate chromatography: Mass Spectrum (CI) 445 (MH+).

EXAMPLE 41

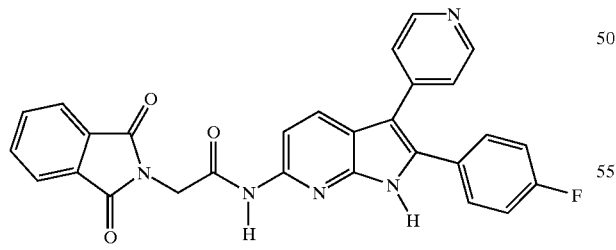

6-(2'-N-Phthaloyl-1'-oxo-ethylamino)-3-(4-pyridyl)-2-(4-fluorophenyl)-7-aza-indole (60)

Compound (60) was prepared in the manner of example 5 with the following substitution: N-phthaloylglycine was used in place of N-t-Boc-g-aminobutyric acid which afforded 6-(2'-N-Phthaloyl-1'-oxo-ethylamino)-3-(4-pyridyl)-2-(4-fluorophenyl)-7-aza-indole (60) after preparative plate chromatography: Mass Spectrum (CI) 492 (MH+).

EXAMPLE 42

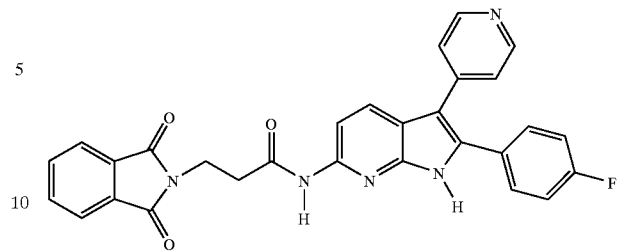

6-(3'-N-Phthaloyl-1'-oxo-propylamino)-3-(4-pyridyl)-2-(4-fluorophenyl)-7-aza-indole (61)

Compound (60) was prepared in the manner of example 5 with the following substitution: N-phthaloyl-b-alanine was used in place of N-t-Boc-g-aminobutyric acid which afforded 6-(2'-N-Phthaloyl-1'-oxo-ethylamino)-3-(4-pyridyl)-2-(4-fluorophenyl)-7-aza-indole (61) after preparative plate chromatography: Mass Spectrum (CI) 506 (MH+).

EXAMPLE 43

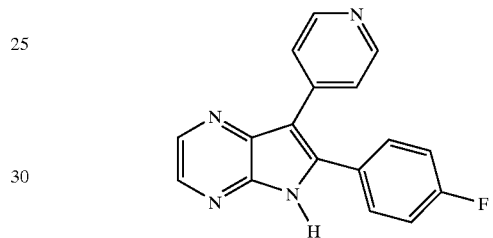

3-(4-Pyridyl)-2-(4-fluorophenyl)-4,7-diaza-indole (62)

1-(4-Fluorophenyl)-2-t-butyldimethylsiloxy-2-(4-pyridyl) ethanone (16) (5.44 g, 15.77 mmol), 2-aminopyrazine (1.00 g, 10.5 mmol), and concentrated HCl (30 mL) were heated in a sealed tube to 190° C. behind an explosion shield. After 3 h at 190° C., the reaction was allowed to cool to 23° C. then diluted with water (100 mL). After further dilution with concentrated ammonium hydroxide to pH of 12, the reaction was extracted with methylene chloride (3×200 mL), and dried (MgSO4). After concentration in vacuo, the residue was purified by applying flash chromatography (100% ethyl acetate) to afford 3-(4-pyridyl)-2-(4-fluorophenyl)-4,7-diaza-indole (62): Mass Spectrum (CI) 291 (MH+).

EXAMPLE 44

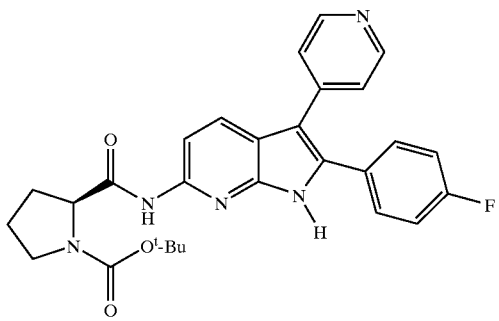

6-(2'-N-t-Butoxycarbonyl-L-prolylamino)-3-(4-pyridyl)-2-(4-fluorophenyl)-7-aza-indole (63)

Compound (63) was prepared in the manner of example 5 with the following substitution: N-t-Boc-proline was used in place of N-t-Boc-g-aminobutyric acid which afforded 6-(2'-N-t-Butoxycarbonyl-L-prolylamino)-3-(4-pyridyl)-2-(4-fluorophenyl)-7-aza-indole (63) after preparative plate chromatography: Mass Spectrum (CI) 502 (MH⁺).

EXAMPLE 45

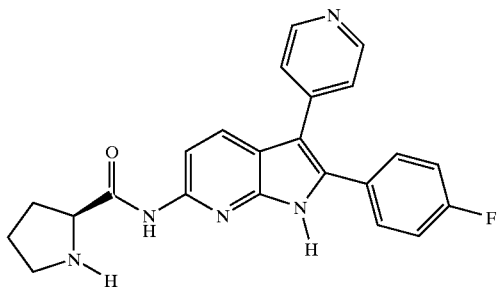

6-(2'-L-Prolylamino)-3-(4-pyridyl)-2-(4-fluorophenyl)-7-aza-indole (64)

Compound (64) was prepared from compound (63) in the manner of example 6 which afforded 6-(2'-L-prolylamino)-3-(4-pyridyl)-2-(4-fluorophenyl)-7-aza-indole (64): Mass Spectrum (CI) 402 (MH+).

EXAMPLE 46

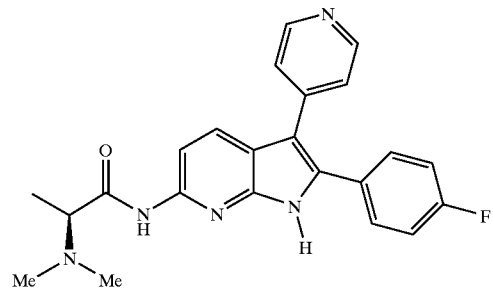

6-(2S'-Dimethylamino-1'-oxo-propylamino)-3-(4-pyridyl)-2-(4-fluorophenyl)-7-aza-indole (65)

Compound (65) was prepared in the manner of example 5 with the following substitution: N,N-dimethylalanine was used in place of N-t-Boc-g-aminobutyric acid which afforded 6-(2'-Dimethylamino-1'-oxo-propylamino)-3-(4-pyridyl)-2-(4-fluorophenyl)-7-aza-indole (65) after preparative plate chromatography: Mass Spectrum (CI) 404 (MH⁺).

EXAMPLE 47

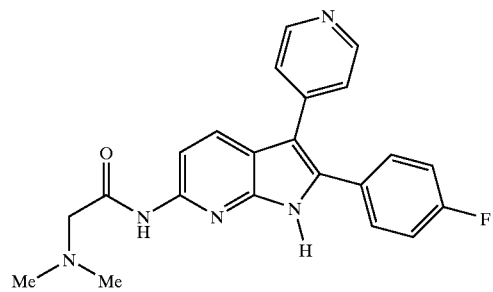

6-(2'-Dimethylamino-1'-oxo-ethylamino)-3-(4-pyridyl)-2-(4-fluorophenyl)-7-aza-indole (66)

Compound (66) was prepared in the manner of example 5 with the following substitution: N,N-dimethylglycine was used in place of N-t-Boc-g-aminobutyric acid which afforded 6-(2'-Dimethylamino-1'-oxo-ethylamino)-3-(4-pyridyl)-2-(4-fluorophenyl)-7-aza-indole (66) after preparative plate chromatography: Mass Spectrum (CI) 389 (MH⁺).

EXAMPLE 48

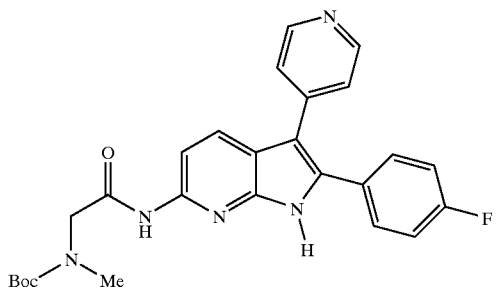

6-(2'-N-Methyl-t-butoxycarbonylamino-1'-oxo-ethylamino)-3-(4-pyridyl)-2-(4-fluorophenyl)-7-aza-indole (67)

Compound (67) was prepared in the manner of example 5 with the following substitution: N-Boc-N-methyl-glycine was used in place of N-t-Boc-g-aminobutyric acid which afforded 6-(2'-N-Methyl-t-butoxycarbonylamino-1'-oxo-ethylamino)-3-(4-pyridyl)-2-(4-fluorophenyl)-7-aza-indole (67) after preparative plate chromatography: Mass Spectrum (CI) 476 (MH+).

EXAMPLE 49

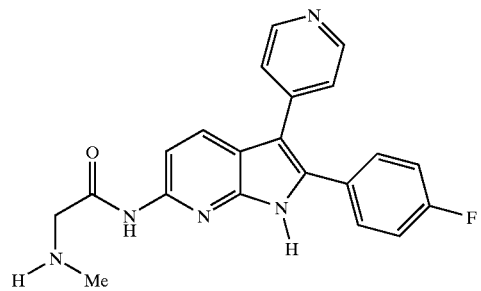

6-(2'-N-Methyl-amino-1'-oxo-ethylamino)-3-(4-pyridyl)-2-(4-fluorophenyl)-7-aza-indole (68)

Compound (68) was prepared from compound (67) in the manner of example 6 which afforded 6-(2'-N-Methyl-amino-1'-oxo-ethylamino)-3-(4-pyridyl)-2-(4-fluorophenyl)-7-aza-indole (68): Mass Spectrum (CI) 376 (MH+).

EXAMPLE 50

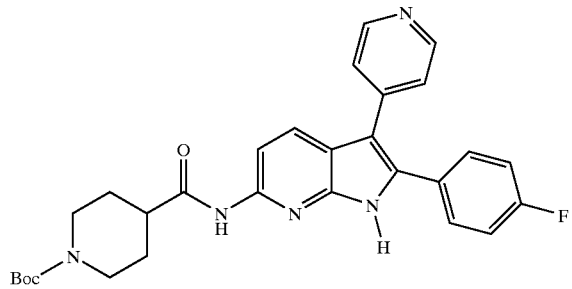

6-(4'-N-t-Butoxycarbonylisonipecotylamino)-3-(4-pyridyl)-2-(4-fluorophenyl)-7-aza-indole (69)

Compound (69) was prepared in the manner of example 5 with the following substitution: N-Boc-isonipecotic acid was used in place of N-t-Boc-g-aminobutyric acid which afforded 6-(4'-N-t-Butoxycarbonylisonipecotylamino)-3-(4-pyridyl)-2-(4-fluorophenyl)-7-aza-indole (69) after preparative plate chromatography: Mass Spectrum (CI) 516 (MH+).

EXAMPLE 51

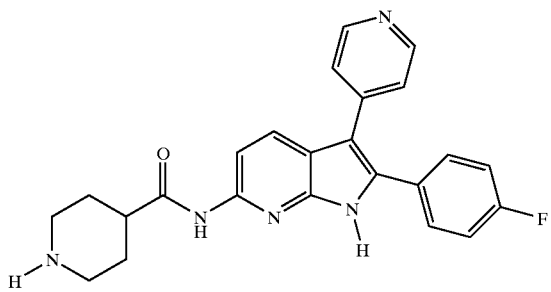

6-(4'-Isonipecotylamino)-3-(4-pyridyl)-2-(4-fluorophenyl)-7-aza-indole (70)

Compound (70) was prepared from compound (69) in the manner of example 6 which afforded 6-(4'-isonipecotylamino)-3-(4-pyridyl)-2-(4-fluorophenyl)-7-aza-indole (70): Mass Spectrum (CI) 416 (MH+).

EXAMPLE 52

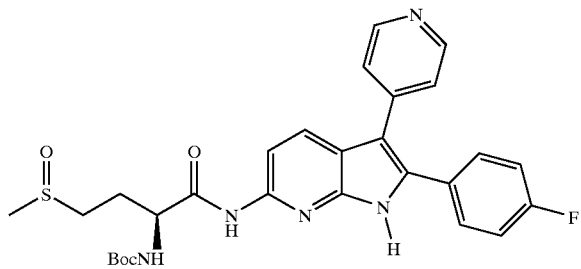

6-(4'-Methylsulfoxo-1'-oxo-2'S-t-butoxycarbonylaminobutylamino)-3-(4-pyridyl)-2-(4-fluorophenyl)-7-aza-indole (71)

Compound (69) was prepared in the manner of example 5 with the following substitution: N-Boc-L-methionine sulfoxide (diasteromeric mixture) was used in place of N-t-Boc-g-aminobutyric acid which afforded 6-(4'-methylsulfoxo-1'-oxo-2'S-t-butoxycarbonylaminobutylamino)-3-(4-pyridyl)-2-(4-fluorophenyl)-7-aza-indole (71) after preparative plate chromatography: Mass Spectrum (CI) 552 (MH+).

EXAMPLE 53

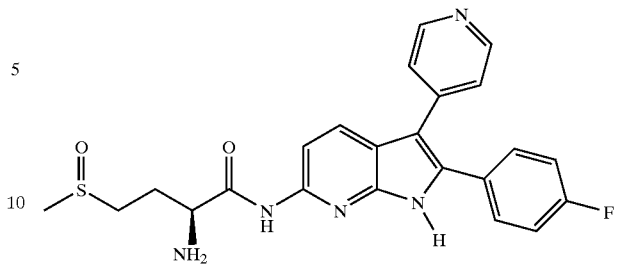

6-(4'-Methylsulfoxo-1'-oxo-2'S-aminobutylamino)-3-(4-pyridyl)-2-(4-fluorophenyl)-7-aza-indole (72)

Compound (72) was prepared from compound (71) in the manner of example 6 which afforded 6-(4'-methylsulfoxo-1'-oxo-2'S-aminobutylamino)-3-(4-pyridyl)-2-(4-fluorophenyl)-7-aza-indole (72): Mass Spectrum (CI) 452 (MH+).

EXAMPLE 54

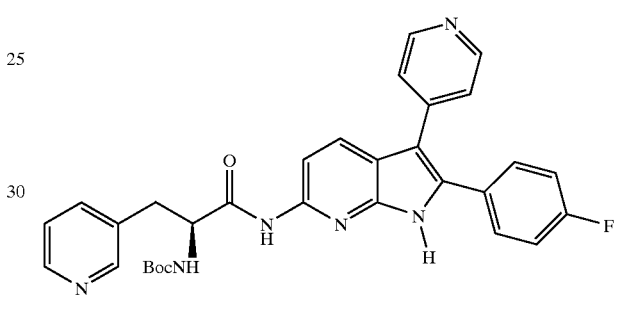

6-(3'-(3-pyridyl)-1'-oxo-2'S-t-butoxycarbonylaminopropylamino)-3-(4-pyridyl)-2-(4-fluorophenyl)-7-aza-indole (73)

Compound (73) was prepared in the manner of example 5 with the following substitution: N-Boc-L-b-(3-pyridyl)-alanine was used in place of N-t-Boc-g-aminobutyric acid which afforded 6-(3'-(3-pyridyl)-1'-oxo-2'S-t-butoxycarbonylaminobutylamino)-3-(4-pyridyl)-2-(4-fluorophenyl)-7-aza-indole (73) after preparative plate chromatography: Mass Spectrum (CI) 553 (MH+).

EXAMPLE 55

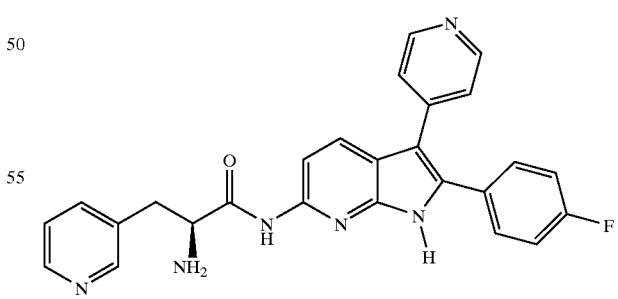

6-(3'-(3-Pyridyl)-1'-oxo-2'S-aminopropylamino)-3-(4-pyridyl)-2-(4-fluorophenyl)-7-aza-indole (74)

Compound (74) was prepared from compound (73) in the manner of example 6 which afforded 6-(3'-(3-pyridyl)-1'-oxo-2'S-aminopropylamino)-3-(4-pyridyl)-2-(4-fluorophenyl)-7-aza-indole (74): Mass Spectrum (CI) 453 (MH+).

EXAMPLE 56

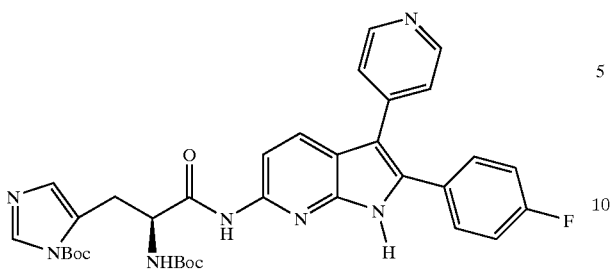

6-(N,N-Di-t-Butoxycarbonyl-L-histidinylamino)-3-(4-pyridyl)-2-(4-fluorophenyl)-7-aza-indole (75)

Compound (73) was prepared in the manner of example 5 with the following substitution: 2'-N,N-Di-t-Butoxycarbonyl-L-histidine was used in place of N-t-Boc-g-aminobutyric acid which afforded 6-(2'-N,N-Di-t-Butoxycarbonyl-L-histidinyl)-3-(4-pyridyl)-2-(4-fluorophenyl)-7-aza-indole (75) after preparative plate chromatography: Mass Spectrum (CI) 642 (MH+).

EXAMPLE 57

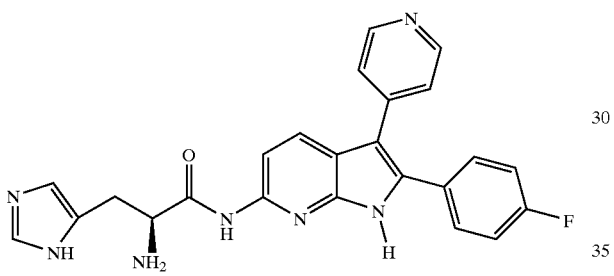

6-(L-Histidinylamino)-3-(4-pyridyl)-2-(4-fluorophenyl)-7-aza-indole (76)

Compound (76) was prepared from compound (75) in the manner of example 6 which afforded 6-(L-histidinylamino)-3-(4-pyridyl)-2-(4-fluorophenyl)-7-aza-indole (76): Mass Spectrum (CI) 542 (MH+).

EXAMPLE 58

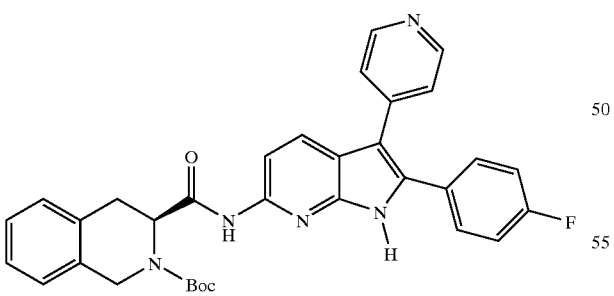

6-(N-t-Butoxycarbonyl-3(S) 1',2',3',4'-tetrahydro-3'-isoquinolinyloxo-amino)-3-(4-pyridyl)-2-(4-fluorophenyl)-7-aza-indole (114)

Compound (114) was prepared in the manner of example 5 with the following substitution: N-t-Butoxycarbonyl-3(S) 1,2,3,4-tetrahydro-3-isoquinolinylcarboxylic acid was used in place of N-t-Boc-g-aminobutyric acid which afforded 6-(N-t-Butoxycarbonyl-3(S) 1',2',3',4'-tetrahydro-3'-isoquinolinyloxo-amino)-3-(4-pyridyl)-2-(4-fluorophenyl)-7-aza-indole (114) after preparative plate chromatography: Mass Spectrum (CI) 564 (MH+).

EXAMPLE 59

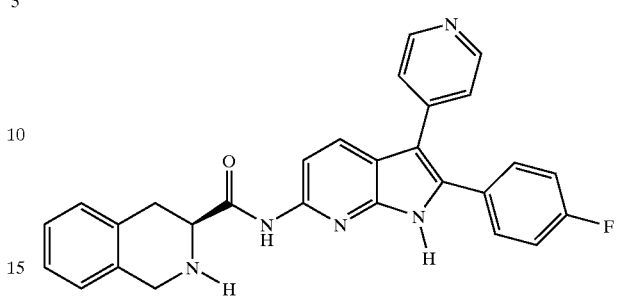

6-(3(S) 1',2',3',4'-Tetrahydro-3'-isoquinolinyloxoamino)-3-(4-pyridyl)-2-(4-fluorophenyl)-7-aza-indole (115)

Compound (115) was prepared from compound (114) in the manner of example 6 which afforded 6-(3(S) 1',2',3',4'-tetrahydro-3'-isoquinolinyloxoamino)-3-(4-pyridyl)-2-(4-fluorophenyl)-7-aza-indole (115): Mass Spectrum (CI) 464 (MH+).

EXAMPLE 60

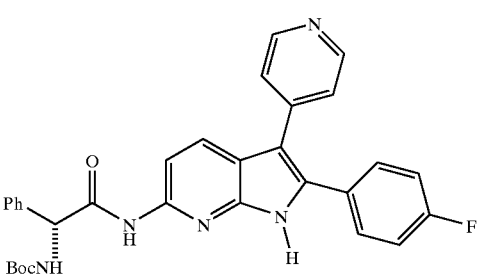

6-(2'-Phenyl-1'-oxo-2'R-N-t-butoxycarbonylaminoethylamino)-3-(4-pyridyl)-2-(4-fluorophenyl)-7-aza-indole (116)

Compound (116) was prepared in the manner of example 5 with the following substitution: N-Boc-R-phenylglycine was used in place of N-t-Boc-g-aminobutyric acid which afforded 6-(2'-phenyl-1'-oxo-2'R-N-t-butoxycarbonylamino ethylamino)-3-(4-pyridyl)-2-(4-fluorophenyl)-7-aza-indole (116) after preparative plate chromatography: Mass Spectrum (CI) 538 (MH+).

EXAMPLE 61

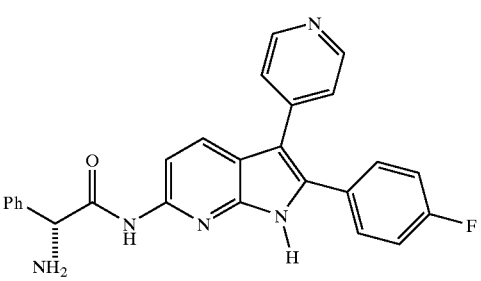

6-(2'-Phenyl-1'-oxo-2'R-aminoethylamino)-3-(4-pyridyl)-2-(4-fluorophenyl)-7-aza-indole (117)

Compound (117) was prepared from compound (116) in the manner of example 6 which afforded 6-(2'-phenyl-1'- oxo-2'R-aminoethylamino)-3-(4-pyridyl)-2-(4-fluorophenyl)-7-aza-indole (117): Mass Spectrum (CI) 438 (MH+).

EXAMPLE 62

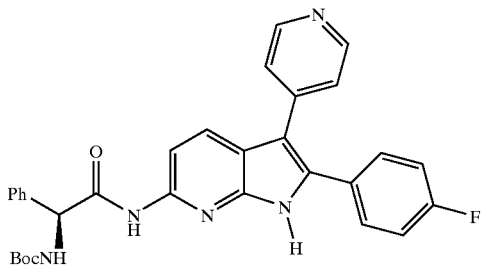

6-(2'-Phenyl-1'-oxo-2'S-N-t-butoxycarbonylaminoethylamino)-3-(4-pyridyl)-2-(4-fluorophenyl)-7-aza-indole (118)

Compound (118) was prepared in the manner of example 5 with the following substitution: N-Boc-S-phenylglycine was used in place of N-t-Boc-g-aminobutyric acid which afforded 6-(2'-phenyl-1'-oxo-2'S-N-t-butoxycarbonylamino ethylamino)-3-(4-pyridyl)-2-(4-fluorophenyl)-7-aza-indole (118) after preparative plate chromatography: Mass Spectrum (CI) 538 (MH+).

EXAMPLE 63

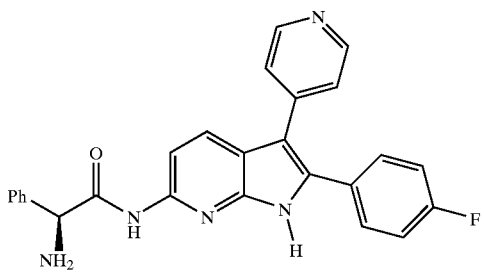

6-(2'-Phenyl-1'-oxo-2'S-aminoethylamino)-3-(4-pyridyl)-2-(4-fluorophenyl)-7-aza-indole (119)

Compound (119) was prepared from compound (118) in the manner of example 6 which afforded 6-(2'-phenyl-1'-oxo-2'S-aminoethylamino)-3-(4-pyridyl)-2-(4-fluorophenyl)-7-aza-indole (119): Mass Spectrum (CI) 438 (MH+).

EXAMPLE 64

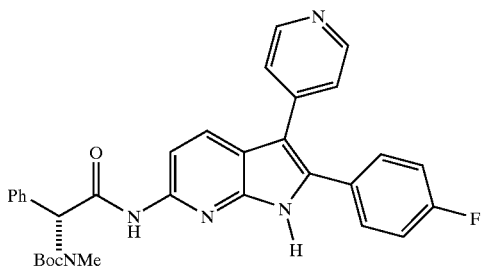

6-(2'-Phenyl-1'-oxo-2'R-N-t-butoxycarbonyl-N-methylamino ethylamino)-3-(4-pyridyl)-2-(4-fluorophenyl)-7-aza-indole (120)

Compound (120) was prepared in the manner of example 5 with the following substitution: N-Boc-R-N-methylphenyl glycine was used in place of N-t-Boc-g-aminobutyric acid which afforded 6-(2'-phenyl-1'-oxo-2'R-N-t-butoxy carbonyl-N-methylaminoethylamino)-3-(4-pyridyl)-2-(4-fluorophenyl)-7-aza-indole (120) after preparative plate chromatography: Mass Spectrum (CI) 552 (MH+).

EXAMPLE 65

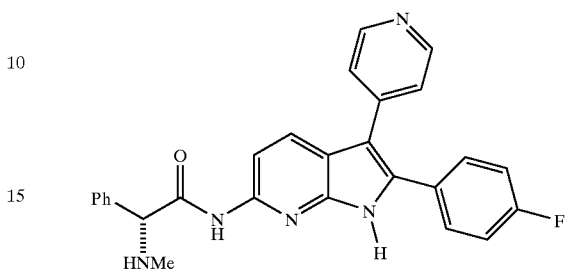

6-(2'-Phenyl-1'-oxo-2'R-N-methylaminoethylamino)-3-(4-pyridyl)-2-(4-fluorophenyl)-7-aza-indole (121)

Compound (121) was prepared from compound (120) in the manner of example 6 which afforded 6-(2'-phenyl-1'-oxo-2'R-N-methylaminoethylamino)-3-(4-pyridyl)-2-(4-fluoro phenyl)-7-aza-indole (121): Mass Spectrum (CI) 452 (MH+).

EXAMPLE 66

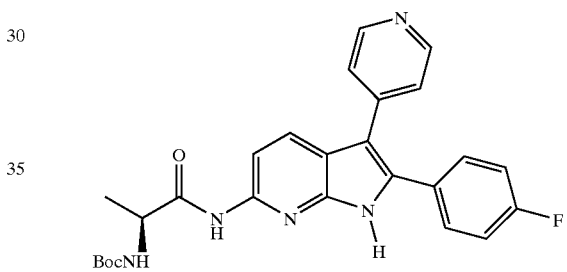

6-(1'-oxo-2'S-t-Butoxycarbonylaminopropylamino)-3-(4-pyridyl)-2-(4-fluorophenyl)-7-aza-indole (122)

Compound (122) was prepared in the manner of example 5 with the following substitution: N-Boc-L-alanine was used in place of N-t-Boc-g-aminobutyric acid which afforded 6-(1'-oxo-2'S-t-butoxycarbonylaminopropyl amino)-3-(4-pyridyl)-2-(4-fluorophenyl)-7-aza-indole (122) after preparative plate chromatography: Mass Spectrum (CI) 476 (MH+).

EXAMPLE 67

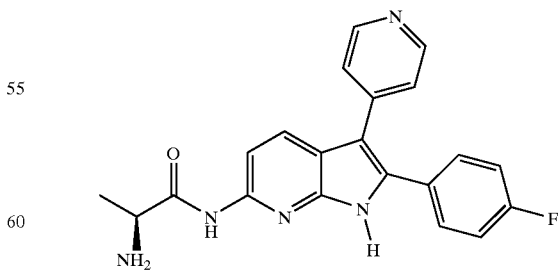

6-(1'-oxo-2'S-Aminopropylamino)-3-(4-pyridyl)-2-(4-fluorophenyl)-7-aza-indole (123)

Compound (123) was prepared from compound (122) in the manner of example 6 which afforded 6-(1'-oxo-2'S- aminopropylamino)-3-(4-pyridyl)-2-(4-fluorophenyl)-7-aza-indole (123): Mass Spectrum (CI) 376 (MH⁺).

EXAMPLE 68

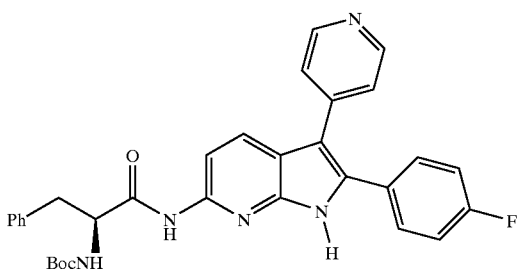

6-(3'-Phenyl-1'-oxo-2'-(L)-t-butoxycarbonylaminopropylamino)-3-(4-pyridyl)-2-(4-fluorophenyl)-7-aza-indole (124) Compound (124) was prepared in the manner of example 5 with the following substitution: N-Boc-L-phenylalanine was used in place of N-t-Boc-g-aminobutyric acid which afforded 6-(3'-phenyl-1'-oxo-2'-(L)-t-butoxycarbonyl aminopropylamino)-3-(4-pyridyl)-2-(4-fluorophenyl)-7-aza-indole (124) after preparative plate chromatography: Mass Spectrum (CI) 552 (MH⁺).

EXAMPLE 69

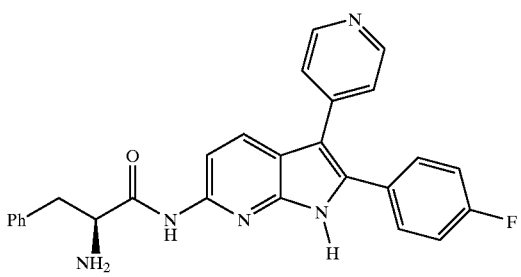

6-(3'-Phenyl-1'-oxo-2'-(L)-aminopropylamino)-3-(4-pyridyl)-2-(4-fluorophenyl)-7-aza-indole (125)

Compound (125) was prepared from compound (124) in the manner of example 6 which afforded 6-(3'-phenyl-1'-oxo-2'-(L)-aminopropylamino)-3-(4-pyridyl)-2-(4-fluorophenyl)-7-aza-indole (125):Mass Spectrum (CI) 452 (MH⁺).

EXAMPLE 70

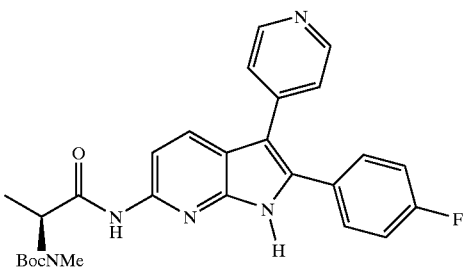

6-(1'-oxo-2'S-t-Butoxycarbonyl-N-methylaminopropylamino)-3-(4-pyridyl)-2-(4-fluorophenyl)-7-aza-indole (126)

Compound (126) was prepared in the manner of example 5 with the following substitution: N-Boc-L-N-methylalanine was used in place of N-t-Boc-g-aminobutyric acid which afforded 6-(3'-phenyl-1'-oxo-2¹-(L)-t-butoxycarbonyl aminopropylamino)-3-(4-pyridyl)-2-(4-fluorophenyl)-7-aza-indole (126) after preparative plate chromatography: Mass Spectrum (CI) 489 (MH+).

EXAMPLE 71

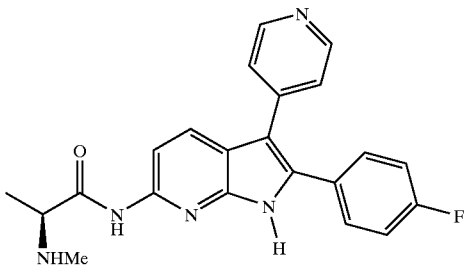

6-(1'-oxo-2'S-N-Methylaminopropylamino)-3-(4-pyridyl)-2-(4-fluorophenyl)-7-aza-indole (127)

Compound (127) was prepared from compound (126) in the manner of example 6 which afforded 6-(1-oxo-2'S-N-methylaminopropylamino)-3-(4-pyridyl)-2-(4-fluorophenyl)-7-aza-indole (127): Mass Spectrum (CI) 389 (MH⁺).

EXAMPLE 72

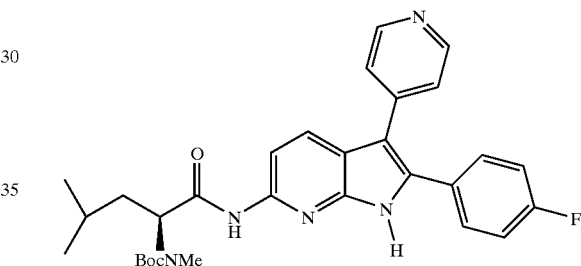

6-(1'-oxo-2'S-t-Butoxycarbonyl-N-methyl-4-methyl-2-aminopentyl-amino) -3-(4-pyridyl) -2-(4-fluorophenyl)-7-aza-indole (128)

Compound (128) was prepared in the manner of example 5 with the following substitution: N-Boc-L-N-methylleucine was used in place of N-t-Boc-g-aminobutyric acid which afforded 6-(1'-oxo-2'S-t-butoxycarbonyl-N-methyl-4-methyl-2-aminopentylamino)-3-(4-pyridyl)-2-(4-fluorophenyl)-7-aza-indole (128) after preparative plate chromatography: Mass Spectrum (CI) 532 (MH⁺).

EXAMPLE 73

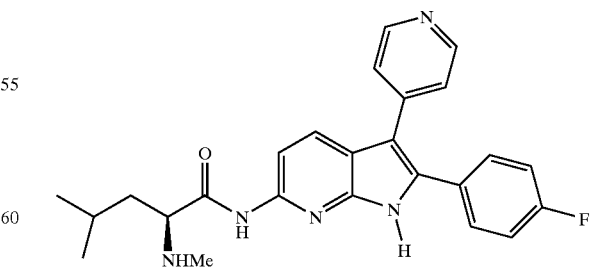

6-(1'-oxo-2'S-N-Methyl-4-methyl-2-aminopentylamino)-3-(4-pyridyl)-2-(4-fluorophenyl)-7-aza-indole (129)

Compound (129) was prepared from compound (128) in the manner of example 6 which afforded 6-(1'-oxo-2'S-N- methyl-4-methyl-2-aminopentylamino)-3-(4-pyridyl)-2-(4-fluorophenyl)-7-aza-indole (129): Mass Spectrum (CI) 432 (MH⁺).

EXAMPLE 74

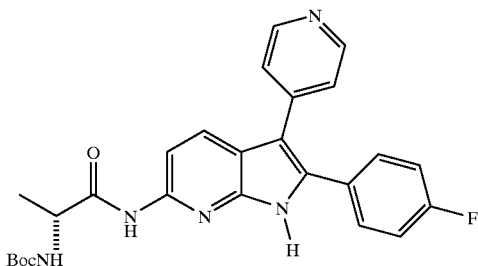

6-(1'-oxo-2'R-t-Butoxycarbonylaminopropylamino)-3-(4-pyridyl)-2-(4-fluorophenyl)-7-aza-indole (130)

Compound (130) was prepared in the manner of example 5 with the following substitution: N-Boc-D-alanine was used in place of N-t-Boc-g-aminobutyric acid which afforded 6-(1'-oxo-2'R-t-butoxycarbonylaminopropyl amino)-3-(4-pyridyl)-2-(4-fluorophenyl)-7-aza-indole (130) after preparative plate chromatography: Mass Spectrum (CI) 476 (MH⁺).

EXAMPLE 75

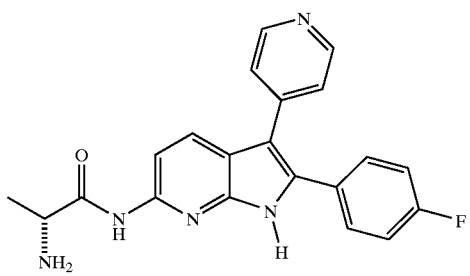

6-(1'-oxo-2'R-Aminopropylamino)-3-(4-pyridyl)-2-(4-fluorophenyl)-7-aza-indole (131)

Compound (131) was prepared from compound (130) in the manner of example 6 which afforded 6-(1'-oxo-2'R-aminopropylamino)-3-(4-pyridyl)-2-(4-fluorophenyl)-7-aza-indole (131): Mass Spectrum (CI) 376 (MH⁺).

EXAMPLE 76

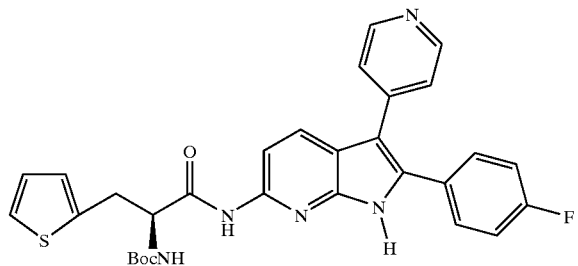

6-(3'-(2-Thienyl)-1'-oxo-2'-(L)-t-butoxycarbonylaminopropylamino)-3-(4-pyridyl)-2-(4-fluorophenyl)-7-aza-indole (132)

Compound (132) was prepared in the manner of example 5 with the following substitution: N-Boc-L-b-(2-thienyl) alanine was used in place of N-t-Boc-g-aminobutyric acid which afforded 6-(3'-(2-thienyl)-1'-oxo-2'-(L)-t-butoxycarbonylaminopropylamino)-3-(4-pyridyl)-2-(4-fluorophenyl)-7-aza-indole (132) after preparative plate chromatography: Mass Spectrum (CI) 558 (MH⁺).

EXAMPLE 77

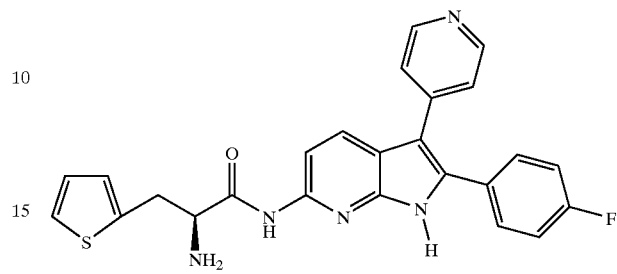

6-(3'-(2-Thienyl)-1'-oxo-2'-(L)-aminopropylamino)-3-(4-pyridyl)-2-(4-fluorophenyl)-7-aza-indole (133)

Compound (133) was prepared from compound (132) in the manner of example 6 which afforded 6-(3'-(2-thienyl)-1'-oxo-2'-(L)-aminopropylamino)-3-(4-pyridyl)-2-(4-fluorophenyl)-7-aza-indole (133): Mass Spectrum (CI) 458 (MH⁺).

EXAMPLE 78

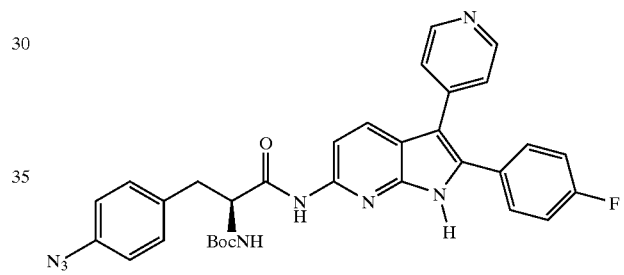

6-(3'-(4-Azidophenyl)-1'-oxo-2'S-t-butoxycarbonylaminopropylamino)-3-(4-pyridyl)-2-(4-fluorophenyl)-7-aza-indole (134)

Compound (134) was prepared in the manner of example 5 with the following substitution: (3'-(4-azidophenyl)-1'-oxo-2'S-t-butoxycarbonylaminopropionic acid was used in place of N-t-Boc-g-aminobutyric acid which afforded 6-(3'-(4-azidophenyl)-1'-oxo-2'S-t-butoxycarbonylamino propylamino)-3-(4-pyridyl)-2-(4-fluorophenyl)-7-aza-indole (134) after preparative plate chromatography: Mass Spectrum (CI) 609 (MH⁺).

EXAMPLE 79

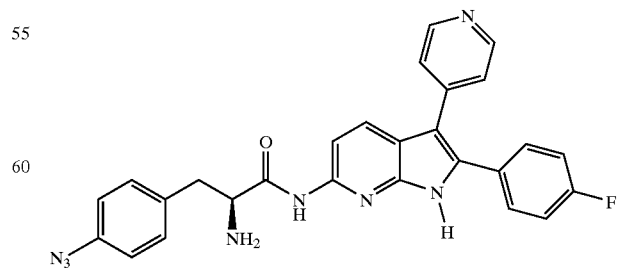

6-(3'-(4-Azidophenyl) -1'-oxo-2'S-aminopropylamino)-3-(4-pyridyl)-2-(4-fluorophenyl)-7-aza-indole (135)

Compound (135) was prepared from compound (134) in the manner of example 6 which afforded 6-(3'-(4-azidophenyl)-1'-oxo-2'S-aminopropylamino)-3-(4-pyridyl)-2-(4-fluoro phenyl)-7-aza-indole (135): Mass Spectrum (CI) 509 (MH+).

EXAMPLE 80

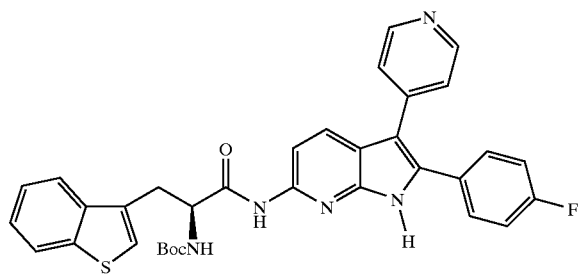

6-(3'-(3-Benzothienyl)-1'-oxo-2'S-t-butoxycarbonylaminopropylamino)-3-(4-pyridyl)-2-(4-fluorophenyl)-7-aza-indole (136)

Compound (136) was prepared in the manner of example 5 with the following substitution: 3-(3'-benzothienyl)-1-oxo-2S-t-butoxycarbonylaminopropionic acid was used in place of N-t-Boc-g-aminobutyric acid which afforded 6-(3'-(3-benzothienyl)-1'-oxo-2'S-t-butoxycarbonylaminopropylamino)-3-(4-pyridyl)-2-(4-fluorophenyl)-7-aza-indole (136) after preparative plate chromatography: Mass Spectrum (CI) 608 (MH+).

EXAMPLE 81

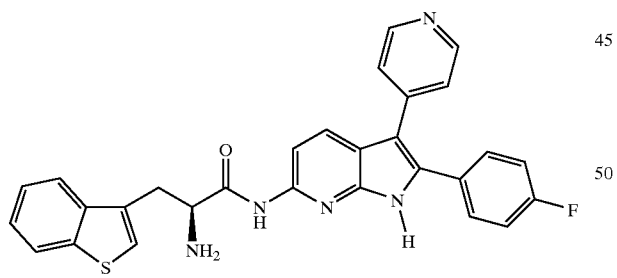

6-(3'-(3-Benzothienyl)-1'-oxo-2'S-aminopropylamino)-3-(4-pyridyl)-2-(4-fluorophenyl)-7-aza-indole (137)

Compound (137) was prepared from compound (136) in the manner of example 6 which afforded 6-(3'-(3-benzothienyl)-1'-oxo-2'S-aminopropylamino)-3-(4-pyridyl)-2-(4-fluorophenyl)-7-aza-indole (137):Mass Spectrum (CI) 508 (MH+).

EXAMPLE 82

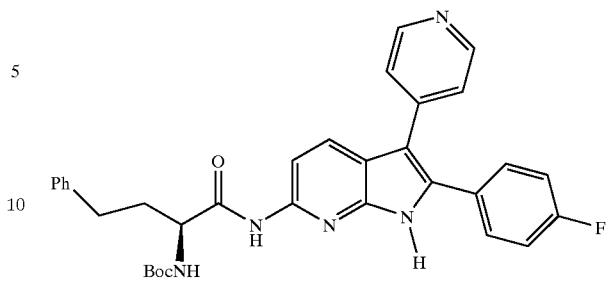

6-(4'-Phenyl-1'-oxo-2'-(L)-t-butoxycarbonylaminobutylamino)-3-(4-pyridyl)-2-(4-fluorophenyl)-7-aza-indole (138)

Compound (138) was prepared in the manner of example 5 with the following substitution: N-a-t-Boc-L-homophenylalanine was used in place of N-t-Boc-g-aminobutyric acid which afforded 6-(4'-phenyl-1'-oxo-2'-(L)-t-butoxycarbonylaminobutylamino)-3-(4-pyridyl)-2-(4-fluorophenyl)-7-aza-indole (138) after preparative plate chromatography: Mass Spectrum (CI) 566 (MH+).

EXAMPLE 83

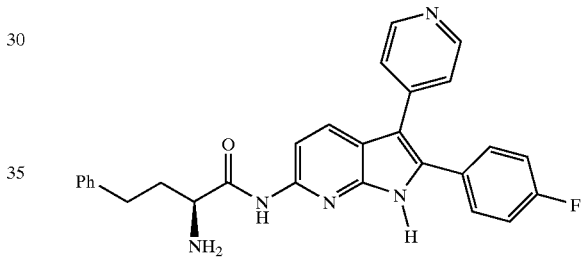

6-(4'-Phenyl-1'-oxo-2'-(L)-aminobutylamino)-3-(4-pyridyl)-2-(4-fluorophenyl)-7-aza-indole (139)

Compound (139) was prepared from compound (138) in the manner of example 6 which afforded 6-(4'-phenyl-1'-oxo-2'-(L)-aminobutylamino)-3-(4-pyridyl)-2-(4-fluorophenyl)-7-aza-indole (139): Mass Spectrum (CI) 466 (MH+).

EXAMPLE 83B

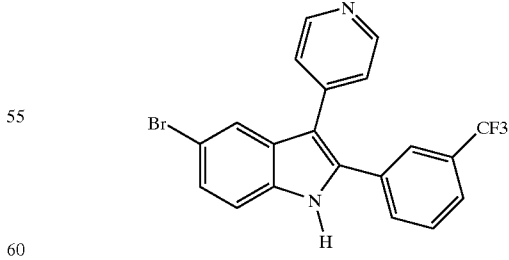

5-Bromo-3-(4-pyridyl)-2-(3-trifluoromethylphenyl)indole 3-(4-Pyridyl)-2-(3-trifluoromethylphenyl)indole was treated with NBS in the same manner as 6-amino-5-bromo-3-(4-pyridyl)-2-(4-fluorophenyl)-7-aza-indole to afford the title compound: Mass Spectrum (CI) 417 (MBr$^{81}$-H).

EXAMPLE 84

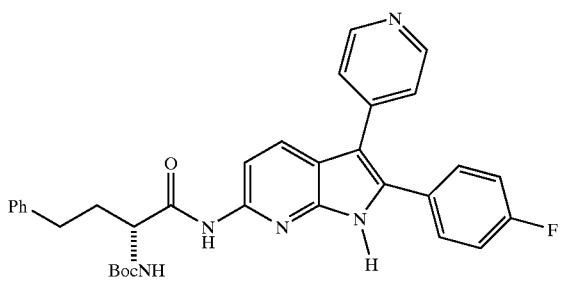

6-(4'-Phenyl-1'-oxo-2'-(D)-t-butoxycarbonylaminobutylamino)-3-(4-pyridyl)-2-(4-fluorophenyl)-7-aza-indole (140)

Compound (140) was prepared in the manner of example 5 with the following substitution: N-a-t-Boc-D-homophenylalanine was used in place of N-t-Boc-g-aminobutyric acid which afforded 6-(4'-phenyl-1'-oxo-2'-(D)-t-butoxycarbonylaminobutylamino)-3-(4-pyridyl)-2-(4-fluorophenyl)-7-aza-indole (140) after preparative plate chromatography: Mass Spectrum (CI) 566 (MH$^+$).

EXAMPLE 85

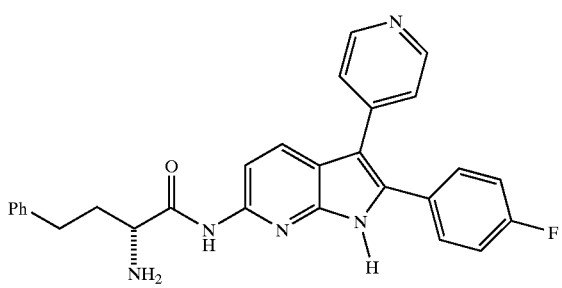

6-(4'-Phenyl-1'-oxo-2'-(D)-aminobutylamino)-3-(4-pyridyl)-2-(4-fluorophenyl)-7-aza-indole (141)

Compound (141) was prepared from compound (140) in the manner of example 6 which afforded 6-(4'-phenyl-1'-oxo-2'-(D)-aminobutylamino)-3-(4-pyridyl)-2-(4-fluorophenyl)-7-aza-indole (141): Mass Spectrum (CI) 466 (MH$^+$).

EXAMPLE 86

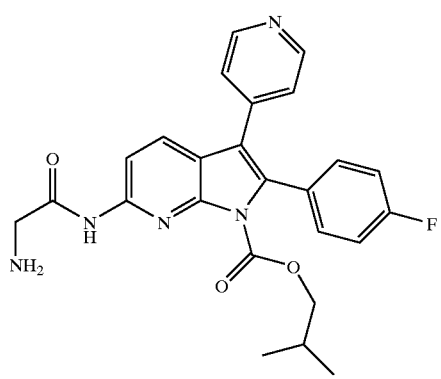

6-(2'-Amino-1'-oxo-ethylamino)-3-(4-pyridyl)-2-(4-fluorophenyl)-1-isobutoxycarbonyl-7-aza-indole (143)

6-(2'-t-butoxycarbonylamino-1'-oxo-ethylamino)-3-(4-pyridyl)-2-(4-fluorophenyl)-7-aza-indole (29) (50 mg, 0.108 mmol), isobutyl chloroformate (42 ml, 0.325 mmol), N-methylmorpholine (119 ml, 1.08 mmol), potassium carbonate (74.9 mg, 0.542 mmol), and DMF (4 mL) were warmed at 80° C. for 16 h. After cooling to 23 C, the reaction was diluted with water (20 mL), extracted with ethyl acetate (2×20 mL), and dried (Na2SO4). After concentration in vacuo, the residue was purified by preparative plate chromatography to afford 6-(2'-t-butoxycarbonylamino-1'-oxo-ethylamino)-3-(4-pyridyl)-2-(4-fluorophenyl)-1-isobutoxycarbonyl-7-aza-indole (142). Compound (104) was converted to 6-(2'-amino-1'-oxo-ethylamino)-3-(4-pyridyl)-2-(4-fluorophenyl)-1-isobutoxycarbonyl-7-aza-indole (143) in the manner of example 6: Mass Spectrum (CI) 462 (MH$^+$).

EXAMPLE 87

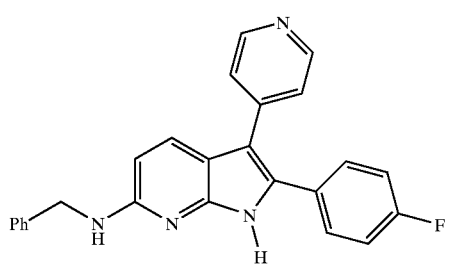

6-(Phenylmethylamino)-3-(4-pyridyl)-2-(4-fluorophenyl)-7-aza-indole (144)

6-Amino-3-(4-pyridyl)-2-(4-fluorophenyl)-7-aza-indole (17) (100 mg, 0.329 mmol), benzaldehyde (100 ml, 0.987 mmol), and 1,2-dichloroethane (20 mL) were allowed to stir for 15 min followed by the addition of sodium triacetoxyborohydride (139 mg, 0.658 mmol) as a solid. After 16 h at 23° C., the reaction was partitioned between ethyl acetate (200 mL) and satd bicarbonate (80 mL). The organic layer was washed with brine (80 mL), and dried (Na2SO4). After concentration in vacuo, a portion of the residue was purified by preparative chromatography to afford 6-(phenylmethylamino)-3-(4-pyridyl)-2-(4-fluoro phenyl)-7-aza-indole (144):Mass Spectrum (CI) 395 (MH$^+$).

EXAMPLE 88

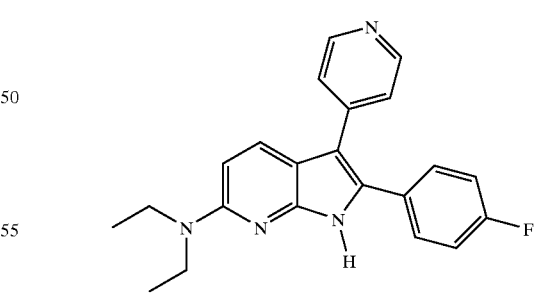

6-(Diethylamino)-3-(4-pyridyl)-2-(4-fluorophenyl)-7-aza-indole (145)

Compound (145) was prepared in the manner of example 87 with the following substitution: acetaldehyde was used in place of benzaldehyde which afforded 6-(diethylamino)-3-(4-pyridyl)-2-(4-fluorophenyl)-7-aza-indole (145) after preparative plate chromatography: Mass Spectrum (CI) 361 (MH$^+$).

EXAMPLE 89

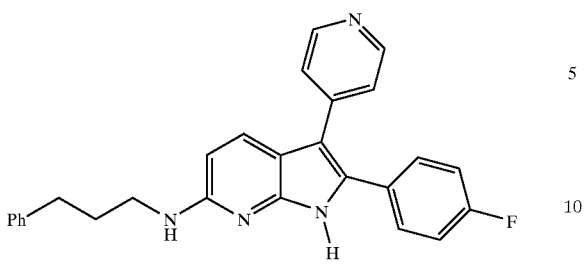

6-(3'-Phenylpropylamino)-3-(4-pyridyl)-2-(4-fluorophenyl)-7-aza-indole (146)

Compound (146) was prepared in the manner of example 87 with the following substitution: phenylhydrocinnamaldehyde was used in place of benzaldehyde which afforded 6-(3'-phenylpropylamino)-3-(4-pyridyl)-2-(4-fluorophenyl)-7-aza-indole (146) after preparative plate chromatography: Mass Spectrum (CI) 423 (MH$^+$).

EXAMPLE 90

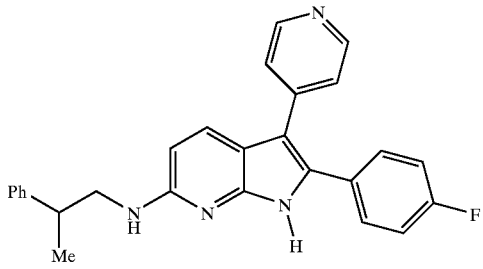

6-(2'(R,S)-Phenylpropylamino)-3-(4-pyridyl)-2-(4-fluorophenyl)-7-aza-indole (147)

Compound (147) was prepared in the manner of example 87 with the following substitution: 2'-phenylpropionaldehyde was used in place of benzaldehyde which afforded 6-(2'(R,S)-phenylpropylamino)-3-(4-pyridyl)-2-(4-fluorophenyl)-7-aza-indole (147) after preparative plate chromatography: Mass Spectrum (CI) 423 (MH$^-$).

EXAMPLE 91

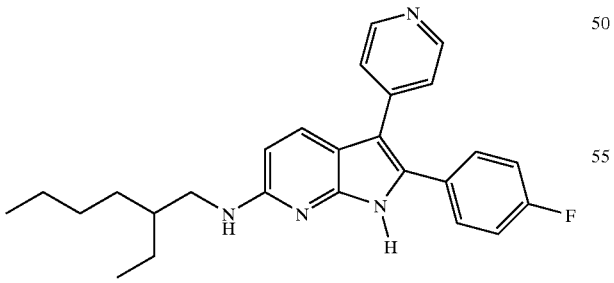

6-(2'(R,S)-Ethylhexylamino)-3-(4-pyridyl)-2-(4-fluorophenyl)-7-aza-indole (148)

Compound (148) was prepared in the manner of example 87 with the following substitution: 2'-ethylhexanaldehyde was used in place of benzaldehyde which afforded 6-(2'(R,S)-ethylhexylamino)-3-(4-pyridyl)-2-(4-fluorophenyl)-7-aza-indole (148) after preparative plate chromatography: Mass Spectrum (CI) 417 (MH$^-$).

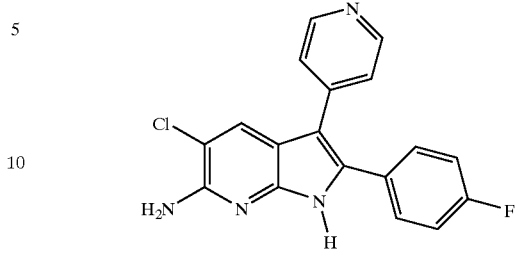

EXAMPLE 92

6-Amino-5-chloro-3-(4-pyridyl)-2-(4-fluorophenyl)-7-aza-indole (149)

Compound (149) was prepared in the manner of example 3 with the following substitution: 3-chloro-2,6-diaminopyridine was used in place of 2,6-diaminopyridine which afforded after 6-Amino-5-chloro-3-(4-pyridyl)-2-(4-fluorophenyl)-7-aza-indole (149) after flash chromatography: Mass Spectrum (CI) 439 (MH$^+$).

EXAMPLE 93

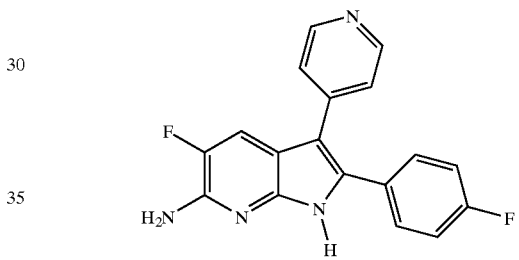

6-Amino-5-fluoro-3-(4-pyridyl)-2-(4-fluorophenyl)-7-aza-indole (28)

6-Amino-3-(4-pyridyl)-2-(4-fluorophenyl)-7-aza-indole (17) (250 mg, 0.822 mmol), N-fluorobenzenesulphonamide (259 mg, 0.822 mmol), and DMF (4 mL) were warmed to 90° C. behind an explosion shield. After 48 h, the reaction was concentrated in vacuo and the residue was purified by flash chromatography (ethyl acetate: hexane 1:1) to afford 6-Amino-5-fluoro-3-(4-pyridyl)-2-(4-fluorophenyl)-7-aza-indole (28): Mass Spectrum (CI) 323 (MH$^+$).

EXAMPLE 94

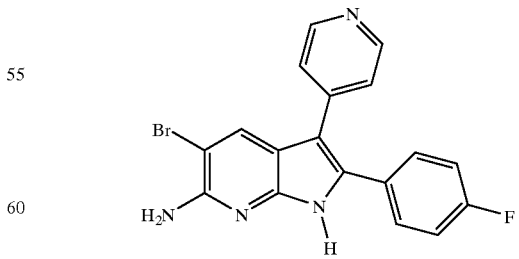

6-Amino-5-bromo-3-(4-pyridyl)-2-(4-fluorophenyl)-7-aza-indole (27)

6-Amino-3-(4-pyridyl)-2-(4-fluorophenyl)-7-aza-indole (17) (250 mg, 0.822 mmol), N-bromosuccinamide (146 mg, 0.822 mmol), and DMF (4 mL) were allowed to stir at 23° C. After 24 h, the reaction was concentrated in vacuo and the residue was purified by flash chromatography (ethyl acetate: hexane 1:1) to afford 6-Amino-5-bromo-3-(4-pyridyl)-2-(4-fluorophenyl)-7-aza-indole (27): Mass Spectrum (CI) 385 (MH$^+$Br$^{81}$).

EXAMPLE 95

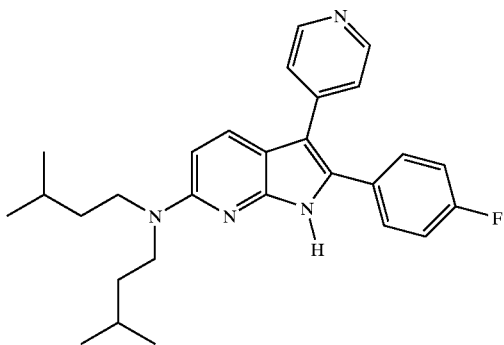

6-(di-Isoamylamino)-3-(4-pyridyl)-2-(4-fluorophenyl)-7-aza-indole (150)

Compound (150) was prepared in the manner of example 87 with the following substitution: 3-methylbutyraldehyde was used in place of benzaldehyde which afforded 6-(di-isoamylamino)-3-(4-pyridyl)-2-(4-fluorophenyl)-7-aza-indole (150) after preparative plate chromatography: Mass Spectrum (CI) 445 (MH$^+$).

EXAMPLE 96

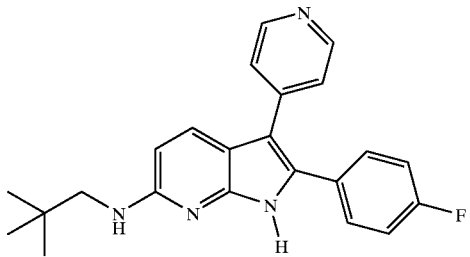

6-(2',2'-Dimethylpropylamino)-3-(4-pyridyl)-2-(4-fluorophenyl)-7-aza-indole (151)

Compound (151) was prepared in the manner of example 87 with the following substitution: pivaldehyde was used in place of benzaldehyde which afforded 6-(2',2'-dlmethylpropylamino)-3-(4-pyridyl)-2-(4-fluorophenyl)-7-aza-indole (151) after preparative plate chromatography: Mass Spectrum (CI) 375 (MH$^-$).

EXAMPLE 97

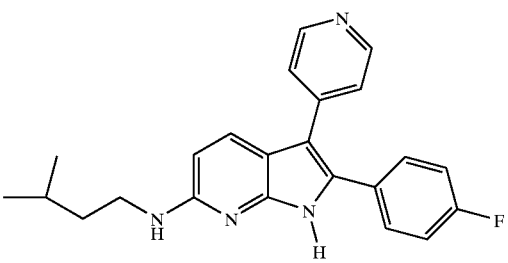

6-(Isoamylamino)-3-(4-pyridyl)-2-(4-fluorophenyl)-7-aza-indole (152)

Compound (152) was prepared in the manner of example 87 with the following substitution: 3-methylbutyraldehyde was used in place of benzaldehyde which afforded 6-(isoamylamino)-3-(4-pyridyl)-2-(4-fluorophenyl)-7-aza-indole (152) after preparative plate chromatography: Mass Spectrum (CI) 375 (MH$^+$).

EXAMPLE 98

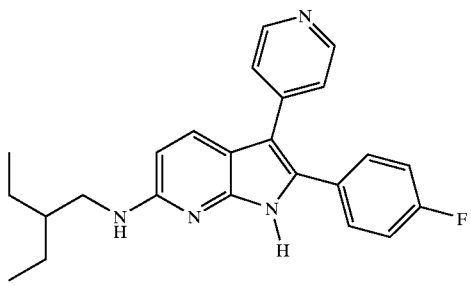

6-(2'-(2'-Ethylbutylamino)-3-(4-pyridyl)-2-(4-fluorophenyl)-7-aza-indole (153)

Compound (153) was prepared in the manner of example 87 with the following substitution: 2-ethylbutyraldehyde was used in place of benzaldehyde which afforded 6-(2'-ethylbutylamino)-3-(4-pyridyl)-2-(4-fluorophenyl)-7-aza-indole (153) after preparative plate chromatography: Mass Spectrum (CI) 389 (MH$^-$).

EXAMPLE 99

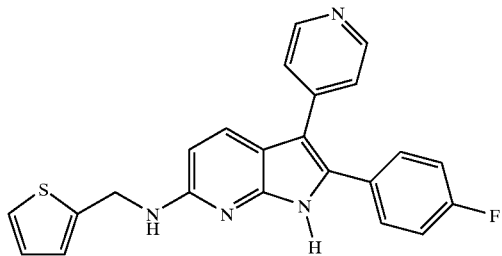

6-(2'-Thienylmethylamino)-3-(4-pyridyl)-2-(4-fluorophenyl)-7-aza-indole (154)

Compound (154) was prepared in the manner of example 87 with the following substitution: 2-thiophene carboxaldehyde was used in place of benzaldehyde which afforded 6-(2'-thienylmethylamino)-3-(4-pyridyl)-2-(4-fluorophenyl)-7-aza-indole (154) after preparative plate chromatography: Mass Spectrum (CI) 401 (MH$^+$).

EXAMPLE 100

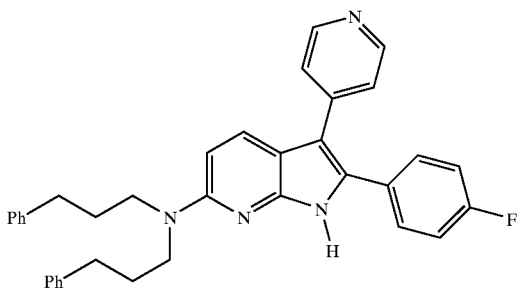

6-(3',3'di-Phenylpropylamino)-3-(4-pyridyl)-2-(4-fluorophenyl)-7-aza-indole (155)

Compound (155) was prepared in the manner of example 87 with the following substitution: phenylhydrocinnamaldehyde was used in place of benzaldehyde which afforded 6-(3',3di-phenylpropylamino)-3-(4-pyridyl)-2-(4-fluorophenyl)-7-aza-indole (155) after preparative plate chromatography: Mass Spectrum (CI) 541 (MH$^-$).

EXAMPLE 101

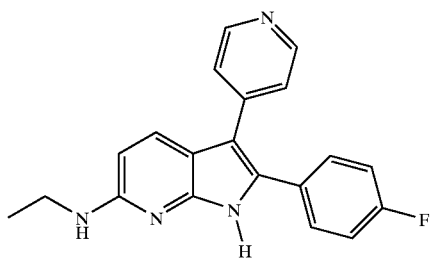

6-(Ethylamino)-3-(4-pyridyl)-2-(4-fluorophenyl)-7-aza-indole (156)

Compound (156) was prepared in the manner of example 87 with the following substitution: acetaldehyde was used in place of benzaldehyde which afforded 6-(diethylamino)-3-(4-pyridyl)-2-(4-fluorophenyl)-7-aza-indole (156) after preparative plate chromatography: Mass Spectrum (CI) 361 (MH$^+$).

EXAMPLE 102

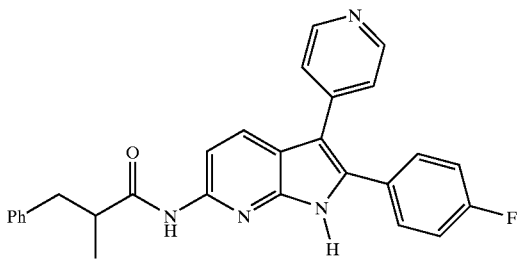

6-(3'-Phenyl-1'-oxo-2'-(R,S)-methylpropylamino)-3-(4-pyridyl)-2-(4-fluorophenyl)-7-aza-indole (157)

Compound (157) was prepared in the manner of example 5 with the following substitution: 3-phenyl-2-methylpropionic acid was used in place of N-t-Boc-g-aminobutyric acid which afforded 6-(3'-phenyl-1'-oxo-2'-(R,S)-methylpropylamino)-3-(4-pyridyl)-2-(4-fluorophenyl)-7-aza-indole (157) after preparative plate chromatography: Mass Spectrum (CI) 451 (MH$^+$).

EXAMPLE 103

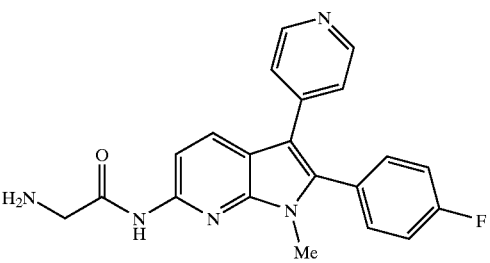

6-(2'-Amino-1'-oxo-ethylamino)-3-(4-pyridyl)-2-(4-fluorophenyl)-1-methyl-7-aza-indole (158)

To a solution of 6-(2'-t-butoxycarbonylamino-1'-oxo-ethylamino)-3-(4-pyridyl)-2-(4-fluorophenyl)-7-aza-indole (29) (50.0 mg, 0.108 mmol), triphenylphosphine (85 mg, 0.325 mmol), methanol (13 ml, 0.791 mmol) and methylene chloride (5 mL) was added diethyl azodicarboxylate (51 ml, 0.325 mmol) at 0° C. The reaction was allowed to warm to 23° C. After 2.5 h, an additional 2 equivalents of methanol, triphenylphosphine, and diethyl azodicarboxylate were added. After 16 h, the reaction was concentrated in vacuo and the residue was purified by preparative plate chromatography to afford 6-(2'-t-butoxycarbonylamino-1'-oxo-ethylamino)-3-(4-pyridyl)-2-(4-fluorophenyl)-1-methyl-7-aza-indole (30) which was converted to 6-(2'-amino-1'-oxo-ethylamino)-3-(4-pyridyl)-2-(4-fluorophenyl)-1-methyl-7-aza-indole (158) as described in example 6: Mass Spectrum (CI) 376 (MH+).

EXAMPLE 104

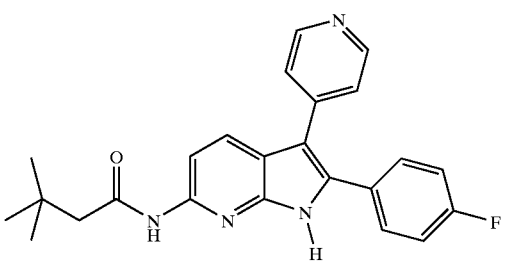

6-(3',3'-Dimethyl-1'-oxo-butylamino)-3-(4-pyridyl)-2-(4-fluorophenyl)-7-aza-indole (159)

Compound (159) was prepared in the manner of example 5 with the following substitution: 3,3-dimethylbutyric acid was used in place of N-t-Boc-g-aminobutyric acid which afforded 6-(3',3'-dimethyl-1'-oxo-butylamino)-3-(4-pyridyl)-2-(4-fluorophenyl)-7-aza-indole (159) after preparative plate chromatography: Mass Spectrum (CI) 403 (MH$^+$).

EXAMPLE 105

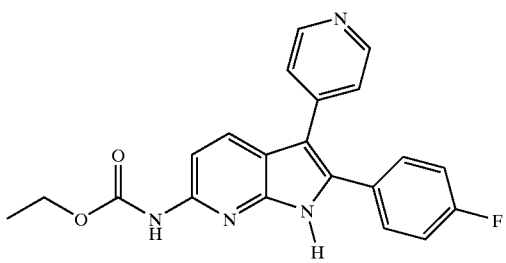

6-(Ethoxycarbonylamino)-3-(4-pyridyl)-2-(4-fluorophenyl)-7-aza-indole (160)

Compound (160) was obtained as a side product from example 104 wherein a small amount of unreacted ethyl chloroformate resulted in acylation of the 6-amino function to afford 6-(ethoxycarbonylamino)-3-(4-pyridyl)-2-(4-fluorophenyl)-7-aza-indole (160) after preparative plate chromatography: Mass Spectrum (CI) 377 (MH⁻).

EXAMPLE 106

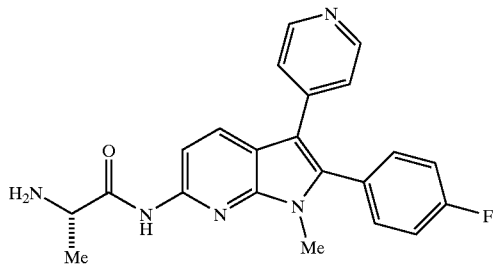

6-(2'S-Amino-1-oxo-poropylamino)-3-(4-pyridyl)-2-(4-fluorophenyl)-1-methyl-7-aza-indole (161)

Compound (161) was prepared in the manner of example 87 with the following substitution: 6-(2'S-t-butoxycarbonyl amino-1'-oxo-propylamino)-3-(4-pyridyl)-2-(4-fluoro phenyl)-7-aza-indole was used in place of 6-(2'-t-butoxycarbonylamino-1'-oxo-ethylamino)-3-(4-pyridyl)-2-(4-fluorophenyl)-7-aza-indole which afforded 6-(2'S-amino-1'-oxo-propylamino)-3-(4-pyridyl)-2-(4-fluoro phenyl)-1-methyl-7-aza-indole (161) after preparative plate chromatography: Mass Spectrum (CI) 390 (MH+).

EXAMPLE 107

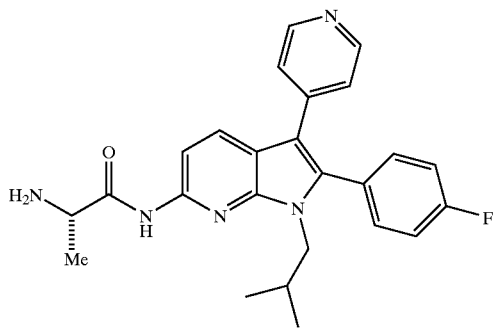

6-(2'S-Amino-1'-oxo-propylamino)-3-(4-pyridyl)-2-(4-fluorophenyl)-1-isobutyl-7-aza-indole (162)

Compound (162) was prepared in the manner of example 87 with the following substitutions: 6-(2'S-t-butoxycarbonyl amino-1'-oxo-propylamino)-3-(4-pyridyl)-2-(4-fluoro phenyl)-7-aza-indole was used in place of 6-(2'-t-butoxycarbonylamino-1'-oxo-ethylamino)-3-(4-pyridyl)-2-(4-fluorophenyl)-7-aza-indole and isobutanol was used in place of methanol which afforded 6-(2'S-amino-1'-oxo-propylamino)-3-(4-pyridyl)-2-(4-fluorophenyl)-1-isobutyl-7-aza-indole (162) after preparative plate chromatography: Mass Spectrum (CI) 432 (MH⁺).

EXAMPLE 108

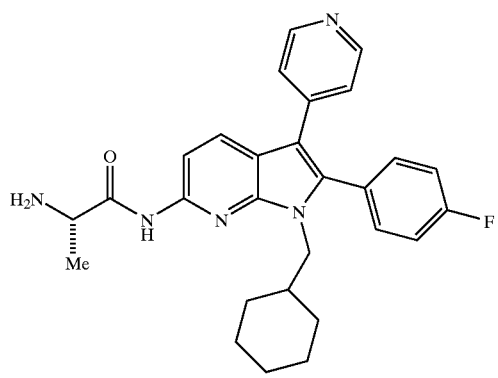

6-(2'S-Amino-1'-oxo-propylamino)-3-(4-pyridyl)-2-(4-fluorophenyl)-1-cyclohexylmethyl-7-aza-indole (163)

Compound (163) was prepared in the manner of example 87 with the following substitutions: 6-(2'S-t-butoxycarbonylamino-1'-ox6-propylamino)-3-(4-pyridyl)-2-(4-fluorophenyl)-7-aza-indole was used in place of 6-(2'-t-butoxycarbonylamino-1'-oxo-ethylamino)-3-(4-pyridyl)-2-(4-fluorophenyl)-7-aza-indole and cyclohexymethanol was used in place of methanol which afforded 6-(2'S-amino-1'-oxo-propylamino)-3-(4-pyridyl)-2-(4-fluorophenyl)-1-isobutyl-7-aza-indole (163) after preparative plate chromatography: Mass Spectrum (CI) 472 (MH⁺).

EXAMPLE 109

Using the procedures of the above general description and the above examples, the compounds of Tables 1–7 can be prepared.

TABLE 1

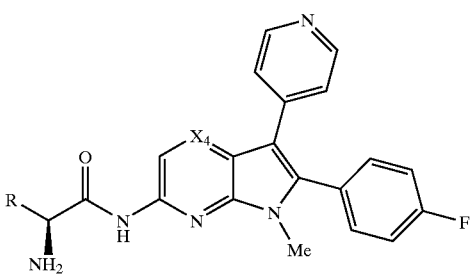

| R | $X_4$ | R | $X_4$ |
|---|---|---|---|
| butyl | CH | methyl | C—CH3 |
| ethyl | N | ethyl | C—CH(OH)CH3 |
| propyl | CH | propyl | C—CH2OH |
| isopropyl | N | isopropyl | C—N(CH3)2 |
| hydroxymethyl | N | hydroxymethyl | C—OCH3 |
| hydroxyethyl | CH | hydroxyethyl | C—CH3 |
| benzyl | N | benzyl | C—OCF3 |
| 4-methoxybenzyl | N | 4-methoxybenzyl | C—OH |
| 4-iodobenzyl | CH | 4-iodobenzyl | C—CH3 |
| 4-pyridylmethyl | N | 4-pyridylmethyl | C—CH3 |
| 3-pyridylmethyl | CH | 3-pyridylmethyl | C—OH |
| 2-pyridylmethyl | N | 2-pyridylmethyl | C—OCH3 |
| methylthioethyl | N | methylthioethyl | C—CF3 |
| methylsulfonylethyl | CH | methylsulfonylethyl | C—F |
| methylsulfinylethyl | N | methylsulfinylethyl | C—CH(OH)CH3 |
| imidazolylmethyl | C—CH3 | imidazolylmethyl | C—OCH3 |

TABLE 2

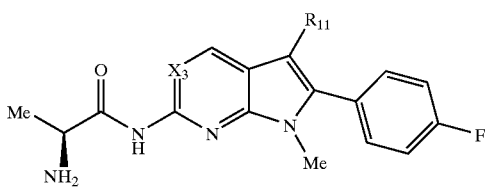

| $R_{11}$ | $X_3$ |
|---|---|
| 4-pyridyl | C—F |
| 4-pyridyl | N |
| 4-pyridyl | C—Br |
| 4-quinolinyl | N |
| 4-(2-aminopyridyl) | C—F |
| 4-(2-aminopyridyl) | C—CF3 |
| 4-(2-aminopyridyl) | N |
| 4-quinolinyl | C—F |
| 4-quinolinyl | C—CF3 |
| 4-pyridyl | C—Ph |
| 4-quinolinyl | C—Ph |
| 4-(2-aminopyridyl) | C—Ph |
| 4-quinolinyl | C—Cl |
| 4-(2-aminopyridyl) | C—Cl |
| 4-(2-aminoimidazoyl) | C—F |
| 4-(2-aminoimidazoyl) | C—Br |
| 4-pyrimidinyl | C—CF3 |
| 4-pyrimidinyl | N |
| 4-pyrimidinyl | C—F |
| 4-pyrimidinyl | C—Cl |
| 4-pyrimidinyl | C—Ph |
| 4-(2-aminoimidazoyl) | C—CH3 |
| 4-(2-aminoimidazoyl) | C—CH(OH)CH3 |
| 4-quinolinyl | C—CH2OH |
| 4-pyridyl | C—N(CH3)2 |
| 4-pyridyl | C—OCH3 |
| 4-quinolinyl | C—CH3 |
| 4-pyridyl | C—OCF3 |
| 4-pyridyl | C—OH |
| 4-(2-aminopyridyl) | C—CH3 |

TABLE 2-continued

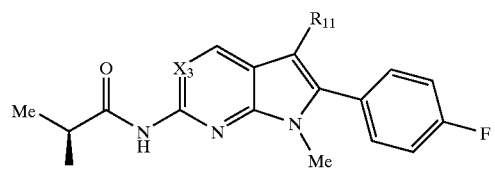

| $R_{11}$ | $X_3$ |
|---|---|
| 4-pyridyl | C—CH3 |
| 4-quinolinyl | C—OH |
| 4-quinolinyl | C—OCH3 |
| 4-pyridyl | C—CF3 |
| 4-(2-acetamidopyridyl) | C—F |
| 4-pyridyl | C—CH(OH)CH3 |
| 4-(2-aminopyridyl) | C—OCH3 |
| 4-pyrimidinyl | C—CH3 |
| 4-pyrimidinyl | C—OH |
| 4-pyrimidinyl | C—OCH3 |
| 4-pyrimidinyl | C—CH(OH)CH3 |
| 4-pyrimidinyl | C—Br |

TABLE 3

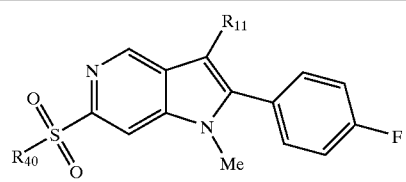

| $R_{11}$ | $R_{40}$ |
|---|---|
| 4-pyridyl | —NH2 |
| 4-pyridyl | —NHPh |
| 4-pyridyl | —NHCH3 |
| 4-quinolinyl | —NH(4-MeOPh) |
| 4-(2-aminopyridyl) | —NH2 |
| 4-(2-aminopyridyl) | —NHPh |
| 4-(2-aminopyridyl) | —NHCH3 |
| 4-quinolinyl | —NH2 |
| 4-quinolinyl | —NHPh |
| 4-pyridyl | —NH(4-MeOPh) |
| 4-quinolinyl | —CH2N(CH3)2 |
| 4-(2-aminopyridyl) | —CH2N(CH3)2 |
| 4-quinolinyl | —CH2CH2N(CH3)2 |
| 4-(2-aminopyridyl) | —CH2NH2 |
| 4-(2-aminoimidazoyl) | —CH2CH2N(CH3)2 |
| 4-(2-aminoimidazoyl) | —CH2N(CH3)2 |
| 4-pyrimidinyl | —NH2 |
| 4-pyrimidinyl | —NHPh |
| 4-pyrimidinyl | —NHCH3 |
| 4-pyrimidinyl | —NH(4-MeOPh) |
| 4-pyrimidinyl | —Ph |
| 4-(2-aminoimidazoyl) | —CH3 |
| 4-(2-aminoimidazoyl) | —Ph |
| 4-quinolinyl | —Ph |
| 4-pyridyl | —Ph |
| 4-pyridyl | 2-thienyl |
| 4-quinolinyl | —CH2NH2 |
| 4-pyridyl | n-Bu |
| 4-pyridyl | —CH2N(CH3)2 |
| 4-(2-aminopyridyl) | —CH3 |
| 4-pyridyl | —CH3 |
| 4-quinolinyl | —CH3 |
| 4-quinolinyl | n-propyl |
| 4-pyridyl | —CH2CH2N(CH3)2 |
| 4-(2-acetamidopyridyl) | —CH2CH2N(CH3)2 |
| 4-pyridyl | —CH2NH2 |
| 4-(2-aminopyridyl) | —CH2NH2 |
| 4-pyrimidinyl | 2-thienyl |
| 4-pyrimidinyl | —CH2NH2 |

TABLE 3-continued

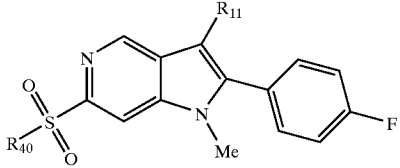

| R11 | R40 |
|---|---|
| 4-pyrimidinyl | n-Bu |
| 4-pyrimidinyl | —CH2N(CH3)2 |
| 4-pyrimidinyl | —CH3 |

TABLE 4

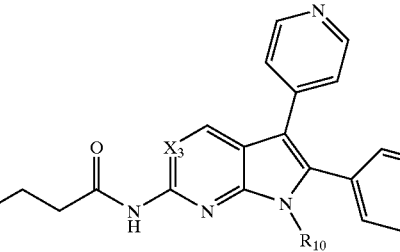

| R10 | X3 | R10 | X3 |
|---|---|---|---|
| methyl | CH | methyl | C—CH3 |
| ethyl | N | ethyl | C—CH(OH)CH3 |
| propyl | CH | propyl | C—CH2OH |
| isopropyl | N | isopropyl | C—N(CH3)2 |
| —C(O)Ph | N | benzyl | C—OCH3 |
| —C(O)NH2 | CH | —C(O)NH2 | C—CH3 |
| benzyl | N | 4-methoxybenzyl | C—OCF3 |
| 4-methoxybenzyl | N | 4-iodobenzyl | C—OH |
| —C(O)NHPh | CH | 4-pyridylmethyl | C—CH3 |
| —C(O)NHEt | N | 3-pyridylmethyl | C—CH3 |
| —C(O)Ph | CH | —C(O)Ph | C—OH |
| —C(O)NH2 | N | —C(O)NHEt | C—OCH3 |
| methyl | N | ethyl | C—CF3 |
| ethyl | CH | methyl | C—F |
| isobutyl | N | —C(O)NH2 | C—CH(OH)CH3 |
| methyl | C—CH3 | methyl | C—OCH3 |

TABLE 5

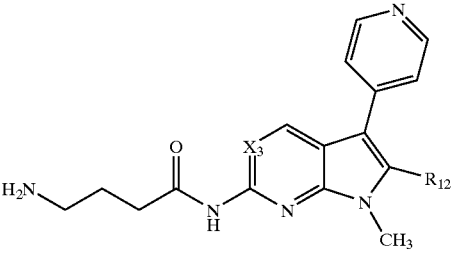

| R12 | X3 |
|---|---|
| phenyl | CH |
| phenyl | N |
| 3-chlorophenyl | CH |
| 3-chlorophenyl | N |
| 4-fluorophenyl | N |
| 4-fluorophenyl | CH |
| 1-naphthyl | N |
| 2-naphthyl | N |

TABLE 5-continued

| R12 | X3 |
|---|---|
| 3-methylthiophenyl | CH |
| 3-methylthiophenyl | N |
| 1-naphthyl | CH |
| 3,4-dichlorophenyl | N |
| 3-trifluoromethylphenyl | N |
| 3,4-dichlorophenyl | CH |
| 4-methoxyphenyl | N |
| 4-methoxyphenyl | C—CH3 |
| 3-chlorophenyl | C—CH3 |
| 3-chlorophenyl | C—CH(OH)CH3 |
| 4-fluorophenyl | C—CH2OH |
| 4-fluorophenyl | C—N(CH3)2 |
| 3-methylthiophenyl | C—OCH3 |
| 3-methylthiophenyl | C—CH3 |
| 3-methylsulfinylphenyl | C—OCF3 |
| 4-cyanophenyl | C—OH |
| 4-carboxamidophenyl | C—CH3 |
| 4-fluorophenyl | C—CH3 |
| 3,4-dichlorophenyl | C—OH |
| 3-methylthiophenyl | C—OCH3 |
| 3,4-dichlorophenyl | C—CF3 |
| 4-fluorophenyl | C—F |
| 4-methoxyphenyl | C—CH(OH)CH3 |
| 4-methoxyphenyl | C—OCH3 |

TABLE 6

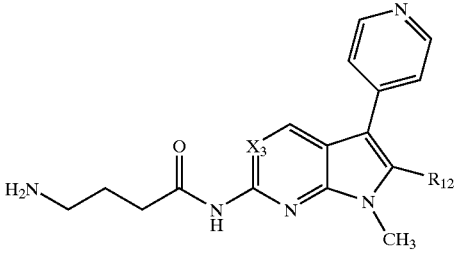

| R41 | X3 |
|---|---|
| methyl | CF |
| —CH2NH2 | N |
| 2-(5-chlorothienyl) | C—Br |
| —CH2NMe2 | N |
| phenyl | C—F |
| methyl | C—CF3 |
| 1-naphthyl | N |
| 2-(5-chlorothienyl) | C—F |
| —CH2CH2NH2 | C—CF3 |
| phenyl | C—Ph |
| methyl | C—Ph |
| —CH2NH2 | C—Ph |
| phenyl | C—Cl |
| methyl | C—Cl |
| methyl | C—F |
| —CH2NH2 | C—Br |
| n-butyl | C—CF3 |
| 4-methoxyphenyl | N |
| 4-cyanophenyl | C—F |

TABLE 6-continued

| R41 | X3 |
|---|---|
| 4-n-butoxyphenyl | C—Cl |
| methyl | C—Ph |
| methyl | C—CH3 |
| —CH2NH2 | C—CH(OH)CH3 |
| 2-(5-chlorothienyl) | C—CH2OH |
| —CH2NMe2 | C—N(CH3)2 |
| phenyl | C—OCH3 |
| methyl | C—CH3 |
| 1-naphthyl | C—OCF3 |
| 2-(5-chlorothienyl) | C—OH |
| —CH2CH2NH2 | C—CH3 |
| 4-carboxymethylphenyl | C—CH3 |
| 4-n-butoxyphenyl | C—OH |
| 1-naphthyl | C—OCH3 |
| methyl | C—CF3 |
| —CH2NH2 | C—F |
| methyl | C—CH(OH)CH3 |
| —CH2CH2NH2 | C—OCH3 |
| 3-(1-piperidinyl)propyl | C—CH3 |
| 3-(1-piperizinyl)propyl | C—OH |
| 2-(5-chlorothienyl) | C—OCH3 |
| —CH2NH2 | C—CH(OH)CH3 |
| n-butyl | C—Br |

TABLE 7

| X2 | X3 |
|---|---|
| —C—C(O)Ph | C—F |
| —C—C(O)NHMe | N |
| —C—C(O)NHMe | C—Br |
| —C—S(O2)—Et | N |
| —C—C(O)—Bu | C—F |
| —CH | C—CF3 |
| —C—S(O2)—NHEt | N |
| —C—NH—S(O2)—NHCH3 | C—F |
| —C—C(O2)Me | C—CF3 |
| —CH | C—Ph |
| —C—S(O2)—Et | C—Ph |
| —C—C(O)Ph | C—Ph |
| —CH | C—Cl |
| —C—NHEt | C—Cl |
| —C—NHPr | C—F |
| —CH | C—Br |
| —C—NHMe | C—CF3 |
| —C—C(O)NHPh | N |
| —C—N(Me)—C(O)—Me | C—F |
| —C—N—S(O2)Me | C—Cl |

TABLE 7-continued

| X2 | X3 |
|---|---|
| —C—NHEt | C—Ph |
| N | C—CH3 |
| C—F | C—CH(OH)CH3 |
| C—CF3 | C—CH2OH |
| N | C—N(CH3)2 |
| C—Br | C—OCH3 |
| N | C—CH3 |
| —CH | C—OCF3 |
| —CH | C—OH |
| C—C(O2)Me | C—CH3 |
| —CH | C—CH3 |
| —CH | C—OH |
| C—NHEt | C—OCH3 |
| —CH | C—CF3 |
| —CH | C—F |
| —CH | C—CH(OH)CH3 |
| —CH | C—OCH3 |
| —CH | C—CH3 |
| C—C(O2)Me | C—OH |
| C—F | C—OCH3 |
| C—CF3 | C—CH(OH)CH3 |
| C—S(O2)—Et | C—Br |

TABLE 8

| X2 | X3 |
|---|---|
| —C—NH—C(O)Me | C—F |
| —C—C(O)NHMe | N |
| —C—C(O)NHMe | C—Br |
| —C—NH—S(O2)Me | N |
| —C—C(O)—Bu | C—F |
| —CH | C—CF3 |
| —C—NH(CO)CH2NH2 | N |
| —C—NH—S(O2)—NHCH3 | C—F |
| —C—C(O2)Me | C—CF3 |
| —CH | C—Ph |
| —C—S(O2)—Et | C—Ph |
| —C—C(O)Ph | C—Ph |
| —CH | C—Cl |
| —C—NHEt | C—Cl |
| —C—NHPr | C—F |
| —CH | C—Br |
| —C—NHMe | C—CF3 |
| —C—C(O)NHPh | N |
| —C—NH—S(O2)Me | C—F |
| —C—N—S(O2)Me | C—Cl |
| —C—NHEt | C—Ph |

TABLE 8-continued

[Structure: 1-Me-2-(4-methylsulfonylphenyl)-3-(pyridin-4-yl)pyrrolo-pyridine with X2, X3 positions]

| X₂ | X₃ |
|---|---|
| N | C—CH3 |
| C—F | C—CH(OH)CH3 |
| C—CF3 | C—CH2OH |
| N | C—N(CH3)2 |
| C—Br | C—OCH3 |
| N | C—CH3 |
| —CH | C—OCF3 |
| —CH | C—OH |
| C—C(O2)Me | C—CH3 |
| —CH | C—CH3 |
| —CH | C—OH |
| C—NHEt | C—OCH3 |
| —CH | C—CF3 |
| —CH | C—F |
| —CH | C—CH(OH)CH3 |
| —CH | C—OCH3 |
| —CH | C—CH3 |
| C—C(O2)Me | C—OH |
| C—F | C—OCH3 |
| C—CF3 | C—CH(OH)CH3 |
| C—S(O2)—Et | C—Br |

TABLE 9

[Structure: 1-Me-2-(4-sulfamoylphenyl)-3-(pyridin-4-yl)pyrrolo-pyridine with X2, X3 positions]

| X₂ | X₃ |
|---|---|
| —C—NH—C(O)Me | C—F |
| —C—C(O)NHMe | N |
| —C—C(O)NHMe | C—Br |
| —C—NH—S(O2)Me | N |
| —C—C(O)—Bu | C—F |
| —CH | C—CF3 |
| —C—NH(CO)CH2NH2 | N |
| —C—NH—C(O)CH(Me)NH2 | C—F |
| —C—C(O2)Me | C—CF3 |
| —CH | C—Ph |
| —C—S(O2)—Et | C—Ph |
| —C—C(O)Ph | C—Ph |
| —CH | C—Cl |
| —C—NHEt | C—Cl |
| —C—NHPr | C—F |
| —CH | C—Br |
| —C—NHMe | C—CF3 |
| —C—C(O)NHPh | N |
| —C—NH—S(O2)Me | C—F |
| —C—N—S(O2)Me | C—Cl |
| —C—NHEt | C—Ph |

TABLE 9-continued

[Structure: 1-Me-2-(4-sulfamoylphenyl)-3-(pyridin-4-yl)pyrrolo-pyridine with X2, X3 positions]

| X₂ | X₃ |
|---|---|
| N | C—CH3 |
| C—F | C—CH(OH)CH3 |
| C—CF3 | C—CH2OH |
| N | C—N(CH3)2 |
| C—Br | C—OCH3 |
| N | C—CH3 |
| —CH | C—OCF3 |
| —CH | C—OH |
| C—C(O2)Me | C—CH3 |
| —CH | C—C(O)H |
| —CH | C—OH |
| C—NHEt | C—OCH3 |
| —CH | C—CF3 |
| —CH | C—F |
| —CH | C—CH(OH)CH3 |
| —CH | C—OCH3 |
| —CH | C—CH3 |
| C—C(O2)Me | C—OH |
| C—F | C—OCH3 |
| C—CF3 | C—CH(OH)CH3 |
| C—S(O2)—Et | C—Br |

TABLE 10

[Structure: 1-Me-2-(4-methanesulfonamidophenyl)-3-(pyridin-4-yl)pyrrolo-pyridine with X2, X3 positions]

| X₂ | X₃ |
|---|---|
| —C—NH—C(O)Me | C—F |
| —C—C(O)NHMe | N |
| —C—C(O)NHMe | C—Br |
| —C—NH—S(O2)Me | N |
| —C—C(O)—Bu | C—F |
| —CH | C—CF3 |
| —C—NH(CO)CH2NH2 | N |
| —C—NH—C(O)CH(Me)NH2 | C—F |
| —C—C(O2)Me | C—CF3 |
| —CH | C—Ph |
| —C—S(O2)—Et | C—Ph |
| —C—C(O)Ph | C—Ph |
| —CH | C—Cl |
| —C—NHEt | C—Cl |
| —C—NHPr | C—F |
| —CH | C—Br |
| —C—NHMe | C—CF3 |
| —C—C(O)NHPh | N |
| —C—NH—S(O2)Me | C—F |
| —C—N—S(O2)Me | C—Cl |
| —C—NHEt | C—Ph |

TABLE 10-continued

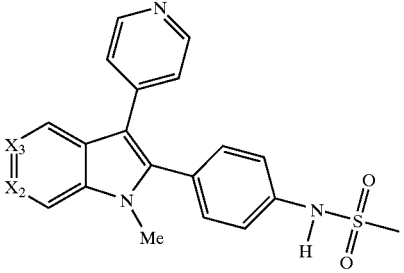

| X₂ | X₃ |
|---|---|
| N | C—CH3 |
| C—F | C—CH(OH)CH3 |
| C—CF3 | C—CH2OH |
| N | C—N(CH3)2 |
| C—Br | C—OCH3 |
| N | C—CH3 |
| —CH | C—OCF3 |
| —CH | C—OH |
| C—C(O2)Me | C—CH3 |
| —CH | C—C(O)H |
| —CH | C—OH |
| C—NHEt | C—OCH3 |
| —CH | C—CF3 |
| —CH | C—F |
| —CH | C—CH(OH)CH3 |
| —CH | C—OCH3 |
| —CH | C—CH3 |
| C—C(O2)Me | C—OH |
| C—F | C—OCH3 |
| C—CF3 | C—CH(OH)CH3 |
| C—S(O2)—Et | C—Br |

EXAMPLE 110

The following assays were used to characterize the ability of compounds of the invention to inhibit the production of TNF-α and IL-1-β. The second assay measured the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a Cyclooxygenase enzyme (COX-1 and COX-2) inhibition activity in vitro assay, can be used to characterize the ability of compounds of the invention to inhibit COX-1 and/or COX-2.

Lipopolysaccharide-activated Monocyte TNF Production Assay

Isolation of Monocytes

Test compounds were evaluated in vitro for the ability to inhibit the production of tumor necrosis factor (TNF) by monocytes activated with bacterial lipopolysaccharide (LPS). Fresh residual source leukocytes (a byproduct of plateletpheresis) were obtained from the local blood bank and peripheral blood mononuclear cells (PBMCS) were isolated by density gradient centrifugation on Ficol-Paque Plus (Pharmacia). PBMCs were suspended at 2×10⁶/ml in DMEM supplemented to contain 2% FCS (10 mM), 0.3 mg/ml glutamate, 100 U/ml penicillin G and 100 mg/ml streptomycin sulfate (complete media). Cells were plated into Falcon flatbottom 96 well culture plates (200 μl/well) and cultured overnight at 37° C. and 6% CO₂. Nonadherent cells were removed by washing with 200 μl/well of fresh medium. Wells containing adherent cells (~70% monocytes) were replenished with 100 μl of fresh medium.

Preparation of Test Compound Stock Solutions

Test compounds were dissolved in DMZ. Compound stock solutions were prepared to an initial concentration of 10–50 μM. Stocks were diluted initially to 20–200 μM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 μl complete medium. Monocytes were cultured with test compounds for 60 min at which time 25 μl of complete medium containing 30 ng/ml lipopolysaccharide from E. coli K532 were added to each well. Cells were cultured an additional 4 hrs. Culture supernatants were then removed and TNF present in the supernatants was quantified using an ELISA.

TNF ELISA

Flat bottom 96 well Corning High Binding ELISA plates were coated overnight (4° C.) with 150 μL/well of 3 μg/ml murine anti-human TNFa MAb (R&D Systems #MAB210). Wells were then blocked 1 h at room temperature with 200 μL/well of CaCl₂-free ELISA buffer supplemented to contain 20 mg/ml BSA (standard ELISA buffer: 20 mM, 150 mM NaCl, 2 mM CaCl₂, 0.15 mM thimerosal, pH 7.4). Plates were washed and replenished with 100 μl of test supernatants (diluted 1:3) or standards. Standards consisted of eleven 1.5-fold serial dilutions from a stock of 1 ng/ml recombinant human TNF (R&D Systems). Plates were incubated at room temperature for 1 h on orbital shaker (300 rpm), washed and replenished with 100 μl/well of 0.5 μg/ml goat anti-human TNFa (R&D systems #AB-210-NA) blotinylated at a 4:1 ratio. Plates were incubate for 40 min, washed and replenished with 100 μl/well of alkaline phosphatase-conjugated streptavidin (Jackson ImmunoResearch #016-050-084) at 0.02 μg/ml. Plates were incubated 30 min, washed and replenished with 200 μl/well of 1 mg/ml of p-nitrophenyl phosphate. After 30 min, plates were read at 405 nm on a Vmax plate reader.

Data Analysis

Standard curve data were fit to a second order polynomial and unknown TNF-α concentrations determined from their OD by solving this equation for concentration. TNF concentrations were then plotted Vs test compound concentration using a second order polynomial. This equation was then used to calculate the concentration of test compounds causing a 50% reduction in TNF production.

The following compounds had an ICSO of less than 20 μM: 3-(4-pyridyl)-2-(4-fluorophenyl)indole (3); 6-amino-3-(4-fluorophenyl)-2-(4-pyridyl)-7-aza-indole (18); 6-(4'-t-butoxycarbonylamino-1'-oxo-butylamino)-3-(4-pyridyl)-2-(4-fluorophenyl)-7-aza-indole (21); 6-(4'-amino-1'-oxo-butylamino)-3-(4-pyridyl)-2-(4-fluorophenyl)-7-aza-indole (22); 6-(5'-ureido-1'-oxo-2'-t-butoxycarbonylaminopentylamino)-3-(4-pyridyl)-2-(4-fluorophenyl)-7-aza-indole (64); 6-(5'-ureido-1'-oxo-2'-aminopentylamino)-3-(4-pyridyl)-2-(4-fluorophenyl)-7-aza-indole (65); 6-(6'-t-butoxycarbonylamino-1'-oxo-2'-t-butoxycarbonylaminohexylamino)-3-(4-pyridyl)-2-(4-fluorophenyl)-7-aza-indole (66); 6-(6'-amino-1'-oxo-2'-aminohexylamino)-3-(4-pyridyl)-2-(4-fluorophenyl)-7-azaindole (67); 6-(4'-amino-1'-oxo-butylamino)-3-(4-pyridyl)-2-(4-fluorophenyl)-7-aza-indole (22); 6-(5'-t-butoxycarbonylamino-1'-oxo-2'-t-butoxycarbonylaminopentyl amino)-3-(4-pyridyl)-2-(4-fluorophenyl)-7-aza-indole (68); 6-(5'-amino-1'-oxo-2'-aminopentylamino)-3-(4-pyridyl)-2-(4-fluorophenyl)-7-aza-indole (69); 6-(3'-Methyl-1'-oxo-2'-aminobutylamino)-3-(4-pyridyl)-2-(4-fluorophenyl)-7-aza-indole (73); 6-(4',4'-Dimethyl-1'-oxo-2'-aminopentylamino)-3-(4-pyridyl)-2-(4-fluoro phenyl)-7-aza-indole (75); 6-(5'-amino-1'-oxo-pentylamino)-3-(4-pyridyl)-2-(4-fluorophenyl)-7-aza-indole (77); 6-(6'-amino-1'-oxo-hexylamino)-3-( 4-pyridyl)-2-(4-fluorophenyl)-7-aza-indole (79); 6-(3'-cyclohexyl-1'-oxo-2'-aminopropylamino)-3-(4-pyridyl)-2-(4-fluorophenyl)-7-aza-indole (81); 6-(4'-carboxy-1'-oxo-2'-aminobutylamino)-3-(4-pyridyl)-2-(4-fluorophenyl)-7-aza-indole (83); 6-(3'-hydroxy-1'-oxo-2'-aminobutylamino)-3-(4-pyridyl)-2-(4-fluorophenyl)-7-aza-indole (85); 6-(3'-phenyl-1'-oxo-2'-D,L-aminopropylamino)-3-(4-pyridyl)-2-(4-fluorophenyl)-7-aza-indole (87); 6-(3'-amino-1'-oxo-propylamino)-3-(4-pyridyl)-2-(4-fluorophenyl)-7-aza-indole (91); 6-(2'-t-butoxycarbonylamino-1'-oxo-ethylamino)-3-(4-pyridyl)-2-(4-fluorophenyl)-7-aza-indole (29); 6-(methylsulfonylamino)-3-(4-pyridyl)-2-(4-fluorophenyl)-7-aza-indole (93); 6-(1'-oxo-ethylamino)-3-(4-pyridyl)-2-(4-fluorophenyl)-7-aza-indole (94); 6-(2'-(5-chlorothienyl)sulfonylamino)-3-(4-pyridyl)-2-(4-fluorophenyl)-7-aza-indole (95); 6-(3'-N-phthaloyl-1'-oxo-propylamino)-3-(4-pyridyl)-2-(4-fluorophenyl)-7-aza-indole (98); 3-(4-pyridyl)-2-(4-fluorophenyl)-4,7-diaza-indole (99); 6-(2'-N-t-Butoxycarbonyl-L-prolylamino)-3-(4-pyridyl)-2-(4-fluorophenyl)-7-aza-indole (100); 6-(2'-L-prolylamino)-3-(4-pyridyl)-2-(4-fluorophenyl)-7-aza-indole (101); 6-(2'-Dimethylamino-1'-oxo-ethylamino)-3-(4-pyridyl)-2-(4-fluorophenyl)-7-aza-indole (103); 6-(4'-methylsulfoxo-1'-oxo-2'S-t-butoxycarbonylaminobutylamino)-3-(4-pyridyl)-2-(4-fluorophenyl)-7-aza-indole (108); 6-(4'-methylsulfoxo-1'-oxo-2'S-aminobutylamino)-3-(4-pyridyl)-2-(4-fluorophenyl)-7-aza-indole (109); 6-(3'-(3-pyridyl)-1'-oxo-2'S-t-butoxycarbonylaminopropylamino)-3-(4-pyridyl)-2-(4-fluorophenyl)-7-aza-indole (110); 6-(3'-(3-pyridyl)-1'-oxo-2'S-aminopropylamino)-3-(4-pyridyl)-2-(4-fluorophenyl)-7-aza-indole (111); 6-(N,N-Di-t-butoxycarbonyl-L-histidinylamino)-3-(4-pyridyl)-2-(4-fluorophenyl)-7-aza-indole (112); 6-(L-histidinylamino)-3-(4-pyridyl)-2-(4-fluorophenyl)-7-aza-indole (113); 6-(3(S) 1',2',3',4'-tetrahydro-3'-isoquinolinyloxoamino)-3-(4-pyridyl)-2-( 4-fluorophenyl)-7-aza-indole (115); 6-(3'-phenyl-1'-oxo-2'-(L)-aminopropylamino)-3-(4-pyridyl)-2-(4-fluorophenyl)-7-aza-indole (125); 6-(1'-oxo-2'S-N-methyl-4-methyl-2-aminopentylamino)-3-(4-pyridyl)-2-(4-fluorophenyl)-7-aza-indole (129); 6-(3'-(2-thienyl)-1'-oxo-2'-(L)-aminopropylamino)-3-(4-pyridyl)-2-(4-fluorophenyl)-7-aza-indole (133); 6-(3'-(4-azidophenyl)-1'-oxo-2'S-aminopropylamino)-3-(4-pyridyl)-2-(4-fluorophenyl)-7-aza-indole (135); 6-(3'-(3-benzothienyl)-1'-oxo-2'S-aminopropylamino)-3-(4-pyridyl)-2-(4-fluorophenyl)-7-aza-indole (137); 6-(4'-phenyl-1'-oxo-2'-(L)-aminobutylamino)-3-(4-pyridyl)-2-(4-fluorophenyl)-7-aza-indole (139); 6-(4'-phenyl-1'-oxo-2'-(D)-aminobutylamino)-3-(4-pyridyl)-2-(4-fluorophenyl)-7-aza-indole (141); 6-(2'-amino-1'-oxo-ethylamino)-3-(4-pyridyl)-2-(4-fluorophenyl)-1-isobutoxycarbonyl-7-aza-indole (143); 6-(2'(R,S)-phenylpropylamino)-3-(4-pyridyl)-2-(4-fluoro phenyl)-7-aza-indole (147); 6-(2'(R,S)-ethylhexylamino)-3-(4-pyridyl)-2-(4-fluorophenyl)-7-aza-indole (148); 6-amino-5-fluoro-3-(4-pyridyl)-2-(4-fluorophenyl)-7-aza-indole (28); 6-amino-5-bromo-3-(4-pyridyl)-2-(4-fluorophenyl)-7-aza-indole (27); 6-(2',2'-dimethylpropyl amino)-3-(4-pyridyl)-2-(4-fluorophenyl)-7-aza-indole (151); 6-(isoamylamino)-3-(4-pyridyl)-2-(4-fluorophenyl)-7-aza-indole (152); 6-(2'-ethylbutylamino)-3-(4-pyridyl)-2-(4-fluorophenyl)-7-aza-indole (153); 6-(2'-thienylmethylamino)-3-(4-pyridyl)-2-(4-fluorophenyl)-7-aza-indole (154); 6-(ethylamino)-3-(4-pyridyl)-2-(4-fluorophenyl)-7-aza-indole (156); and 6-(2'-amino-1'-oxo-ethylamino)-3-(4-pyridyl)-2-(4-fluorophenyl)-1-methyl-7-aza-indole (158).

The following compounds had an $IC_{50}$ of less than 1 µM: 6-amino-3-(4-pyridyl)-2-(4-fluorophenyl)-7-aza-indole (17); 6-(3'-(4-iodophenyl)-1'-oxo-2'-aminopropylamino)-3-(4-pyridyl)-2-(4-fluorophenyl)-7-aza-indole (71); 6-(3'-(4-hydroxyphenyl)-1'-oxo-2'-aminopropylamino)- 3-(4-pyridyl)-2-(4-fluorophenyl)-7-aza-indole (89); 6-(2'-amino-1'-oxo-ethylamino)-3-(4-pyridyl)-2-(4-fluoro phenyl)-7-aza-indole (92); 6-(2'S-dimethylamino-1'-oxo-propylamino)-3-(4-pyridyl)-2-(4-fluorophenyl)-7-aza-indole (102); 6-(2'-N-methyl-t-butoxycarbonylamino-1'-oxo-ethylamino)-3-(4-pyridyl)-2-(4-fluorophenyl)-7-aza-indole (104); 6-(2'-N-methyl-amino-1'-oxo-ethylamino)-3-(4-pyridyl)-2-(4-fluorophenyl)-7-aza-indole (105); 6-(4'-N-t-butoxycarbonylisonipecotylamino)-3-(4-pyridyl)-2-(4-fluorophenyl)-7-aza-indole (106); 6-(4'-isonipecotylamino)-3-(4-pyridyl)-2-(4-fluorophenyl)-7-aza-indole (107); 6-(2'-phenyl-1'-oxo-2'R-aminoethylamino)-3-(4-pyridyl)-2-(4-fluorophenyl)-7-aza-indole (117); 6-(2'-phenyl-1-oxo-2'S-aminoethylamino)-3-(4-pyridyl)-2-(4-fluorophenyl)-7-aza-indole (119); 6-(2'-phenyl-1'-oxo-2'R-N-methylaminoethylamino)-3-(4-pyridyl)-2-(4-fluorophenyl)-7-aza-indole (121); 6-(1'-oxo-2'S-aminopropylamino)-3-(4-pyridyl)-2-(4-fluorophenyl)-7-aza-indole (123); 6-(1'-oxo-2'S-N-methylaminopropylamino)-3-(4-pyridyl)-2-(4-fluorophenyl)-7-aza-indole (127); and 6-(1'-oxo-2'R-aminopropylamino)-3-(4-pyridyl)-2-(4-fluorophenyl)-7-aza-indole (131).

In a similar manner to the above described assay involving the LPS induced release of TNF-α from monocytes, compounds of this invention can also be shown to inhibit LPS induced release of IL-1beta, IL-6 and/or IL-8 from monocytes by measuring concentrations of IL-1beta, IL-6 and/or IL-8 by methods well known to those skilled in the art.

Selected compounds from this invention have demonstrated antiinflammatory properties in models of inflammation including the carageenan paw edema model (C. A. Winter et al Proc. Soc. Exp. Biol. Med. (1962) vol 111, p 544; K. F. Swingle, in R. A. Scherrer and M. W. Whitehouse, Eds., Antiinflammatory Agents, Chemistry and Pharmacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666). Also, selected compounds from the class have shown in vivo activity in a LPS mouse model in which serum levels of TNF-α were reduced in the presence of compounds of this invention.

Inhibition of LPS-Induced TNF-α Production in Mice

Male DBA/1LACJ mice were dosed with vehicle or test compounds in a vehicle (the vehicle consisting of 0.5% tragacanth in 0.03 N HCl) 30 minutes prior to lipopolysaccharide (2 mg/kg, I.V.) injection. Ninety minutes after LPS injection, blood was collected and the serum was analyzed by ELISA for TNF levels.

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/ml ethanol); (b) prepare fresh 0.5M DTT (Sigma); (c) Protease Inhibitor Mix (100×): 5 mg leupeptin, 10 mg benzamidine, 40 mg bacitracin and 5 mg soybean trypsin inhibitor per ml DMSO and store aliquots at −20° C.; (d) 250 μM human glucagon (Peninsula): solubilize 0.5 mg vial in 575 μl 0.1N acetic acid (1 pi yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μl 10% BSA (heat-inactivated) and 990 μl Assay Buffer; (g) $^{125}$I-Glucagon (NEN, receptor-grade,. 2200 Ci/mmol): dilute to 50,000 cpm/25 μl in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).

2. Add 10 ml Enzyme-free Dissoc. Fluid and hold for about 4 min. at 37° C.

3. Gently tap cells free, triturate, take aliquot for counting and centrifuge remainder for 5 min. at 1000 rpm.

4. Resuspend pellet in Assay Buffer at 75000 cells per 100 μl.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of I$^{125}$-glucagon binding in the presence of compounds of Formula I. The reagents are combined in 120 uL of assay buffer as follows:

| | Compound/ Vehicle | 250 μM Glucagon | $^{125}$I- Glucagon | CHO/hGLUR Cells |
|---|---|---|---|---|
| Total Binding | —/5 μl | — | 25 μl | 100 μl |
| + Compound | 5 μl/— | — | 25 μl | 100 μl |
| Nonspecific Binding | —/5 μl | 1 μl | 25 μl | 100 μl |

The mixture is incubated for 60 min. at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

In a similar manner to the above described assay involving the LPS induced release of TNF-a from monocytes, compounds of this invention can also be shown to inhibit LPS induced release of IL-1beta, IL-6 and/or IL-8 from monocytes by measuring concentrations of IL-1beta, IL-6 and/or IL-8 by methods well known to those skilled in the art.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 hours on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-1b/mL, and the cells incubated for 18–22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

Cox Activity Determined

After incubation with arachidonic acid, the reactions are stopped by the addition of 1 N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

The following compounds exhibit activities in the Cyclooxygenase assay with $IC_{50}$ values of 20 μM or less:

6-(6'-amino-1'-oxo-hexylamino)-3-(4-pyridyl)-2-(4-fluorophenyl)-7-aza-indole; and 6-(1'-oxo-2'S-N-methylaminopropylamino)-3-(4-pyridyl)-2-(4-fluorophenyl)-7-aza-indole.

The following compounds exhibit activities in the Cyclooxygenase assay with IC50 values of 5 μM or less: 6-(3'.-phenyl-1'-oxo-2'-D,L-aminopropylamino)-3-(4-pyridyl)-2-(4-fluorophenyl)-7-aza-indole; 6-(methylsulfonylamino)-3-(4-pyridyl)-2-(4-fluorophenyl)-7-aza-indole; and 3-(4-pyridyl)-2-(4-fluorophenyl)indole.

This invention further relates to the use of a compound of this invention in the manufacture of a medicament for the prophylaxis and treatment, either acutely or chronically, of TNF-a mediated disease states. In addition, the compounds of this invention are useful in the manufacture of a medicament for treating disease states in which IL-1, IL-6 and/or IL-8 play a role. Also, the compounds of this invention are useful in the manufacture of a analgesic medicament and a medicament for treating pain disorders, such as hyperalgesia. The compounds of the present invention also are useful in the manufacture of a medicament to prevent the production of prostaglandins by inhibition of enzymes in the human arachidonic acid/prostaglandin pathway.

This invention also relates to a pharmaceutical composition comprising a compound of this invention and a pharmaceutically acceptable carrier, and if desired other active ingredients. The compounds of this invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art.

All of the compounds of this invention are useful in the prophylaxis and treatment of TNF-a mediated disease states. The compounds are also useful in the prophylaxis and treatment of disease states in which IL-1, IL-6, and IL-8 play a role. Preferably, the compounds of this invention are useful in the prophylaxis and treatment of rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis.; anaphylaxis; contact dermatitis; asthma; antiviral therapy including those viruses sensitive to TNF-a inhibition—HIV-1, HIV-2, HIV-3, cytomegalovirus (CMV), influenza, adenovirus, and the herpes viruses including HSV-1, HSV-2, and herpes zoster; muscle degeneration; cachexia; Reiter's syndrome; type II diabetes; bone resorption diseases; graft vs. host reaction; ischemia reperfusion injury; brain trauma; atherosclerosis; Alzheimer's discease; multiple.sclerosis; cerebral malaria; sepsis; septic shock; toxic shock syndrome; fever and mylagias due to infection.

In addition to inhibiting the production of TNF-α, compounds of this invention can also reduce levels of other cytokines including but not limited to IL-1, IL-6 or IL-8. Reducing elevated levels of these inflammatory cytokines to basal levels or below is favorable in controlling, slowing progression, or possibly alleviating many disease states.

The present invention provides a method of treating a disease state in which cytokine levels are elevated which comprises administering an effective amount of a compound of this invention. Compounds of this invention are of use in the prophylaxis and acute or chronic therapy of any disease state in a human, or other mammal, which is exacerbated by or mediated by elevated or unregulated IL-1, IL-6, IL-8 and/or TNF-a production by such mammal's cells, such as, but not limited to monocytes, macrophages, and glial cells. More preferably, this invention relates to a method of lowering the levels of TNF-a and/or IL-1 in a mammal in need thereof which comprises administering an effective dose of a compound of this invention or a pharmaceutical composition thereof. In addition, this invention relates to a method of lowering the levels of IL-6 and/or IL-8 in a mammal in need thereof which comprises administering an effective dose of a compound of this invention or a pharmaceutical composition thereof.

Accordingly, the compounds of this invention or a pharmaceutical composition thereof are useful in the treatment or prophylaxis of a number of disease states including rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; Alzheimer's disease; stroke; myocardial infarction; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster, all of which are sensitive to TNF-α and/or IL-1 inhibition or glucagon antagonism, will also be positively effected by the compounds and methods of the invention.

The compounds of the present invention also may possess analgesic properties and may be useful for the treatment of pain disorders, such as hyperalgesia due to excessive IL-1. The compounds of the present invention may also prevent the production of prostaglandins by inhibition of enzymes in the human arachidonic acid/prostaglandin pathway, including cyclooxygenase (WO 96/03387, incorporated herein by reference in its entirety).

Because of their ability to lower TNF-a and IL-1 concentrations or inhibit glucagon binding to its receptor, the compounds of the invention are also useful research tools for studying the physiology associated with blocking these effects.

In another aspect, this invention comprises the use of a compound of the invention, or pharmaceutically acceptable salts thereof, in the manufacture of a medicament for the treatment either acutely or chronically of a TNF-α, IL-1β, IL-6, and/or IL-8 mediated disease state, including those described previously.

In still another aspect, this invention provides a pharmaceutical composition comprising an effective TNF-α, IL-1β, IL-6, and/or IL-8 lowering amount and/or effective plasma glucose level lowering amount of a compound of the invention and a pharmaceutically acceptable carrier or diluent, and if desired other active ingredients. The compounds of the invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art using standard methods.

For the treatment of TNF-α, IL-1β, IL-6, and IL-8 mediated diseases and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

For the prophylaxis and treatment of disease states, the compounds of the present invention may be administered orally, parentally, or by inhalation spray, rectally, or topically in dosage unit formulations containing conventional pharmaceutically acceptable carriers, adjuvants and vehicles. The term parenteral as used herein includes, subcutaneous, intravenous, intramuscular, intrasternal, infusion techniques or intraperitoneally.

The amount of active ingredient that may be combined with the carrier materials to produce a single dosage form will vary depending upon the host treated and the particular mode of administration.

The dosage regimen for treating a disease state with the compounds of this invention and/or compositions of this invention is based on a variety of factors, including the type of disease, the age, weight, sex and medical condition of the patient, the severity of the condition, the route of administration, pharmacological considerations such as the activity, efficacy, pharmacokinetic and toxicology profiles of the particular compound employed, whether a drug delivery system is utilized and whether the compound is administered as part of a drug combination. Thus the dosage regimen may vary widely. Dosage levels of the order from about 0.01 mg to 80 mg per kilogram of body weight per day, preferably from about 0.5 mg to 30 mg/kg, more preferably from about 1 mg to 15 mg/kg are useful for all methods of use disclosed herein. The pharmaceutically active compounds of this invention can be processed in accordance with convential methods of pharmacy to produce medicinal agents for administration to patients, mammals including humans.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 250 mg, preferably from about 25 to 150 mg. A suitable daily dose for a human or other mammal may vary widely depending on the condition of the patient and other factors.

The compounds of this invention may also be administered by injection as a composition with suitable carriers including saline, dextrose, or water. The daily parenteral dosage regimen will be from about 0.1 to about 80 mg/kg of total body weight, preferably from about 0.5 to about 30 mg/kg, and more preferably from about 1 mg to 15 mg/kg.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

A suitable topical dose of compounds of this invention is 0.1 mg to 150 mg administered one to four, preferably two or three times daily. For topical administration, the active ingredient may comprise from 0.001% to 10% w/w, e.g. from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin such as liniments, lotions, ointments, creams, or pastes and drops suitable for administration to the eye, ear, or nose.

For administration, the compounds of this invention are ordinarily combined with one or more adjuvants appropriate-for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, benzyl alcohol, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form including granules, powders or suppositories or in a liquid form such as solutions, suspensions, or emulsions. The pharmaceutical compositions may be subjected to conventional pharmaceutical operations such as sterilization and/or may contain conventional adjuvants, such as preservatives, stabilizers, wetting agents, emulsifiers, buffers, etc.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of this invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of this invention can likewise be obtained by utilizing optically active starting materials. These isomers may be in the form of a free acid, a free base, an ester or a salt.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

While the compounds of the invention can be administered as the sole active pharmaceutical agent, they can also be used in combination with one or more other agents. When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula

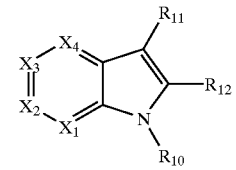

or a pharmaceutically acceptable salt thereof, wherein
$X_1$ is N; $X_2$ is CH or $CR_2$; $X_3$ is CH or $CR_3$; and $X_4$ is N;
wherein $R_2$ and $R_3$ are each independently —Z—Y, provided that (1) the total number of aryl, heteroaryl, cycloalkyl and heterocyclyl radicals in each —Z—Y is 0–3; and (2) the combined total number of aryl, heteroaryl, cycloalkyl and heterocyclyl radicals in $R_2$ and $R_3$ is 0–4;
wherein each Z is independently a
  (1) bond;
  (2) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio, cyano or halo, and (b) 1–2 radicals of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;
  (3) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (4) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

each Y is independently a
  (1) hydrogen radical, provided Z is other than a bond;
  (2) halo, cyano or nitro radical;
  (3) —C(O)—$R_{20}$, —C(O)—O$R_{21}$, —C(O)—N$R_5R_{21}$ or —C(N$R_5$)—N$R_5R_{21}$ radical;
  (4) —O$R_{21}$, —O—C(O)—$R_{21}$, —O—C(O)—N$R_5R_{21}$ or —O—C(O)—N$R_{22}$—S(O)$_2$—$R_{20}$ radical;
  (5) —S$R_{21}$, —S(O)—$R_{20}$, —S(O)$_2$—$R_{20}$, —S(O)$_2$—N$R_5R_{21}$, —S(O)$_2$—N$R_{22}$—C(O)—$R_{21}$, —S(O)$_2$—N$R_{22}$—C(O)—O$R_{20}$ or —S(O)$_2$—N$R_{22}$—C(O)—N$R_5R_{21}$ radical; or
  (6) —N$R_5R_{21}$, —N$R_{22}$—C(O)—$R_{21}$, —N$R_{22}$—C(O)—O$R_{20}$, —N$R_{22}$—C(O)—N$R_5R_{21}$, —N$R_{22}$—C(N$R_5$)—N$R_5R_{21}$, —N$R_{22}$—S(O)$_2$—$R_{20}$ or —N$R_{22}$—S(O)$_2$—N$R_5R_{21}$ radical;

wherein each $R_5$ is independently a
  (1) hydrogen radical;
  (2) alkyl, alkenyl or alkynyl radical optionally substituted by 1–3 radicals of amino, alkylamino, dialkylamino, hydroxy, alkoxy, alkylthio, cyano or halo; or
  (3) aryl, heteroaryl, aralkyl, heteroaralkyl, heterocyclyl, heterocyclylalkyl, cycloalkyl or cycloalkylalkyl radical optionally substituted by 1–3 radicals of amino, alkylamino, dialkylamino, hydroxy, alkoxy, alkylthio, cyano, alkyl or haloalkyl; and wherein each $R_{20}$ is independently an
  (1) alkyl, alkenyl or alkynyl radical optionally substituted by 1–3 radicals of (a) —CO$_2R_{23}$, amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, cyano or halo radicals or (b) aralkoxy, aralkylthio, aralkylsulfonyl, cycloalkyl, heterocyclyl, aryl or heteroaryl radicals optionally substituted by 1–3 radicals of amino, alkylamino, dialkylamino, alkanoylamino, alkoxycarbonylamino, alkylsulfonylamino, alkanoyl, alkoxycarbonyl, hydroxy, alkoxy, alkylthio, alkylsulfinyl, alkylsulfonyl, cyano, halo, alkyl or haloalkyl;
  (2) heterocyclyl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, alkyl or haloalkyl; or
  (3) aryl or heteroaryl radical optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;

each $R_{21}$ is independently hydrogen radical or $R_{20}$;

each $R_{22}$ is independently a
  (1) hydrogen radical;
  (2) alkyl radical optionally substituted by a radical of heterocyclyl, aryl or heteroaryl, wherein the heterocyclyl, aryl or heteroaryl radical is optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or
  (3) heterocyclyl, aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; and each $R_{23}$ is independently a (a) hydrogen or alkyl radical, or (b) aryl, heteroaryl, aralkyl or heteroaralkyl radical optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; and $R_{10}$ is a hydrogen, $R_{30}$, —C(O)—$R_{29}$, —C(O)—O$R_{30}$, —C(O)—N$R_{31}R_{32}$, —S(O)$_2$—$R_{30}$ or —S(O)$_2$—N$R_{31}R_{32}$ radical;

$R_{11}$ and $R_{12}$ are each independently an aryl or heteroaryl radical optionally substituted by 1–3 radicals of
  (1) $R_{30}$;
  (2) halo or cyano radicals;
  (3) —C(O)—$R_{30}$, —C(O)—O$R_{29}$, —C(O)—N$R_{31}R_{32}$ or —C(N$R_{31}$)—N$R_{31}R_{32}$ radicals;
  (4) —O$R_{29}$, —O—C(O)—$R_{29}$, —O—C(O)—N$R_{31}R_{32}$ or —O—C(O)—N$R_{33}$—S(O)$_2$—$R_{30}$ radicals;
  (5) —S$R_{29}$, —S(O)—$R_{30}$, —S(O)$_2$—$R_{30}$, —S(O)$_2$—N$R_{31}R_{32}$, —S(O)$_2$—N$R_{33}$—C(O)—$R_{30}$, —S(O)$_2$—N$R_{33}$—C(O)—O$R_{30}$ or —S(O)$_2$—N$R_{33}$—C(O)—N$R_{31}R_{32}$ radicals; or
  (6) —N$R_{31}R_{32}$, —N$R_{33}$—C(O)—$R_{29}$, —N$R_{33}$—C(O)—O$R_{30}$, —N$R_{33}$—C(O)—N$R_{31}R_{32}$, —N$R_{33}$—C(N$R_{31}$)—N$R_{31}R_{32}$, —N$R_{33}$—S(O)$_2$—$R_{30}$ or —N$R_{33}$—S(O)$_2$—N$R_{31}R_{32}$ radicals;
    provided that $R_{11}$ and $R_{12}$ are not both phenyl, 4-methoxyphenyl or 4-chlorophenyl radicals; and the total number of aryl, heteroaryl, cycloalkyl and heterocyclyl radicals substituted on each of $R_{11}$ and $R_{12}$ is 0–1;

wherein each $R_{30}$ is independently an
  (1) alkyl, alkenyl or alkynyl radical optionally substituted by 1–3 radicals of (a) —N$R_{31}R_{31}$, —CO$_2R_{23}$, hydroxy, alkoxy, alkylthio, alkylsulfinyl, alkylsulfonyl, cyano or halo radicals or (b) aralkoxy, aralkylthio, aralkylsulfonyl, heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;
  (2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or
  (3) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

each $R_{29}$ is independently hydrogen radical or $R_{30}$;

each $R_{31}$ and $R_{32}$ are each independently a (1) hydrogen radical;
(2) alkyl radical optionally substituted by an cycloalkyl, aryl, heterocyclyl or heteroaryl radical, wherein the cycloalkyl, aryl, heterocyclyl or heteroaryl radical is optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or
(3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; and wherein each $R_{33}$ is independently a
(1) hydrogen radical; or
(2) alkyl radical optionally substituted by a heterocyclyl, aryl or heteroaryl radical, wherein the heterocyclyl, aryl or heteroaryl radical is optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; and wherein heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; aryl is a phenyl or naphthyl radical; and heteroaryl is radical of a monocyclic or bicyclic aromatic heterocyclic ring system having 5–6 ring members per ring, wherein 1–3 ring members are oxygen, sulfur or nitrogen heteroatoms, which is optionally henzo-fused or saturated $C_3$–$C_4$-carbocyclic-fused.

2. The compound of claim 1 or a pharmaceutically acceptable salt thereof, wherein $X_1$ is N; $X_2$ is CH or $CR_2$; $X_3$ is CH or $CR_3$; and $X_4$ is N;
wherein $R_2$ and $R_3$ are each independently —Z—Y, provided that
(1) the total number of aryl, heteroaryl, cycloalkyl and heterocyclyl radicals in each —Z—Y is 0–3; and (2) the combined total number of aryl, heteroaryl, cycloalkyl and heterocyclyl radicals in $R_2$ and $R_3$ is 0–4;

each Z is independently a
(1) bond;
(2) $C_1$–$C_8$ alkyl, $C_2$–$C_8$ alkenyl or $C_2$–$C_8$ alkynyl radical optionally substituted by 1–3 radicals of (a) amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano or halo radicals or (b) heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;
(3) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

each Y is independently a
(1) hydrogen radical, provided Z is other than a bond;
(2) halo, cyano or nitro radical;
(3) —C(O)—$R_{20}$, —C(O)—$OR_{21}$, —C(O)—$NR_5R_{21}$ or —C($NR_5$)—$NR_5R_{21}$ radical;
(4) —$OR_{21}$, —O—C(O)—$R_{21}$, —O—C(O)—$NR_5R_{21}$ or —O—C(O)—$NR_{22}$—S(O)$_2$—$R_{20}$ radical;
(5) —$SR_{21}$, —S(O)—$R_{20}$, —S(O)$_2$—$R_{20}$, —S(O)$_2$—$NR_5R_{21}$, —S(O)$_2$—$NR_{22}$—C(O)—$R_{21}$, —S(O)$_2$—$NR_{22}$—C(O)—$OR_{20}$ or —S(O)$_2$—$NR_{22}$—C(O)—$NR_5R_{21}$ radical; or
(6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

each $R_5$ is independently a
(1) hydrogen radical;
(2) $C_1$–$C_8$ alkyl, $C_2$—$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano or halo; or
(3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

each $R_{20}$ is independently a
(1) $C_1$–$C_8$ alkyl, $C_2$–$C_8$ alkenyl or $C_2$–$C_8$ alkynyl radical optionally substituted by 1–3 radicals of (a) —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy) carbonylamino, N-(($C_1$–$C_4$ alkoxy)carbonyl)-N-($C_1$–$C_4$ alkyl) amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano or halo radicals or (b) aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)

carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

each $R_{21}$ is independently hydrogen radical or $R_{20}$;

each $R_{22}$ is independently a
  (1) hydrogen radical;
  (2) $C_1$–$C_4$ alkyl radical optionally substituted by a radical of heterocyclyl, aryl or heteroaryl, wherein the heterocyclyl, aryl or heteroaryl radical is optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or
  (3) heterocyclyl, aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

each $R_{23}$ is independently a (a) hydrogen or $C_1$–$C_4$ alkyl radical or (b) aryl, heteroaryl, aryl-$C_1$–$C_4$-alkyl or heteroaryl-$C_1$–$C_4$-alkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

$R_{10}$ is a hydrogen, $R_{30}$, —C(O)—$R_{29}$, —C(0) —O$R_{30}$, —C(O)—N$R_{31}R_{32}$, —S(O)$_2$—$R_{30}$ or —S(O)$_2$—N$R_{31}R_{32}$ radical;

$R_{11}$ and $R_{12}$ are each independently an aryl or heteroaryl radical optionally substituted by 1–3 radicals of
  (1) $R_{30}$;
  (2) halo or cyano radicals;
  (3) —C(O)—$R_{30}$, —C(O)—O$R_{29}$, —C(O)—N$R_{31}R_{32}$ or —C(N$R_{31}$)—N$R_{31}R_{32}$ radicals;
  (4) —O$R_{29}$, —O—C(O)—$R_{29}$, —O—C(O)—N$R_{31}R_{32}$ or —O—C(O)—N$R_{33}$—S(O)$_2$—$R_{30}$ radicals;
  (5) —S$R_{29}$, —S(O)—$R_{30}$, —S(O)$_2$—$R_{30}$, —S(O)$_2$—N$R_{31}R_{32}$, —S(O)$_2$—N$R_{33}$—C(O)—$R_{30}$, —S(O)$_2$—N$R_{33}$—C(O)—O$R_{30}$ or —S(O)$_2$—N$R_{33}$—C(O)—N$R_{31}R_{32}$ radicals; or
  (6) —N$R_{31}R_{32}$, —N$R_{33}$—C(O)—$R_{29}$, —N$R_{33}$—C(O)—O$R_{30}$, —N$R_{33}$—C(O)—N$R_{31}R_{32}$, —N$R_{33}$—C(N$R_{31}$)—N$R_{31}R_{32}$, —N$R_{33}$—S(O)$_2$—$R_{30}$ or —N$R_{33}$—S(O)$_2$—N$R_{31}R_{32}$ radicals;
    provided that $R_{11}$ and $R_{12}$ are not both phenyl, 4-methoxyphenyl or 4-chlorophenyl radicals; and the total number of aryl, heteroaryl, cycloalkyl and heterocyclyl radicals substituted on each of $R_{11}$ and $R_{12}$ is 0–1;

each $R_{30}$ is independently a
  (1) $C_1$–$C_4$ alkyl, $C_2$–$C_4$ alkenyl or $C_2$–$C_4$ alkynyl radical optionally substituted by 1–3 radicals of (a) —N$R_{31}R_{31}$, —CO$_2R_{23}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano or halo radicals or (b) aryl-$C_1$–$C_4$-alkoxy, aryl-$C_1$–$C_4$-alkylthio, aryl-$C_1$–$C_4$-alkylsulfonyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;
  (2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
  (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

each $R_{29}$ is independently hydrogen radical or $R_{30}$;

each $R_{31}$ and $R_{32}$ are each independently a
  (1) hydrogen radical;
  (2) $C_1$–$C_4$ alkyl radical optionally substituted by an $C_3$–$C_8$ cycloalkyl, aryl, heterocyclyl or heteroaryl radical, wherein the cycloalkyl, aryl, heterocyclyl or heteroaryl radical is optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$→$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
  (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and each $R_{33}$ is independently a
  (1) hydrogen radical; or
  (2) $C_1$–$C_4$ alkyl radical optionally substituted by a heterocyclyl, aryl or heteroaryl radical, wherein the heterocyclyl, aryl or heteroaryl radical is optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and wherein heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; aryl is a phenyl or naphthyl radical; and heteroaryl is radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

3. The compound of claim 2 or a pharmaceutically acceptable salt thereof, wherein each Z is independently a
(1) bond;
(2) $C_1$–$C_8$ alkyl, $C_2$–$C_8$ alkenyl or $C_2$–$C_8$ alkynyl radical optionally substituted by 1–3 radicals of (a) amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo radicals or (b) heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;
(3) heterocyclyl radical optionally substituted by 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

each $R_5$ is independently a
(1) hydrogen radical;
(2) $C_1$–$C_4$ alkyl, $C_2$–$C_5$ alkenyl or $C_2$–$C_5$ alkynyl radical optionally substituted by 1–3 radicals of amino, $C_1$–$C_4$ alkylamino, di-($C_1$—$C_4$-alkyl)amino, hydroxy, $C_1$–$C_4$ alkoxy, $C_1$–$C_4$ alkylthio or halo; or
(3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

each $R_{20}$ is independently a
(1) $C_1$–$C_8$ alkyl, $C_2$–$C_5$ alkenyl or $C_2$–$C_5$ alkynyl radical optionally substituted by 1–3 radicals of (a) —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy) carbonyl)-N-($C_1$–$C_4$ alkyl) amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo radicals or (b) aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

each $R_{21}$ is independently hydrogen radical or $R_{20}$;
each $R_{30}$ is independently a
(1) $C_1$–$C_4$ alkyl radical optionally substituted by 1–3 radicals of
(a) —$NR_{31}R_{31}$, $C_1$–$C_4$ alkoxy-carbonyl, hydroxy, $C_1$–$C_4$ alkoxy, $C_1$–$C_4$ alkylthio;
(b) phenoxycarbonyl or phenylmethoxycarbonyl optionally substituted by 1–3 radicals of amino, alkylamino, di-($C_1$–$C_4$-alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or trifluoromethyl; or
(c) phenyl-$C_1$–$C_4$-alkoxy, phenyl-$C_1$–$C_4$-alkylthio, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;
(2) $C_1$–$C_4$ haloalkyl of 1–3 halo radical; or
(3) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl;

each $R_{29}$ is independently hydrogen radical or $R_{30}$;
each $R_{31}$ is independently a
(1) hydrogen radical; or
(2) $C_1$–$C_4$ alkyl radical optionally substituted by an phenyl or heteroaryl radical, wherein the phenyl or heteroaryl radical is optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, $C_1$–$C_4$ alkyl or trifluoromethyl radicals; and each $R_{32}$ is independently a
(1) hydrogen radical;
(2) $C_1$–$C_4$ alkyl radical optionally substituted by an $C_3$–$C_6$ cycloalkyl, aryl, heterocyclyl or heteroaryl radical, wherein the cycloalkyl, aryl, heterocyclyl or heteroaryl radical is optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl, heteroaryl, heterocyclyl or $C_3$—$C_6$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and each $R_{33}$ is independently a hydrogen or $C_1$–$C_4$ alkyl radical.

4. The compound of claim 3 or a pharmaceutically acceptable salt thereof, wherein $R_2$ and $R_3$ are each independently —Z—Y, provided that (1) the total number of aryl, heteroaryl, cycloalkyl and heterocyclyl radicals in each —Z—Y is 0–3; and (2) the combined total number of aryl, heteroaryl, cycloalkyl and heterocyclyl radicals in $R_2$ and $R_3$ is 0–3;

each Z is independently a
  (1) bond;
  (2) $C_1$–$C_8$ alkyl or $C_2$–$C_8$ alkenyl radical optionally substituted by 1–3 radicals of (a) amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio or halo radicals or (b) heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;
  (3) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl radicals; or
  (4) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

each Y is independently a
  (1) hydrogen radical, provided Z is other than a bond;
  (2) halo radical;
  (3) —C(O)—$R_{20}$, —C(O)—$OR_{21}$, —C(O)—$NR_5R_{21}$ or —C($NR_5$)—$NR_5R_{21}$ radical;
  (4) —$OR_{21}$, —O—C(O)—$R_{21}$ or —O—C(O)—$NR_5R_{21}$ radical;
  (5) —$SR_{21}$, —S(O)—$R_{20}$, —S(O)$_2$—$R_{20}$ or —S(O)$_2$—$NR_5R_{21}$ radical; or
  (6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

each $R_5$ is independently a
  (1) hydrogen radical;
  (2) $C_1$–$C_4$ alkyl or $C_2$–$C_5$ alkenyl radical optionally substituted by 1–3 radicals of amino, di-($C_1$–$C_4$-alkyl)amino, hydroxy, $C_1$–$C_4$ alkoxy, $C_1$–$C_4$ alkylthio or halo; or
  (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radical optionally substituted by 1–3 radicals of amino, di-($C_1$–$C_4$-alkyl)amino, hydroxy, $C_1$–$C_4$ alkoxy, $C_1$–$C_4$ alkylthio, cyano, $C_1$–$C_4$ alkyl or $C_1$–$C_2$ haloalkyl of 1–3 halo radicals;

each $R_{20}$ is independently a
  (1) $C_1$–$C_8$ alkyl or $C_2$–$C_5$ alkenyl radical optionally substituted by 1–3 radicals of (a) —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl) amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo radicals or (b) aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;
  (2) heterocyclyl radical optionally substituted by 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, ($C_1$–$C_4$ alkoxy)carbonyl, hydroxy, $C_1$–$C_4$ alkoxy, $C_1$–$C_4$ alkylthio or $C_1$–$C_4$ alkyl; or
  (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_2$ haloalkyl of 1–3 halo radicals;

each $R_{21}$ is independently hydrogen radical or $R_{20}$;

each $R_{22}$ is independently a
  (1) hydrogen radical; or
  (2) $C_1$–$C_4$ alkyl radical optionally substituted by a radical of phenyl or heteroaryl, wherein the phenyl or heteroaryl radical is optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

each $R_{23}$ is independently a (a) hydrogen or $C_1$–$C_4$ alkyl radical or (b) phenyl, heteroaryl, phenyl-$C_1$–$C_2$-alkyl or heteroaryl-$C_1$–$C_2$-alkyl optionally substituted by 1–3 radicals of amino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

$R_{10}$ is a hydrogen, $R_{30}$, —C(O)—$R_{29}$, —C(O)—$NR_{31}R_{32}$, —S(O)$_2$—$R_{30}$ or —S(O)$_2$—$NR_{31}R_{32}$ radical;

$R_{11}$ and $R_{12}$ are each independently an aryl or heteroaryl radical optionally substituted by 1–2 radicals of
  (1) $R_{30}$;
  (2) halo or cyano radicals;
  (3) —C(O)—$R_{30}$, —C(O)—$OR_{29}$, —C(O)—$NR_{31}R_{32}$ or —C($NR_{31}$)—$NR_{31}R_{32}$ radicals; or
  (4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$, —$NR_{33}$—C(O)—$R_{29}$ or —$NR_{33}$—C(O)—$OR_{30}$ radicals; provided that $R_{11}$ and $R_{12}$ are not both phenyl, 4-methoxyphenyl or 4-chlorophenyl radicals; and the total number of aryl, heteroaryl, cycloalkyl and heterocyclyl radicals substituted on each of $R_{11}$ and $R_{12}$ is 0–1;

each $R_{30}$ is independently a
  (1) $C_1$–$C_4$ alkyl radical optionally substituted by an (a) amino, $C_1$–$C_4$ alkylamino, di-($C_1$–$C_4$-alkyl) amino, hydroxy or $C_1$–$C_4$ alkoxy radical; or
  (b) heterocyclyl, phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

(2) $C_1$–$C_2$ haloalkyl of 1–3 halo radical; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio., cyano, halo, $C_1$–$C_4$ alkyl or trifluoromethyl radicals;

each $R_{29}$ is independently hydrogen radical or $R_{30}$;

each $R_{31}$ is independently a hydrogen or $C_1$–$C_4$ alkyl radical; and each $R_{32}$ is independently a (1) hydrogen radical;

(2) $C_1$–$C_4$ alkyl radical optionally substituted by phenyl or heteroaryl radical, wherein the phenyl or heteroaryl radical is optionally substituted by 1–3 radicals to amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl radicals; or (3) phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy) carbonylamino, hydroxy, $C_1$–$C_4$ alkoxy, $C_1$–$C_4$ alkyl or trifluoromethyl radicals; and each $R_{33}$ is independently a hydrogen or methyl radical; and wherein heterocyclyl is a radical of a monocyclic saturated heterocyclic ring system having 5–6 ring members, wherein 1–3 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–3 ring members are oxygen, sulfur or nitrogen heteroatoms, which is optionally benzo-fused or saturated $C_3$–$C_4$-carbocyclic-fused.

5. The compound of claim 4, or a pharmaceutically acceptable salt thereof, wherein each Z is independently a (1) bond;

(2) $C_1$–$C_4$ alkyl or $C_2$–$C_5$ alkenyl radical optionally substituted by 1–3 radicals of (a) amino, di-($C_1$–$C_2$ alkyl)amino, $C_1$–$C_5$ alkanoylamino, ($C_1$–$C_4$ alkoxy) carbonylamino, hydroxy, $C_1$–$C_2$ alkoxy, $C_1$–$C_2$ alkylthio or halo radicals or (b) heterocyclyl, aryl or heteroaryl radicals optionally substituted by 1–3 radicals of amino, $C_1$–$C_4$ alkylamino, di-($C_1$–$C_2$ alkyl)amino, $C_1$–$C_5$ alkanoylamino, ($C_1$–$C_4$ alkoxy) carbonylamino, hydroxy, $C_1$–$C_4$ alkoxy, $C_{114}$ $_{C4}$ alkylthio, cyano, halo, $C_1$–$C_4$ alkyl or trifluoromethyl radicals;

(3) heterocyclyl radical optionally substituted by 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or $C_1$–$C_4$ alkyl radicals; or (4) aryl or heteroaryl radical optionally substituted by 1–3 radicals of amino, di-($C_1$–$C_2$ alkyl)amino, $C_1$–$C_5$ alkanoylamino, ($C_1$–$C_4$ alkoxy) carbonylamino, hydroxy, $C_1$–$C_2$ alkoxy, $C_1$–$C_2$ alkylthio, cyano, halo, $C_1$–$C_4$ alkyl or trifluoromethyl radicals;

each $R_5$ is independently a (1) hydrogen radical;

(2) $C_1$–$C_4$ alkyl radical optionally substituted by 1–3 radicals of amino, di-($C_1$–$C_2$-alkyl)amino, hydroxy, $C_1$–$C_2$ alkoxy, $C_1$–$C_2$ alkylthio or halo; or (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radical optionally substituted by 1–3 radicals of amino, di-($C_1$–$C_2$-alkyl)amino, hydroxy, $C_1$–$C_2$ alkoxy, $C_1$–$C_2$ alkylthio, methoxy, methylthio, cyano, $C_1$–$C_4$ alkyl or trifluoromethyl radicals;

each $R_{22}$ is independently a hydrogen or $C_1$–$C_4$ alkyl radical;

each $R_{23}$ is independently a (a) hydrogen or $C_1$–$C_4$ alkyl radical or (b) phenyl, heteroaryl, phenyl-$C_1$–$C_2$-alkyl or heteroaryl-$C_1$–$C_2$-alkyl optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;

$R_{11}$ and $R_{12}$ are each independently an aryl or heteroaryl radical optionally substituted by 1–2 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals; or (4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;

provided that $R_1$, and $R_{12}$ are not both phenyl, 4-methoxyphenyl or 4-chlorophenyl radicals; and the total number of aryl, heteroaryl, cycloalkyl and heterocyclyl radicals substituted on each of $R_{11}$, and $R_{12}$ is 0–1;

each $R_{30}$ is independently a (1) $C_1$–$C_4$ alkyl radical optionally substituted by a phenyl or heteroaryl radical, wherein the phenyl or heteroaryl radical is optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

(2) trifluoromethyl radical; or (3) aryl or heteroaryl radical optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

each $R_{29}$ is independently hydrogen radical or $R_{30}$; and each $R_{32}$ is independently a (1) hydrogen or $C_1$–$C_4$ alkyl radical;

(2) $C_1$–$C_2$ alkyl radical substituted by phenyl or heteroaryl radical, wherein the phenyl or heteroaryl radical is optionally substituted by 1–3 radicals of amino, di-($C_1$–$C_2$ alkyl)amino, acetamido, hydroxy, $C_1$–$C_2$ alkoxy, $C_1$–$C_4$ alkyl or trifluoromethyl radicals; or (3) phenyl or heteroaryl radical optionally substituted by 1–3 radicals of amino, di-($C_1$–$C_2$ alkyl)amino, acetamido, hydroxy, $C_1$–$C_2$ alkoxy, $C_1$–$C_4$ alkyl or trifluoromethyl radicals; and wherein heterocyclyl is a radical of a monocyclic saturated heterocyclic ring system having 5–6 ring members, wherein 1–2 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–2 ring members are oxygen, sulfur or nitrogen heteroatoms, which is optionally benzo-fused.

6. The compound of claim 5 or a pharmaceutically acceptable salt thereof, wherein each Z is independently a
  (1) bond;
  (2) $C_1$–$C_4$ alkyl or $C_2$–$C_5$ alkenyl radical optionally substituted by 1–3 radicals of (a) amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or halo radicals or (b) aryl or heteroaryl radicals optionally substituted by 1–2 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals; or
  (3) aryl or heteroaryl radical optionally substituted by 1–3 radicals of amino, di-($C_1$–$C_2$ alkyl)amino, acetamido, ($C_1$–$C_4$ alkoxy)carbonylamino, hydroxy, $C_{114\ C2}$ alkoxy, $C_1$–$C_2$ alkylthio, cyano, halo, $C_1$–$C_4$ alkyl or trifluoromethyl radicals;

each Y is independently a
  (1) hydrogen radical, provided Z is other than a bond;
  (2) halo radical;
  (3) —C(O)—$R_{20}$, —C(O)—$OR_{21}$ or —C(O)—$NR_5R_{21}$ radical;
  (4) —$OR_{21}$, —$SR_{21}$, —S(O)—$R_{20}$, —S(O)$_2$—$R_{20}$ or —S(O)$_2$—$NR_5R_{21}$ radical; or
  (5) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—S(O)$_2$—$R_{20}$ or —$NR_{22}$—S(O)$_2$—$NR_5R_{21}$ radical;

each $R_5$ is independently a
  (1) hydrogen radical;
  (2) $C_1$–$C_4$ alkyl radical optionally substituted by 1–3 halo radicals; or
  (3) phenyl-$C_1$–$C_2$-alkyl or heteroaryl-$C_1$–$C_2$-alkyl, radical optionally substituted by 1–3 radicals of amino, dimethylamino, hydroxy, methoxy, methylthio, methyl or trifluoromethyl radicals;

each $R_{20}$ is independently a
  (1) $C_1$–$C_8$ alkyl or $C_2$–$C_5$ alkenyl radical optionally substituted by 1–3 radicals of (a) —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo radicals or (b) aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;
  (2) heterocyclyl radical optionally substituted by 1–2 radicals of amino, di-($C_1$–$C_4$ alkyl)amino, ($C_1$–$C_4$ alkoxy)carbonylamino, ($C_1$–$C_4$ alkoxy)carbonyl, hydroxy, $C_1$–$C_4$ alkoxy, $C_1$–$C_4$ alkylthio or $C_1$–$C_4$ alkyl; or
  (3) aryl or heteroaryl radical optionally substituted by 1–2 radicals of amino, di-($C_1$–$C_4$ alkyl)amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl radicals;

each $R_{21}$ is independently hydrogen radical or $R_{20}$;

each $R_{23}$ is independently a (a) hydrogen or $C_1$–$C_4$ alkyl radical or (b) phenyl-$C_1$–$C_2$-alkyl or heteroaryl-$C_1$–$C_2$-alkyl optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;

$R_{11}$ and $R_{12}$ are each independently an aryl or heteroaryl radical optionally substituted by 1–2 radicals of
  (1) $R_{30}$;
  (2) halo or cyano radicals; or
  (3) —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals,
    provided that $R_{11}$ and $R_{12}$ are not both phenyl, 4-methoxyphenyl or 4-chlorophenyl radicals; and the total number of aryl, heteroaryl, cycloalkyl and heterocyclyl radicals substituted on each of $R_{11}$ and $R_{12}$ is 0–1;

each $R_{30}$ is independently a
  (1) $C_1$–$C_4$ alkyl radical optionally substituted by a phenyl or heteroaryl radical, wherein the phenyl or phenyl or heteroaryl radical is optionally substituted by 1–3 radicals of amino, dimethylamino, acetamido, hydroxy, halo, methoxy, methyl or trifluoromethyl radicals;
  (2) trifluoromethyl radical; or
  (3) aryl or heteroaryl radical optionally substituted by 1–3 radicals of amino, dimethylamino, acetamido, hydroxy, halo, methoxy, methyl or trifluoromethyl radicals;

each $R_{29}$ is independently hydrogen radical or $R_{30}$;

each $R_{31}$ is independently a hydrogen, methyl or ethyl radical; and each $R_{32}$ is independently a
  (1) hydrogen or $C_1$–$C_4$ alkyl radical;
  (2) $C_1$–$C_2$ alkyl radical substituted by phenyl or heteroaryl radical, wherein the phenyl or heteroaryl radical is optionally substituted by 1–3 radicals of amino, dimethylamino, acetamido, hydroxy, methoxy, methyl or trifluoromethyl radicals; or
  (3) phenyl or heteroaryl radical optionally substituted by 1–3 radicals of amino, dimethylamino, acetamido, hydroxy, methoxy, methyl or trifluoromethyl radicals.

7. The compound of claim 6 or a pharmaceutically acceptable salt thereof, wherein $R_2$ and $R_3$ are each independently —Z—Y, provided that (1) the total number of aryl, heteroaryl, cycloalkyl and heterocyclyl radicals in each —Z—Y is 0–3; and (2) the combined total number of aryl, heteroaryl, cycloalkyl and heterocyclyl radicals in $R_2$ and $R_3$ is 0–3.

8. The compound of claim 7 or a pharmaceutically acceptable salt thereof, wherein $R_3$ is halo, trifluoromethyl, phenyl, methyl, hydroxymethyl, hydroxyethyl, dimethylamino, methoxy, trifluoromethoxy, —C(O)—$R_{20}$, —C(O)—$OR_{21}$, —C(O)—$NR_5R_{21}$, —S(O)$_2$—$R_{20}$ or —S(O)$_2$—$NR_5R_{21}$ radicals;

$R_2$ is —Z—Y, provided that (1) the total number of aryl, heteroaryl, cycloalkyl and heterocyclyl radicals in each —Z—Y is 0–3; and (2) the combined total number of aryl, heteroaryl, cycloalkyl and heterocyclyl radicals in $R_2$ and $R_3$ is 0–3;

$R_{11}$ is a heteroaryl radical optionally substituted by 1–2 radicals of
(1) $R_{30}$;
(2) halo or cyano radicals; or
(3) —C(O)—$NR_{31}R_{32}$, —$OR_{29}$, —$SR_{29}$, —$NR_{31}R_{32}$ or —$NR_{33}$—C(O)—$R_{29}$ radicals; and $R_{12}$ is an aryl radical optionally substituted by 1–2 radicals of
(1) $R_{30}$;
(2) halo or cyano radicals; or
(3) —C(O)—$NR_{31}R_{32}$, —$OR_{29}$, —$SR_{29}$, —S(O)—$R_{30}$, —$S(O)_2$—$R_{30}$, —$S(O)_2$—$NR_{31}R_{32}$, —$NR_{31}R_{32}$ or —$NR_{33}$—C(O)—$R_{29}$ radicals;
provided that the total number of aryl, heteroaryl, cycloalkyl and heterocyclyl radicals substituted on each of $R_{11}$ and $R_{12}$ is 0–1.

9. The compound of claim 8 or a pharmaceutically acceptable salt thereof, wherein
$X_1$ is N; $X_2$ is $CR_2$; $X_3$ is CH or $CR_3$; and $X_4$ is N; and wherein $R_2$ is —Z—Y, provided that the combined total number of aryl, heteroaryl, cycloalkyl and heterocyclyl radicals in $R_2$ is 0–3;

$R_3$ is halo, trifluoromethyl, phenyl, methyl, hydroxymethyl, hydroxyethyl, dimethylamino, methoxy, trifluoromethoxy, acetyl, methoxycarbonyl, ethoxycarbonyl, amido, N,N-dimethylamido, methylsulfonyl or aminosulfonyl radicals;

Z is independently a
(1) bond; or
(2) $C_1$–$C_4$ alkyl radical optionally substituted by 1–2 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio, halo, or aryl or heteroaryl optionally substituted by 1–2 radicals of hydroxy, $C_1$–$C_2$ alkoxy, $C_1$–$C_2$ alkylthio, cyano, halo, $C_1$–$C_4$ alkyl or trifluoromethyl radicals;

each $R_5$ is independently hydrogen or $C_1$–$C_4$ alkyl radical; each $R_{20}$ is independently
(1) $C_1$–$C_8$ alkyl radicals optionally substituted by 1–3 radicals of —$CO_2R_{23}$, amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or $C_3$–$C_6$ cycloalkyl, heterocyclyl, aryl or heteroaryl radicals optionally substituted by 1–2 radicals of amino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, $C_1$–$C_4$ alkyl or trifluoromethyl radicals;
(2) heterocyclyl radical optionally substituted by 1–2 radicals of ($C_1$–$C_4$ alkoxy)carbonyl, hydroxy, $C_1$–$C_4$ alkoxy, $C_1$–$C_4$ alkylthio or $C_1$–$C_4$ alkyl; or
(3) aryl or heteroaryl radicals optionally substituted by 1–2 radicals of ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl radicals;

each $R_{21}$ is independently hydrogen radical or $R_{20}$;

each $R_{23}$ is independently hydrogen or $C_1$–$C_4$ alkyl, or phenyl-$C_1$–$C_2$-alkyl optionally substituted by 1–2 radicals of hydroxy, $C_1$–$C_2$ alkoxy, $C_1$–$C_2$ alkylthio, cyano, halo, $C_1$–$C_4$ alkyl or trifluoromethyl radicals;

$R_{10}$ is a hydrogen, $R_{30}$, —C(O)—$R_{29}$ or —C(O)—$NR_{31}R_{32}$ radical;

$R_{11}$ is a heteroaryl radical optionally substituted by 1–2 radicals of amino, dimethylamino, acetamido, hydroxy, halo, cyano, methoxy, methyl or trifluoromethyl radicals;

$R_{12}$ is an aryl radical optionally substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals;

$R_{29}$ is an aryl or heteroaryl radicals optionally substituted by 1–2 radicals of amino, dimethylamino, acetamido, hydroxy, halo, methoxy, methyl or trifluoromethyl radicals; and $R_{32}$ is independently
(1) hydrogen or $C_1$–$C_4$ alkyl radical; or
(2) phenyl or heteroaryl radical optionally substituted by 1–2 radicals of amino, dimethylamino, acetamido, hydroxy, methoxy, methyl or trifluoromethyl radicals.

10. The compound of claim 9 or a pharmaceutically acceptable salt thereof, wherein
Z is independently a
(1) bond; or
(2) $C_1$–$C_4$ alkyl radical optionally substituted by 1–2 radicals of amino, t-butoxycarbonylamino, dimethylamino, hydroxy, methoxy, methylthio or halo radicals;

Y is independently a
(1) hydrogen radical, provided Z is other than a bond;
(2) halo radical;
(3) —C(O)—$R_{20}$, —C(O)—$OR_{21}$ or —C(O)—$NR_5R_{21}$ radical;
(4) —$OR_{21}$, —$SR_{21}$, —S(O)—$R_{20}$, —$S(O)_2$—$R_{20}$ or —$S(O)_2$—$NR_5R_{21}$ radical; or
(5) —$NR_5R_{21}$, —$NR_{22}$—C(O)—$R_{21}$, —$NR_{22}$—$S(O)_2$—$R_{20}$ or —$NR_{22}$—$S(O)_2$—$NR_5R_{21}$ radical;

$R_5$ is a hydrogen radical;

each $R_{20}$ is independently
(1) $C_1$–$C_6$ alkyl radicals optionally substituted by 1–3 radicals of —$CO_2R_{23}$, amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;
(2) heterocyclyl radical optionally substituted by 1–2 radicals of t-butoxycarbonyl, hydroxy, or $C_1$–$C_4$ alkyl; or
(3) aryl or heteroaryl radicals optionally substituted by 1–2 radicals of t-butoxycarbonyl, hydroxy, methoxy, methylthio, cyano, halo, azido, methyl or trifluoromethyl radicals;

each $R_{21}$ is independently hydrogen radical or $R_{20}$;

each $R_{22}$ is independently hydrogen or methyl radical;

each $R_{23}$ is independently hydrogen or $C_1$–$C_4$ alkyl radicals;

$R_{10}$ is a hydrogen or methyl radical;

$R_{11}$ is a 4-pyridyl, 4-quinolinyl, 4-imidazolyl or 4-pyrimidinyl radical optionally substituted by a radical of amino, dimethylamino, acetamido, hydroxy, halo, cyano, methoxy, methyl or trifluoromethyl radicals;

$R_{12}$ is an unsubstituted phenyl or naphthyl radical or a phenyl radical substituted by 1–2 radicals of amino, dimethylamino, acetamido, hydroxy, halo, cyano, methoxy, methylthio, methylsulfinyl, methylsulfonyl, aminocarbonyl, methyl or trifluoromethyl radicals.

11. The compound of claim 1 which is:

3-(4-pyridyl)-2-(4-fluorophenyl)-4,7-diaza-indole;

6-(2'-amino-1'-oxo-butylamino)-3-(4-pyridyl)-2-(4-fluorophenyl)-1-methyl-4,7-diaza-indole;

6-(3'-methyl-2'(S)-amino-1'-oxo-butylamino)-3-(4-pyridyl)-2-(4-fluorophenyl)-1-methyl-4,7-diaza-indole;

6-(3'-hydroxy-2'(S)-amino-1'-oxo-propylamino)-3-(4-pyridyl)-2-(4-fluorophenyl)-1-methyl-4,7-diaza-indole;

6-(3'-phenyl-2'(S)-amino-1'-oxo-propylamino)-3-(4-pyridyl)-2-(4-fluorophenyl)-1-methyl-4,7-diaza-indole;

6-(3'-(4-methoxyphenyl)-2'(S)-amino-1'-oxo-propylamino)-3-(4-pyridyl)-2-(4-fluorophenyl)-1-methyl-4,7-diaza-indole;

6-(3'-pyrid-4-yl-2'(S)-amino-1'-oxo-propylamino)-3-(4-pyridyl)-2-(4-fluorophenyl)-1-methyl-4,7-diaza-indole;

6-(3'-pyrid-2-yl-2'(S)-amino-1'-oxo-propylamino)-3-(4-pyridyl)-2-(4-fluorophenyl)-1-methyl-4,7-diaza-indole;

6-(3'-methylthio-2'(S)-amino-1'-oxo-butylamino)-3-(4-pyridyl)-2-(4-fluorophenyl)-1-methyl-4,7-diaza-indole;

6-(3'-methylsulfinyl-2'(S)-amino-1'-oxo-butylamino)-3-(4-pyridyl)-2-(4-fluorophenyl)-1-methyl-4,7-diaza-indole; or a pharmaceutically acceptable salt thereof.

12. A pharmaceutical composition comprising a compound according to any of claims 1 to 11 and a pharmaceutically acceptable carrier.

13. A method of prophylaxis or treatment of inflammation comprising administering an effective amount of a compound according to any of claims 1 to 11.

14. A method of prophylaxis or treatment of inflammation comprising administering an effective amount of a composition of claim 12.

15. A method of prophylaxis or treatment of rheumatoid arthritis, Pagets disease, osteophorosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever or myalgias due to infection, or. infections of HIV-1, HIV-2, HIV-3, cytomegalovirus, influenza, adenovirus, herpes viruses or herpes zoster in a mammal comprising administering an effective amount of a compound according to any of claims 1 to 11.

16. A method of prophylaxis or treatment of rheumatoid arthritis, Pagets disease, osteophorosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever or myalgias due to infection, or infections of HIV-1, HIV-2, HIV-3, cytomegalovirus, influenza, adenovirus, herpes viruses or herpes zoster in a mammal comprising administering an effective amount of a composition of claim 12.

17. A method of lowering plasma concentrations of either or both TNF-a and IL-1 comprising administering an effective amount of a compound according to any of claims 1 to 11.

18. A method of lowering plasma concentrations of either or both TNF-a and IL-1 comprising administering an effective amount of a composition of claim 12.

19. A method of lowering plasma concentrations of either or both IL-6 and IL-8 comprising administering an effective amount of a compound according to any of claims 1 to 11.

20. A method of lowering plasma concentrations of either or both IL-6 and IL-8 comprising administering an effective amount of a composition of claim 12.

21. A method of prophylaxis or treatment of diabetes disease in a mammal comprising administering an effective amount of a compound according to any of claims 1 to 11 to produce a glucagon antagonist effect.

22. A method of prophylaxis or treatment of diabetes disease in a mammal comprising administering an effective amount of a pharmaceutical composition according to claim 12 to produce a glucagon antagonist effect.

23. A method of prophylaxis or treatment of a pain disorder in a mammal comprising administering an effective amount of a compound according to any of claims 1 to 11.

24. A method of prophylaxis or treatment of a pain disorder in a mammal comprising administering an effective amogunt of a pharmaceutical composition according to claim 12.

25. A method of decreasing prostaglandins production in a mammal comprising administering an effective amount of a compound according to any of claims 1 to 11.

26. A method of decreasing prostaglandins production in a mammal comprising administering an effective amount of a pharmaceutical composition according to claim 12.

27. A method of decreasing cyclooxygenase enzyme activity in a mammal comprising administering an effective amount of a compound according to any of claims 1 to 11.

28. The method of claim 27 wherein the cyclooxygenase enzyme is COX-2.

29. A method of decreasing cyclooxygenase enzyme activity in a mammal comprising administering an effective amount of a pharmaceutical composition according to claim 12.

30. The method of claim 29 wherein the cyclooxygenase enzyme is COX-2.

* * * * *

UNITED STATES PATENT AND TRADEMARK OFFICE
CERTIFICATE OF CORRECTION

PATENT NO.     : 6,440,973 B1
DATED          : August 27, 2002
INVENTOR(S)    : Zablocki et al.

It is certified that error appears in the above-identified patent and that said Letters Patent is hereby corrected as shown below:

Column 1,
Lines 66-67, change "inpa-tients" to read -- in patients --.

Column 2,
Line 58, delete the period after "levels." to read -- levels --.

Column 25,
Line 32, delete the period after "above,." to read -- above, --.

Column 30,
Line 45, delete the period after "those." to read -- those --.

Column 39,
Line 18, delete the period after "into." to read -- into --.

Column 48,
Line 9, change "CuI." to read -- CuI, --.

Column 53,
Line 63, change "OR20" to read -- $OR_{20}$ --.
Line 64, delete the period after "Reaction of." to read -- Reaction of --.

Column 55,
Line 14, after "PCl" add -- 5 --.

Column 60,
Line 26, delete the period after "60° C." to read -- 60° C --.
Line 28, delete the period after "60° C.," to read -- 60° C, --.
Line 29, delete the period after "23° C." to read -- 23° C --.

Column 61,
Line 20, delete the period after "-20-30° C." to read -- 20-30° C --.
Line 23, delete the period after "23° C.," to read -- 23° C, --.
Line 53, delete the period after "23° C." to read -- 23° C --.

Column 67,
Line 67, change "(MH-)" to read -- (MH+) --

UNITED STATES PATENT AND TRADEMARK OFFICE
CERTIFICATE OF CORRECTION

PATENT NO. : 6,440,973 B1
DATED : August 27, 2002
INVENTOR(S) : Zablocki et al.

It is certified that error appears in the above-identified patent and that said Letters Patent is hereby corrected as shown below:

Column 71,
Line 61, delete the period after "23° C." to read -- 23° C--.

Column 72,
Line 62, delete the periods after "60° C." & "23° C.," to read -- 60° C --; and -- 23° C, --.

Column 74,
Line 38, delete the period after "190° C." to read -- 190° C --.
Line 39, delete the period after "190° C.," to read -- 190° C,--.
Line 40, delete the period after "23° C." to read -- 23° C --.

Column 91,
Line 44, change "(MH-)" to read -- (MH+) --.

Column 92,
Line 2, change "(MH-)" to read -- (MH+) --.

Column 93,
Line 67, change "(MH-)" to read -- (MH+) --.

Column 94,
Line 45, change "(MH-)" to read -- (MH+) --.

Column 95,
Line 22, change "(MH-)" to read -- (MH+) --.

Column 97,
Line 21, change "(MH-)" to read -- (MH+) --.

Column 107,
Line 56, change "(PBMCS)" to read -- (PBMCs) --.
Line 64, delete the period after "37° C." to read -- 37° C --.

Column 108,
Line 22, delete the period after "(4° C.)" to read -- (4° C) --.
Line 52, change "ICSO" to read -- $IC_{50}$ --.

UNITED STATES PATENT AND TRADEMARK OFFICE
CERTIFICATE OF CORRECTION

PATENT NO.   : 6,440,973 B1
DATED        : August 27, 2002
INVENTOR(S)  : Zablocki et al.

It is certified that error appears in the above-identified patent and that said Letters Patent is hereby corrected as shown below:

Column 111,
Line 21, delete the period after "-20° C.;" to read -- -20° C; --.
Line 24, change "(1 pi yields" to read -- 1 $\mu$l yields --.
Line 24, delete the period after "-20° C.," to read -- -20° C, --.
Line 31, delete the period after "grade,." to read -- grade, --.
Line 66, delete the period after "22° C." to read -- 22° C --.

Column 112,
Line 22, delete the period after "37° C." to read -- 37° C --.
Line 35, delete the period after "37° C.," to read -- 37° C, --.
Line 53, delete the period after "37° C.," to read -- 37° C, --.

Column 113,
Line 48, delete the period after "colitis.," to read -- colitis, --.
Line 57, delete the period after "multiple.sclerosis" to read -- multiple sclerosis --.

Signed and Sealed this

Twenty-sixth Day of August, 2003

JAMES E. ROGAN
*Director of the United States Patent and Trademark Office*